US012715875B2

(12) United States Patent
Gomez et al.

(10) Patent No.: US 12,715,875 B2
(45) **Date of Patent: *Aug. 25, 2026**

(54) SUBSTITUTED PYRAZOLOPYRIMIDINONE COMPOUNDS AS PDE2 INHIBITORS

(71) Applicant: DART NEUROSCIENCE, LLC, Dallas, TX (US)

(72) Inventors: Laurent Gomez, San Diego, CA (US); William Francois Vernier, San Diego, CA (US)

(73) Assignee: Dart NeuroScience LLC, Dallas, TX (US)

(*) Notice: Subject to any disclaimer, the term of this patent is extended or adjusted under 35 U.S.C. 154(b) by 267 days.

This patent is subject to a terminal disclaimer.

(21) Appl. No.: 18/677,491

(22) Filed: May 29, 2024

(65) Prior Publication Data

US 2025/0136604 A1 May 1, 2025

Related U.S. Application Data

(63) Continuation of application No. 17/232,015, filed on Apr. 15, 2021, now Pat. No. 11,999,738, which is a continuation of application No. 16/473,864, filed as application No. PCT/US2017/068229 on Dec. 22, 2017, now Pat. No. 10,981,916.

(60) Provisional application No. 62/439,823, filed on Dec. 28, 2016.

(51) Int. Cl.

| | |
|---|---|
| ***C07D 487/04*** | (2006.01) |
| ***A61K 31/519*** | (2006.01) |
| ***A61P 25/00*** | (2006.01) |
| ***A61P 25/22*** | (2006.01) |
| ***A61P 25/24*** | (2006.01) |
| ***A61P 25/28*** | (2006.01) |

(52) U.S. Cl.
CPC ............ *C07D 487/04* (2013.01); *A61P 25/28* (2018.01)

(58) Field of Classification Search
CPC ..... C07D 487/04; A61K 31/519; A61P 25/28; A61P 25/00; A61P 25/22; A61P 25/24
See application file for complete search history.

(56) References Cited

U.S. PATENT DOCUMENTS

| | | | |
|---|---|---|---|
| 4,938,949 | A | 7/1990 | Borch et al. |
| 5,294,612 | A | 3/1994 | Bacon et al. |
| 5,824,683 | A | 10/1998 | Kittrick et al. |
| 6,174,884 | B1 | 1/2001 | Haning et al. |
| 6,235,742 | B1 | 5/2001 | Bell et al. |
| 7,022,709 | B2 | 4/2006 | Böss et al. |
| 7,268,128 | B2 | 9/2007 | Inoue et al. |
| 7,528,148 | B2 | 5/2009 | Allen et al. |
| 7,868,015 | B2 | 1/2011 | Tully et al. |
| 7,947,731 | B2 | 5/2011 | Tully et al. |
| 8,697,710 | B2 | 4/2014 | Li et al. |
| 8,846,693 | B2 | 9/2014 | Li et al. |
| 8,859,564 | B2 | 10/2014 | Li et al. |
| 8,927,556 | B2 | 1/2015 | Li et al. |
| 9,023,849 | B2 | 5/2015 | Follmann et al. |
| 9,290,511 | B2 | 3/2016 | Madge et al. |
| 10,981,916 | B2 | 4/2021 | Gomez et al. |
| 11,434,247 | B1 | 9/2022 | Bookser et al. |
| 11,999,738 | B2 | 6/2024 | Gomez et al. |

(Continued)

FOREIGN PATENT DOCUMENTS

| | | |
|---|---|---|
| EP | 0063381 | 10/1982 |
| EP | 0636626 | 2/1995 |

(Continued)

OTHER PUBLICATIONS

Abel et al., 1997, Genetic demonstration of a role for PKA in the late phase of LTP and in hippocampus-based long-term memory. Cell. 88(5):615-626.

Ahn et al., 1997, Potent tetracyclic guanine inhibitors of PDE1 and PDE5 cyclic guanosine monophosphate phosphodiesterases with oral antihypertensive activity. J Med Chem., 40(14):2196-2210.

Alberini C.M., 2009, Transcription Factors in Long-Term Memory and Synaptic Plasticity. Physiol. Rev. 89(1) in 46 pages.

Allen et al., 2012, Exercise and Motor Training in People with Parkinson's Disease: A Systematic Review of Participant Characteristics, Intervention Delivery, Retention Rates, Adherence, and Adverse Events in Clinical Trials. Parkinsons Dis. Article ID 854328 in 15 pages.

(Continued)

*Primary Examiner* — Kamal A Saeed
*Assistant Examiner* — Sagar Patel
(74) *Attorney, Agent, or Firm* — Knobbe, Martens, Olson & Bear, LLP

(57) ABSTRACT

A chemical entity of Formula (I):

(I)

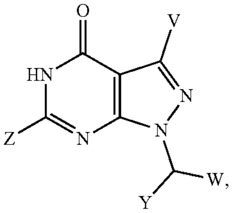

wherein V, W, Y, and Z, have any of the values described herein, and compositions comprising such chemical entities; methods of making them; and their use in a wide range of methods, including metabolic and reaction kinetic studies; detection and imaging techniques; radioactive treatments; modulating and treating disorders mediated by PDE2 activity; treating neurological disorders, CNS disorders, dementia, cognitive disorders, neurodegenerative diseases, and trauma-dependent losses of function; enhancing the efficiency of cognitive and motor training, including in stroke or TBI rehabilitation; and treating peripheral disorders, including hematological, cardiovascular, gastroenterological, dermatological, inflammatory, and pain disorders.

20 Claims, No Drawings

(56) References Cited

U.S. PATENT DOCUMENTS

| | | | |
|---|---|---|---|
| 12,006,325 | B2 | 6/2024 | Bookser et al. |
| 2005/0004142 | A1 | 1/2005 | Adams et al. |
| 2006/0089375 | A1 | 4/2006 | Allen et al. |
| 2007/0275984 | A1 | 11/2007 | Imogai et al. |
| 2008/0188525 | A1 | 8/2008 | Hallam et al. |
| 2009/0053140 | A1 | 2/2009 | Scott et al. |
| 2009/0137549 | A1 | 5/2009 | Edward et al. |
| 2010/0063047 | A1 | 3/2010 | Borchardt et al. |
| 2010/0173878 | A1 | 7/2010 | Li et al. |
| 2010/0273754 | A1 | 10/2010 | Li |
| 2012/0065200 | A1 | 3/2012 | Barbosa et al. |
| 2012/0122846 | A1 | 5/2012 | Calderwood et al. |
| 2013/0338124 | A1 | 12/2013 | Li et al. |
| 2013/0338139 | A1 | 12/2013 | Allan et al. |
| 2014/0018361 | A1 | 1/2014 | Harriman et al. |
| 2015/0175584 | A1 | 6/2015 | Kehler et al. |
| 2015/0191463 | A1 | 7/2015 | Nagai et al. |
| 2016/0039829 | A1 | 2/2016 | Li et al. |
| 2016/0083391 | A1 | 3/2016 | Burdi et al. |
| 2016/0311831 | A1 | 10/2016 | Kehler et al. |
| 2016/0347759 | A1 | 12/2016 | Kehler et al. |
| 2017/0022186 | A1 | 1/2017 | Kehler et al. |
| 2017/0273985 | A1 | 9/2017 | Burdi et al. |
| 2017/0298072 | A1 | 10/2017 | Kehler et al. |
| 2018/0044343 | A1 | 2/2018 | Fujii et al. |
| 2019/0177327 | A1 | 6/2019 | Bookser et al. |
| 2020/0148685 | A1 | 5/2020 | Gomez et al. |

FOREIGN PATENT DOCUMENTS

| | | | |
|---|---|---|---|
| EP | 0729758 | 9/1996 | |
| EP | 0995751 | 4/2000 | |
| EP | 1460077 | 9/2004 | |
| EP | 2644590 | 10/2013 | |
| JP | H08253484 | 10/1996 | |
| JP | 2006503108 | 1/2006 | |
| JP | 2013539762 | 10/2013 | |
| KR | 20000043995 | 7/2000 | |
| KR | 20050088214 A | 9/2005 | |
| WO | WO 1991/19717 | 12/1991 | |
| WO | WO 1993/07149 | 4/1993 | |
| WO | WO 1994/19351 | 9/1994 | |
| WO | WO 1996/16657 | 6/1996 | |
| WO | WO 1996/28429 | 9/1996 | |
| WO | WO 1996/28448 | 9/1996 | |
| WO | WO 1997/19947 | 6/1997 | |
| WO | WO 2000/011002 | 3/2000 | |
| WO | WO 2002/009713 | 2/2002 | |
| WO | WO 2004/024082 | 3/2004 | |
| WO | WO 2004/096811 | 11/2004 | |
| WO | WO 2004/111054 | 12/2004 | |
| WO | WO 2003/053975 | 4/2005 | |
| WO | WO 2006/133261 | 12/2006 | |
| WO | WO 2007/079862 | 7/2007 | |
| WO | WO 2008/055959 | 5/2008 | |
| WO | WO 2008/057402 | 5/2008 | |
| WO | WO 2008/070095 | 6/2008 | |
| WO | WO 2008/139293 | 11/2008 | |
| WO | WO 2009/067166 | 5/2009 | |
| WO | WO 2010/084438 | 7/2010 | |
| WO | WO 2013/104598 | 7/2013 | |
| WO | WO 2014/026328 | 2/2014 | |
| WO | WO 2014/131855 | 9/2014 | |
| WO | WO 2016/020307 | 2/2016 | |
| WO | WO 2014/017643 | 7/2016 | |
| WO | WO 2016/174188 | 11/2016 | |
| WO | WO 2016/191935 | 12/2016 | |
| WO | WO 2016/192083 | 12/2016 | |
| WO | WO 2016/196071 | 12/2016 | |
| WO | WO 2016/196417 | 12/2016 | |
| WO | WO 2016/209749 | 12/2016 | |
| WO | WO-2016191935 A1 * | 12/2016 | ........... A61K 31/519 |
| WO | WO 2017/000276 | 1/2017 | |
| WO | WO 2017/000277 | 1/2017 | |
| WO | WO 2017/003894 | 1/2017 | |
| WO | WO 2017/003895 | 1/2017 | |
| WO | WO 2017/139186 | 8/2017 | |
| WO | WO 2017/146116 | 8/2017 | |
| WO | WO 2017/178350 | 10/2017 | |

OTHER PUBLICATIONS

Banerjee et al., 2012, Isothiazole and isoxazole fused pyrimidones as PDE7 inhibitors: SAR and pharmacokinetic evaluation. Bioorg Med Chem Lett. 22:3223-3228.

Banerjee et al., 2012, Imidazopyridazinones as novel PDE7 inhibitors: SAR and in vivo studies in Parkinson's disease model. Bioorg Med Chem Lett. 22(19):6286-6291.

Barnes et al., 2001, Synthesis and Structure—Activity Relationships of Guanine Analogues as Phosphodiesterase 7 (PDE7) Inhibitors. Bioorg Med Chem Lett. 11:1081-1083.

Belleville et al., 2006, Improvement of episodic memory in persons with mild cognitive impairment and healthy older adults: evidence from a cognitive intervention program. Dement Geriatr Cogn Disord. 22(5-6):486-499.

Bender et al., 2006, Cyclic nucleotide phosphodiesterases: molecular regulation to clinical use. Pharmacol Rev. 58(3):488-520.

Berge et al., 1977, Pharmaceutical salts. J Pharm Sci. 66(1):1-19.

Bevins et al., 2006, Object recognition in rats and mice: a one-trial non-matching-to-sample learning task to study 'recognition memory'. Nat Protoc. 1(3):1306-1311.

Bourtchouladze et al., 1998, Different training procedures recruit either one or two critical periods for contextual memory consolidation, each of which requires protein synthesis and PKA. Learn Mem. 5(4-5):365-374.

Bourtchouladze et al., 2003, A mouse model of Rubinstein-Taybi syndrome: Defective long-term memory is ameliorated by inhibitors of phosphodiesterase 4. PNAS U S A. 100(18):10518-10522.

CAS Database Registry No. 1031631-67-0; Furo [2,3-d]pyrimidine-5-carboxylic acid, Entered STN: Jun. 29, 2008, 1 page.

Chein et al., 2010, Expanding the mind's workspace: training and transfer effects with a complex working memory span task. Psychon Bull Rev. 17(2):193-199.

Chen et al., 1996, Hippocampal lesions impair contextual fear conditioning in two strains of mice. Behav Neurosci. 110(5):1177-1180. [Best available copy].

Cheng et al., 2007, Cyclic nucleotide phosphodiesterase (PDE) inhibitors: novel therapeutic agents for progressive renal disease. Exp Biol Med (Maywood) 232(1):38-51.

Damasio A.R. 1996, Alzheimer's Disease and Related Dementias. In *In Cecil Textbook of Medicine*, Bennett et al. [Eds.]; 20th Edition, vol. 2, Chapter 400, pp. 1992-1996.

DeNinno et al., 2009, The discovery of potent, selective, and orally bioavailable PDE9 inhibitors as potential hypoglycemic agents. Bioorg Medicinal Chemistry Letters, 19(9), 2537-2541.

Dean et al., 2000, Task-related circuit training improves performance of locomotor tasks in chronic stroke: a randomized, controlled pilot trial. Arch Phys Med Rehabil. 81(4):409-417.

De Tejada et al., 2001, The phosphodiesterase inhibitory selectivity and the in vitro and in vivo potency of the new PDE5 inhibitor vardenafil. Int J Impot Res. 13(5):282-290.

Dousa T.P., 1999. Cyclic-3',5'-nucleotide phosphodiesterase isozymes in cell biology and pathophysiology of the kidney. Kidney Int. 55(1):29-62.

Dumas et al., 2013, A review of cognition in Huntington's disease. Front Biosci (Schol Ed). Chapter 2; 29 pages.

Dyck et al., 2017, Discovery of Selective Phosphodiesterase 1 Inhibitors with Memory Enhancing Properties. J Med Chem. 60(8):3472-3483.

Endo et al., 2015, Discovery and SAR study of 2-(4-pyridylamino)thieno[3,2-d] pyrimidin-4(3H)-ones as soluble and highly potent PDE7 inhibitors. Bioorg Med Chem Lett. 25:649-653.

Fanselow M.S., 1984, Opiate modulation of the active and inactive components of the postshock reaction: parallels between naloxone pretreatment and shock intensity. Behav Neurosci. 98(2):269-277.

(56) References Cited

OTHER PUBLICATIONS

Fischer et al., 2007, Hand rehabilitation following stroke: a pilot study of assisted finger extension training in a virtual environment. Top Stroke Rehabil. 14(1):1-12.
Frankland et al., 1998, The dorsal hippocampus is essential for context discrimination but not for contextual conditioning. Behav Neurosci. 112(4):863-874.
Frazzitta et al., 2009, Rehabilitation treatment of gait in patients with Parkinson's disease with freezing: a comparison between two physical therapy protocols using visual and auditory cues with or without treadmill training. Mov Disord. 24(8):1139-1143.
Garcia et al., 2014, Modulation of CAMP-specific PDE without emetogenic activity: new sulfide-like PDE7 inhibitors. J Med Chem. 57(2):8590-8607.
Gewald et al., 2011, Synthesis and structure-activity relationship studies of dihydronaphthyridinediones as a novel structural class of potent and selective PDE7 inhibitors. Bioorg Med Chem Lett. 21(22):6652-6656.
Giese et al., 1998, Autophosphorylation at Thr286 of the alpha calcium-calmodulin kinase II in LTP and learning. Science. 279(5352):870-873.
Go et al., 2013, Heart Disease and Stroke Statistics; A Report From the American Heart Association. Circulation. 129:e28-e92.
Goldman et al., 2011, Mild Cognitive Impairment in Parkinson's Disease. Minerva Med. 102(6):441-459.
Goraya et al., 2005, $Ca^{2+}$-calmodulin-dependent phosphodiesterase (PDE1): current perspectives. Cell Signal 17(7):789-797.
Gordon et al., 2004, Physical activity and exercise recommendations for stroke survivors: an American Heart Association scientific statement from the Council on Clinical Cardiology, Subcommittee on Exercise, Cardiac Rehabilitation, and Prevention; the Council on Cardiovascular Nursing; the Council on Nutrition, Physical Activity, and Metabolism; and the Stroke Council. Stroke. 35(5):1230-1240.
He et al, 2017, The Selection of a Pharmaceutical Salt—the Effect of the Acidity of the Counterion on Its Solubility and Potential Biopharmaceutical Performance; doi: 10.1016/j.xphs.2017.10.032; J Pharmaceutical Sciences (2017) ().
Hill et al., 2015, Increasing Adult Hippocampal Neurogenesis is Sufficient to Reduce Anxiety and Depression-Like Behaviors. Neuropsychopharmacology. 40(10):2368-2378.
Hummelsheim et al., 1999, Repetitive sensorimotor training for arm and hand in a patient with locked-in syndrome. Scand J Rehabil Med. 31(4):250-256.
Humphrey et al., 2014, Small-molecule phosphodiesterase probes: discovery of potent and selective CNS-penetrable quinazoline inhibitors of PDE1. Med Chem Comm. 5:1290-1298.
Jaeggi et al., 2008, Improving fluid intelligence with training on working memory. PNAS U S A. 105(19):6829-6833.
Jaeggi et al., 2011, Short- and long-term benefits of cognitive training. PNAS U S A. 108(25):10081-10086.
Jakovljevic et al., 2006, The effects of nimodipine and L-NAME on coronary flow and oxidative stress parameters in isolated rat heart. Acta Physiol Hung. 93(4):251-261.
Jankowska et al., 2017, PDE7-Selective and Dual Inhibitors: Advances in Chemical and Biological Research. Curr Med Chem. 24:673-700.
Jonsdottir et al., 2007, Concepts of motor learning applied to a rehabilitation protocol using biofeedback to improve gait in a chronic stroke patient: an A-B system study with multiple gait analyses. Neurorehabil Neural Repair 21(2):191-194.
Jordan V.C. 2003, Tamoxifen: A Most Unlikely Pioneering Medicine. Nature Reviews 2: 205-213.
Kakiuchi et al., 1970, Calcium dependent phosphodiesterase activity and its activating factor (PAF) from brain studies on cyclic 3',5'-nucleotide phosphodiesterase (3). Biochem Biophys Res Commun., 41(5):1104-1110.
Keefe et al., 2012, Cognitive impairment in schizophrenia. Handb Exp Pharmacol. 213:11-37.
Kempson et al., 2005, Fused pyrimidine based inhibitors of phosphodiesterase 7 (PDE7): synthesis and initial structure-activity relationships. Bioorg Med Chem Ltts. 15:1829-1833.
Keravis et al., 2012, Cyclic nucleotide phosphodiesterase (PDE) isozymes as targets of the intracellular signaling network: benefits of PDE inhibitors in various diseases and perspectives for future therapeutic developments. Br J Pharmacol. 165(5):1288-1305.
Kheirbek et al., 2012, Neurogenesis and generalization: a new approach to stratify and treat anxiety disorders. Nat Neurosci. 15(12):1613-1620.
Kim et al., 1993, Effects of amygdala, hippocampus, and periaqueductal gray lesions on short- and long-term contextual fear. Behav Neurosci. 107(6):1093-1098.
Kim et al., 2014, Effect of Dual-task Rehabilitative Training on Cognitive and Motor Function of Stroke Patients. J Phys Ther Sci. 26(1):1-6.
Klingberg et al., 2005, Computerized training of working memory in children with ADHD—a randomized, controlled trial. J Am Acad Child Adolesc Psychiatry 44(2):177-186.
Klingberg, 2010, Training and plasticity of working memory. Trends Cogn Sci. 14(7):317-324.
Kogan et al., 1996, Spaced training induces normal long-term memory in CREB mutant mice. Curr Biol. 7(1):1-11.
Krakauer J.W., 2006, Motor learning: its relevance to stroke recovery and neurorehabilitation. Curr Opin Neurol. 19:84-90.
Kwakkel et al., 1996, Predicting disability in stroke—a critical review of the literature. Age Ageing 25(6):479-489.
Laursen et al., 2017, Novel selective PDE type 1 inhibitors cause vasodilatation and lower blood pressure in rats. Br J Pharmacol. 174(15):2563-2575.
Layzer R.B. 1996, Degenerative Diseases of the Nervous System. In *Cecil Textbook of Medicine*, Bennett et al. [Eds.]; 20th Edition, vol. 2, Section Five, pp. 2050-2057.
Li et al., 2016, Discovery of Potent and Selective Inhibitors of Phosphodiesterase 1 for the Treatment of Cognitive Impairment Associated with Neurodegenerative and Neuropsychiatric Diseases. J Med Chem. 59(3):1149-1164.
Litvan et al., 2012, Diagnostic Criteria for Mild Cognitive Impairment in Parkinson's Disease: Movement Disorder Society Task Force Guidelines. Mov Disord. 27(3):349-356.
Lorthiois et al., 2004, Spiroquinazolinones as novel, potent, and selective PDE7 inhibitors. Part 1. Bioorg Med Chem Lett. 14:4623-4626.
Lustig et al., 2009, Aging, training, and the brain: A review and future directions. Neuropsychol Rev. 19(4):504-522.
Maren et al., 1997, Neurotoxic lesions of the dorsal hippocampus and Pavlovian fear conditioning in rats. Behav Brain Res. 88(2):261-274.
Maren et al., 1997, Electrolytic lesions of the fimbria/fornix, dorsal hippocampus, or entorhinal cortex produce anterograde deficits in contextual fear conditioning in rats. Neurobiol Learn Mem. 67(2):142-149.
Maurice et al., 2003, Cyclic nucleotide phosphodiesterase activity, expression, and targeting in cells of the cardiovascular system. Mol Pharm. 64(3):533-546.
Medina A.E., 2011, Therapeutic Utility of Phosphodiesterase Type I Inhibitors in Neurological Conditions. Front Neurosci. 5:21 in 5 pages.
Merzenich et al., 1996, Temporal processing deficits of language-learning impaired children ameliorated by training. Science 271(5245):77-81.
Miller et al, 2009, Role of $Ca^{2+}$/calmodulin-stimulated cyclic nucleotide phosphodiesterase 1 in mediating cardiomyocyte hypertrophy. Circ Res. 105(10):956-964.
Miller et al., 2011, Cyclic nucleotide phosphodiesterase 1A: a key regulator of cardiac fibroblast activation and extracellular matrix remodeling in the heart. Basic Res Cardiol. 106(6):1023-1039.
Ming et al., 2011, Adult Neurogenesis in the Mammalian Brain: Significant Answers and Significant Questions. Neuron 70(4):687-702.

(56) References Cited

OTHER PUBLICATIONS

Morales-Garcia et al., 2014, Silencing phosphodiesterase 7B gene by lentiviral-shRNA interference attenuates neurodegeneration and motor deficits in hemiparkinsonian mice. Neurobiol Aging. 36:1160-1173.
Morales-Garcia et al., 2016, Phosphodiesterase7 Inhibition Activates Adult Neurogenesis in Hippocampus and Subventricular Zone In Vitro and In Vivo. Stem Cells. 35(2):458-472.
Mumby D.G., 2001, Perspectives on object-recognition memory following hippocampal damage: lessons from studies in rats. Behav Brain Res. 127(1-2):159-181.
Murray et al., 2007, Expression and activity of cAMP phosphodiesterase isoforms in pulmonary artery smooth muscle cells from patients with pulmonary hypertension: role for PDE1. Am J Physiol Lung Cell Mol Physiol., 292(1):L294-L303.
Nakayama et al., 1994, Recovery of upper extremity function in stroke patients: the Copenhagen Stroke Study. Arch Phys Med Rehabil. 75(4):394-398.
Nakayamada et al., Chemical JAK inhibitors for the treatment of rheumatoid arthritis. Exp Opin Pharmacother. (2016) 17(16):2215-25.
Ngyyen et al., 2000, Strain-dependent Differences in LTP and Hippocampus-dependent Memory in Inbred Mice. Learn Mem. 7(3):170-179.
Nishi et al., 2010, Advanced research on dopamine signaling to develop drugs for the treatment of mental disorders: biochemical and behavioral profiles of phosphodiesterase inhibition in dopaminergic neurotransmission. J Pharmacol Sci. 114:6-16.
Nozaki M. et al., 1995, Pharmaceutical Chemistry, 1st Edition, 6th Printing, Kagakudojin Publisher, pp. 98-99. (No English language version available).
Oujamaa et al., 2009, Rehabilitation of arm function after stroke. Literature review. Ann Phys Rehabil Med. 52(3):269-293.
Owen et al., 2010, Putting brain training to the test. Nature 465:775-778.
Park et al., 2009, The Adaptive Brain: Aging and Neurocognitive Scaffolding.Ann Rev Psych. 60:173-196.
Phillips et al., 1992, Differential contribution of amygdala and hippocampus to cued and contextual fear conditioning. Behav Neurosci. 106(2):274-285.
Pitts et al., 2004, Identification of purine inhibitors of phosphodiesterase 7 (PDE7). Bioorg Med Chem Lett. 14:2955-2958.
Ramirez et al., 2014, Regulation of dopamine signaling in the striatum by phosphodiesterase inhibitors: novel therapeutics to treat neurological and psychiatric disorders. Cent Nerv Syst Agents Med Chem 14(2):72-82.
Reed et al., 2002, Phosphodiesterase 1B knock-out mice exhibit exaggerated locomotor hyperactivity and DARPP-32 phosphorylation in response to dopamine agonists and display impaired spatial learning. J Neurosci. 22(12):5188-5197.
Rider et al., 1991, Effects of massed versus distributed practice on gross and fine motor proficiency of educable mentally handicapped adolescents. Percept Mot Skills. 73(1):219-224.
Robinson et al., 1996, Discovery of the hemifumarate and (alpha-L-alanyloxy)methyl ether as prodrugs of an antirheumatic oxindole: prodrugs for the enolic OH group. J Med Chem. 39(1):10-18.
Sanberg et al., 1998, The catalepsy test: its ups and downs. Behav Neurosci. 102(5):748-759.
Sancesario et al., 2004, Down-regulation of nitrergic transmission in the rat striatum after chronic nigrostriatal deafferentation. Eur J Neurosci. 20(4):989-1000.
Sasaki et al., 2004, Transcriptional activation of phosphodiesterase 7B1 by dopamine D1 receptor stimulation through the cyclic AMP/cyclic AMP-dependent protein kinase/cyclic AMP-response element binding protein pathway in primary striatal neurons. J Neurochem. 89(2):474-483.
Schermuly et al., 2007, Phosphodiesterase 1 upregulation in pulmonary arterial hypertension: target for reverse-remodeling therapy. Circulation. 115(17):2331-2339.
Schmidt C.J., 2010, Phosphodiesterase Inhibitors as Potential Cognition Enhancing Agents. Curr Top Med Chem. 10(2):222-230.
Sharma et al., 2006, Regulation of calmodulin-stimulated cyclic nucleotide phosphodiesterase (PDE1): review. Int J Mol Med. 18(1):95-105.
Shors et al., 2001, Neurogenesis in the adult is involved in the formation of tracememories. Nature 410(6826):372-376.
Shors et al., 2004, Memory traces of trace memories: neurogenesis, synaptogenesis and awareness. Trends Neurosci. 27(5):250-256.
Silva et al., 1996, Impaired learning in mice with abnormal short-lived plasticity. Curr Biol. 6(11):1509-1518.
Silver et al., 1994, Cyclic GMP potentiation by WIN 58237, a novel cyclic nucleotide phosphodiesterase inhibitor. J Pharmacol Exp Ther., 271(3):1143-1149.
Teng et al., 2000, Contrasting effects on discrimination learning after hippocampal lesions and conjoint hippocampal-caudate lesions in monkeys. J Neurosci. 20(10):3853-3863.
Terrett et al., 1996, Sildenafil (VIAGRA™), a potent and selective inhibitor of type 5 cGMP phosphodiesterase with utility for the treatment of male erectile dysfunction. Bioorg. Med. Chem. Lett., 6(15):1819-1824.
Tsao et al., 2010, Motor training of the lumbar paraspinal muscles induces immediate changes in motor coordination in patients with recurrent low back pain. J Pain 11(11):1120-1128.
Vergne et al., 2004, Discovery of thiadiazoles as a novel structural class of potent and selective PDE7 inhibitors. Part 1: design, synthesis and structure-activity relationship studies. Bioorg Med Chem Lett. 14(18):4607-4613.
Vergne et al., 2004, Discovery of thiadiazoles as a novel structural class of potent and selective PDE7 inhibitors. Part 2: metabolism-directed optimization studies towards orally bioavailable derivatives. Bioorg Med Chem Lett. 14, 4615-4621.
Vitolo et al., 2002, Amyloid β-peptide inhibition of the PKA/CREB pathway and long-term potentiation: Reversibility by drugs that enhance cAMP signaling. PNAS U.S.A. 99(20):13217-13221.
Volpe et al., 2008, Intensive sensorimotor arm training mediated by therapist or robot improves hemiparesis in patients with chronic stroke. Neurorehabil Neural Repair. 22(3):305-310.
Wang et al., 2010, Cyclic Nucleotide Signaling in Polycystic Kidney Disease. Kidney Int. 77(2):129-140.
Wang et al., 2015, Phosphodiesterase: an interface connecting cognitive deficits to neuropsychiatric and neurodegenerative diseases. Curr Pharm Des. 21(3):303-316.
Wang et al., 2017, Generation and phenotypic characterization of Pde1a mutant mice. PLoS One 12(7):e0181087 in 19 pages.
Whitall et al., 2000, Repetitive bilateral arm training with rhythmic auditory cueing improves motor function in chronic hemiparetic stroke. Stroke 31(1):2390-2395.
International Search Report and Written Opinion mailed Mar. 22, 2018 for Application No. PCT/US2017/068229, filed Dec. 22, 2017.

* cited by examiner

SUBSTITUTED PYRAZOLOPYRIMIDINONE COMPOUNDS AS PDE2 INHIBITORS

CROSS REFERENCE TO RELATED APPLICATIONS

This application is a continuation of U.S. application Ser. No. 17/232,015, filed Apr. 15, 2021, now U.S. Pat. No. 11,999,738, which is a continuation of U.S. application Ser. No. 16/473,864, filed Jun. 26, 2019, now U.S. Pat. No. 10,981,916, which is the U.S. National Phase under 35 U.S.C. § 371 of International Application No. PCT/US2017/068229, filed Dec. 22, 2017, designating the U.S. and published in English as International Pub. No. WO 2018/125810, which claims the benefit of U.S. Provisional Application No. 62/439,823, filed Dec. 28, 2016, each of which is incorporated herein by reference in its entirety.

BACKGROUND

Field

The present disclosure relates to the fields of chemistry and medicine. More specifically, the present disclosure relates to compounds and compositions that can inhibit PDE2 and are useful in various methods and therapies.

Description of the Related Technology

The mammalian phosphodiesterases (PDEs) are a group of closely related enzymes divided into 11 families, PDE1-11, based on substrate specificity, inhibitor sensitivity, and more recently, on sequence homology. The 11 families are coded by 21 genes, reflecting multiple members in several families. Numerous studies have highlighted a role for PDEs generally in modulating intracellular signaling pathways that regulate many physiological processes, including those underling neural plasticity, cognition, and memory (Menniti et al, *Nat Rev Drug Discov.* 2006, 5, 660-670). In particular, PDEs play an important role in intracellular signal transduction pathways involving the cyclic nucleotides, cAMP and cGMP, as second messengers. These cyclic nucleotides function as ubiquitous intracellular signaling molecules in all mammalian cells. PDE enzymes hydrolyze cAMP and cGMP by breaking phosphodiester bonds to form the corresponding monophosphates (Bender and Beavo, *Pharmacol. Rev.* 2006, 58, 488-520). PDE activities are modulated in coordination with adenylyl cyclase (AC) and guanylyl cyclase (GC) activities through direct effectors and feedback pathways, thereby maintaining cAMP and cGMP levels within optimum ranges for responsiveness to signals. The ability of extracellular signals to modulate the intracellular concentration of cyclic nucleotides allows cells to respond to external stimuli across the cell membrane.

The cyclic nucleotide signaling cascades have been adapted to respond to a host of transduction systems, including G-protein coupled receptors (GPCRs) and voltage and ligand gated ion channels. Cyclic nucleotides transmit their signals in the cell through a variety of tertiary elements. The best described are cAMP dependent protein kinase (PKA) and cGMP dependent protein kinase (PKG). Cyclic nucleotide binding to the respective kinases enables the phosphorylation of downstream enzymes and proteins functioning as effectors or additional elements in the signaling cascade. Among the processes involved in memory formation is cAMP activation of PKA, which can phosphorylate cAMP response element-binding protein (CREB). Phosphorylated CREB is an activated transcription factor that binds to specific DNA loci and initiates transcription of multiple genes involved in neuronal plasticity. Both in vitro and in vivo studies have associated alterations in cyclic nucleotide concentrations with biochemical and physiological process linked to cognitive function (Kelly and Brandon, *Progress in Brain Research* 2009, 179, 67-73; Schmidt, *Current Topics in Medicinal Chemistry* 2010, 10, 222-230).

Signal intensity and the levels of coincident activity at a synapse are established variables that can result in potentiation of transmission at a particular synapse. Long term potentiation (LTP) is the best described of these processes and is known to be modulated by both the CAMP and cGMP signaling cascades. PDE2 inhibitors can enhance long term potentiation of synaptic transmission and can improve memory acquisition and consolidation in rodent models. PDE2 inhibitors have shown activity in forced swim test and light/dark box models, have demonstrated anxiolytic-like effects in elevated plus-maze, hole-board and open-field tests, and can prevent stress-induced changes in apoptosis and behavior (Boess et al., *Neuropharmacology* 2004, 47, 1081-92; Masood et al., *J. Pharmacol. Exp. Ther.* 2009, 331, 690-699). Additionally, a selective PDE2 inhibitor appears efficacious in the novel object recognition test, the social recognition test and the T-maze, an animal model of working memory (Rutten et al., *Eur. J. Neurosci.* 2007, 558, 107-112). Moreover, PDE2 inhibitors appear beneficial in reducing oxidative stress-induced anxiety, supporting their use in treating anxiety in psychiatric disorders and neurodegenerative disorders that involve oxidative stress, such as Alzheimer's disease, Parkinson's disease and multiple sclerosis (Masood et al., *J. Pharmacol. Exp. Ther.* 2008, 326, 369-379).

Such observations highlight the interest in inhibiting PDEs, including PDE2, as a therapeutic target for numerous disorders and in cognitive enhancement.

However, there remains a need for effective PDE2 inhibitors with desirable pharmaceutical properties, such as those pertaining to potency, exposure, selectivity, and side effect profile. The present invention addresses these and other needs in the art by disclosing pyrazolopyrimidinone compounds as potent, selective, and well-tolerated PDE2 inhibitors.

SUMMARY

The present disclosure relates to pyrazolopyrimidinone chemical entities, compositions including such entities, and their use in various methods and in the treatment of central nervous system and peripheral disorders associated with phosphodiesterase 2 (PDE2).

In some embodiments, the disclosure provides a chemical entity of Formula (I):

(I)

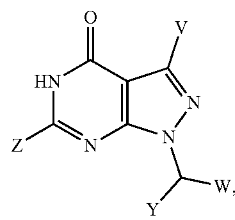

wherein V, W, Y, and Z have any of the values described herein.

In some embodiments, the disclosure provides a chemical entity of Formula (Ia) or Formula (Ib):

(Ia)

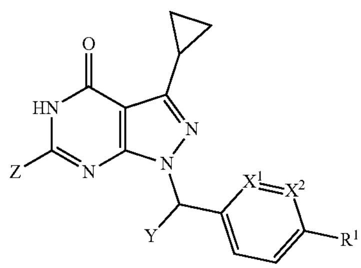

(Ib)

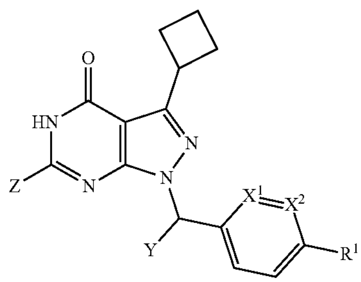

wherein $R^1$, $X^1$, $X^2$, Y and Z have any of the values described herein.

In some embodiments, the chemical entity is selected from the group consisting of compounds of Formula (I) and all pharmaceutically acceptable forms thereof, including pharmaceutically acceptable salts of compounds of Formula (I), tautomers of compounds of Formula (I), pharmaceutically acceptable prodrugs of compounds of Formula (I), and pharmaceutically active metabolites of compounds of Formula (I). More particularly, the chemical entity is selected from the group consisting of compounds of Formula (I) and pharmaceutically acceptable salts thereof.

In certain embodiments, the chemical entity is selected from any of the species described or exemplified in the disclosure herein, and more particularly, is a compound, or pharmaceutically acceptable salt thereof.

Chemical entities of Formula (I), and compositions including such entities, are useful in a wide range of methods, as described herein. In some embodiments, isotopically-labeled compounds and prodrugs can be used in metabolic and reaction kinetic studies, detection and imaging techniques and radioactive treatments. In some embodiments, the chemical entities can be used to inhibit PDE2; to treat a disorder mediated by PDE2; to enhance neuronal plasticity; to treat neurological disorders, including neurodegenerative disorders, cognitive disorders, and cognitive and motor deficits associated with CNS disorders; and to treat peripheral disorders, as disclosed herein. In some aspects, the chemical entities of the present disclosure are useful as augmenting agents to enhance the efficiency of cognitive and motor training, including in stroke or TBI rehabilitation; to facilitate neurorecovery and neurorehabilitation; and to increase the efficiency of non-human animal training protocols.

The invention is further directed to the general and specific embodiments defined, respectively, by the independent and dependent claims appended hereto, which are incorporated by reference herein. Additional embodiments, features, and advantages of the disclosure will be apparent from the following detailed description and through practice of the exemplary embodiments.

DETAILED DESCRIPTION

The embodiments may be more fully appreciated by reference to the following description, including the examples. Unless otherwise defined, all technical and scientific terms used herein have the same meaning as commonly understood by one of ordinary skill in the art. Although methods and materials similar or equivalent to those described herein can be used in the practice or testing of the present embodiments, suitable methods and materials are described herein. In addition, the materials, methods, and examples are illustrative only and not intended to be limiting.

For the sake of brevity, all publications, including patent applications, patents, and other citations mentioned herein, are incorporated by reference in their entirety. Citation of any such publication, however, shall not be construed as an admission that it is prior art to the present embodiments.

Terms and Definitions

The use of headings and subheadings provided in the sections of this specification is solely for convenience of reference and does not limit the various embodiments herein, which are to be construed by reference to the specification as a whole.

General

As used herein, the term “about” or “approximately” means within an acceptable range for a particular value as determined by one skilled in the art, and may depend in part on how the value is measured or determined, e.g., the limitations of the measurement system or technique. For example, “about” can mean a range of up to 20%, up to 10%, up to 5%, or up to 1% or less on either side of a given value. Alternatively, with respect to biological systems or processes, the term “about” can mean within an order of magnitude, within 5-fold, or within 2-fold on either side of a value. Numerical quantities given herein are approximate unless stated otherwise, meaning that the term “about” or “approximately” can be inferred when not expressly stated.

To provide a more concise description, some of the quantitative expressions given herein are not qualified with the term “about”. It is understood that, whether the term “about” is used explicitly or not, every quantity given herein is meant to refer to the actual given value, and it is also meant to refer to the approximation of such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity for which that could be obtained under the particular stoichiometric conditions. Concentrations that are given as percentages refer to mass ratios, unless indicated differently.

As used herein, the terms “a,” “an,” and “the” are to be understood as meaning both singular and plural, unless explicitly stated otherwise. Thus, “a,” “an,” and “the” (and grammatical variations thereof where appropriate) refer to one or more.

Furthermore, although items, elements or components of the embodiments may be described or claimed in the singular, the plural is contemplated to be within the scope thereof, unless limitation to the singular is explicitly stated.

The terms “comprising” and “including” are used herein in their open, non-limiting sense. Other terms and phrases used in this document, and variations thereof, unless otherwise expressly stated, should be construed as open ended, as opposed to limiting. Thus, the term “example” is used to provide exemplary instances of the item in discussion, not an exhaustive or limiting list thereof. Similarly, adjectives such as “conventional,” “traditional,” “normal,” “criterion,” “known,” and terms of similar meaning should not be construed as limiting the item described to a given time period or to an item available as of a given time, but instead should be read to encompass conventional, traditional, normal, or criterion technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as “one or more,” “at least,” “but not limited to,” or other like phrases in some instances should not be read to mean that the narrower case is intended or required in instances where such broadening phrases may be absent. As will become apparent to one of ordinary skill in the art after reading this document, the illustrated embodiments and their various alternatives may be implemented without confinement to the illustrated examples.

Chemical Terms

The term “alkyl” refers to a fully saturated aliphatic hydrocarbon group. The alkyl moiety may be a straight- or branched-chain alkyl group having from 1 to 12 carbon atoms in the chain. Examples of alkyl groups include, but are not limited to, methyl (Me, which also may be structurally depicted by the symbol, “—”), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. Alkyl groups may be optionally substituted with one or more substituents including, but not limited to, hydroxyl, alkoxy, thioalkoxy, amino, and aminoalkyl.

The term “haloalkyl” refers to a straight- or branched-chain alkyl group having from 1 to 12 carbon atoms in the chain, substituting one or more hydrogens with halogens. Examples of haloalkyl groups include, but are not limited to, $—CF_3$, $—CHF_2$, $—CH_2F$, $—CH_2CF_3$, $—CH_2CHF_2$, $—CH_2CH_2F$, $—CH_2CH_2Cl$, $—CH_2CF_2CF_3$ and other groups that in light of the ordinary skill in the art and the teachings provided herein, would be considered equivalent to any one of the foregoing examples.

The term “alkoxy” includes a straight chain or branched alkyl group with an oxygen atom linking the alkyl group to the rest of the molecule. Alkoxy includes methoxy, ethoxy, propoxy, isopropoxy, butoxy, t-butoxy, pentoxy and so on. “Aminoalkyl,” “thioalkyl,” and “sulfonylalkyl” are analogous to alkoxy, replacing the terminal oxygen atom of alkoxy with, respectively, NH (or NR), S, and $SO_2$, wherein R is an alkyl, cycloalkyl, aryl, heterocycloalkyl or heteroaryl group, as defined herein.

The term “cyano” refers to the group —CN.

The term “aryl” refers to a monocyclic, or fused or spiro polycyclic, aromatic carbocycle (ring structure having ring atoms that are all carbon), having from 3 to 12 ring atoms per ring (carbon atoms in aryl groups are sp2 hybridized), such as

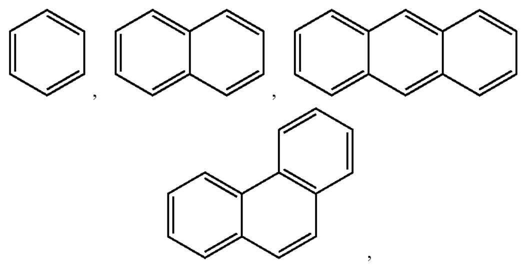

and the like.

The term “phenyl” represents the following moiety:

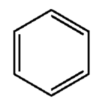

The term “cycloalkyl” refers to a saturated or partially saturated carbocycle, such as monocyclic, fused polycyclic, bridged monocyclic, bridged polycyclic, spirocyclic, or spiro polycyclic carbocycle having from 3 to 12 ring atoms per carbocycle. Where the term cycloalkyl is qualified by a specific characterization, such as monocyclic, fused polycyclic, bridged polycyclic, spirocyclic, and spiro polycyclic, then such term cycloalkyl refers only to the carbocycle so characterized. Illustrative examples of cycloalkyl groups include the following entities, in the form of properly bonded moieties:

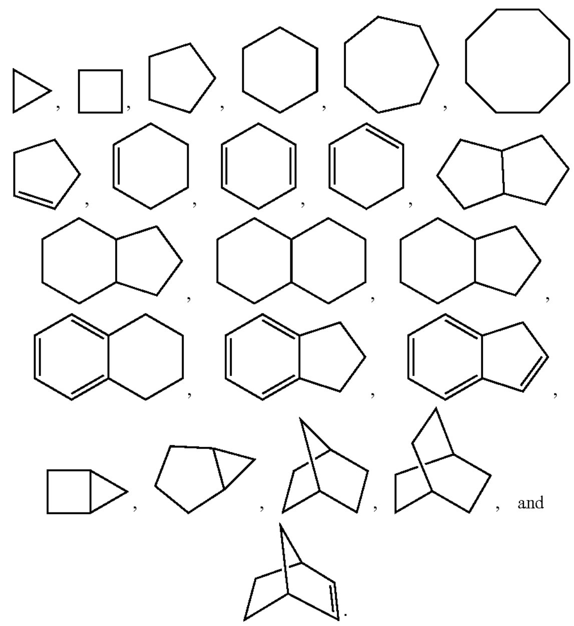

A “heterocycloalkyl” refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative entities, in the form of properly bonded moieties, include:

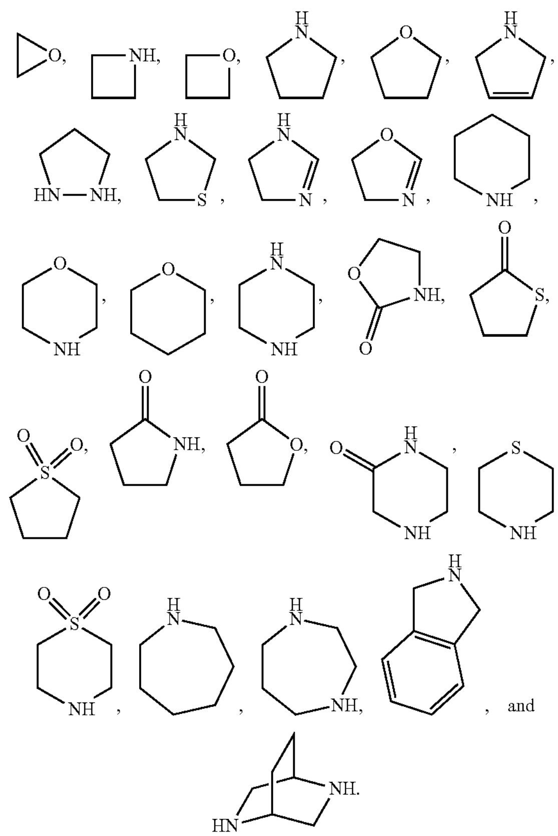

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

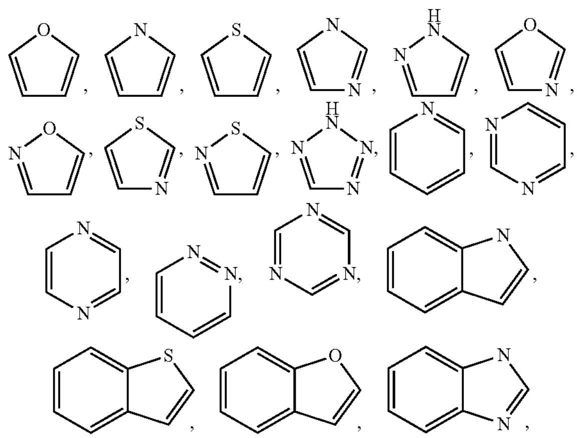

-continued

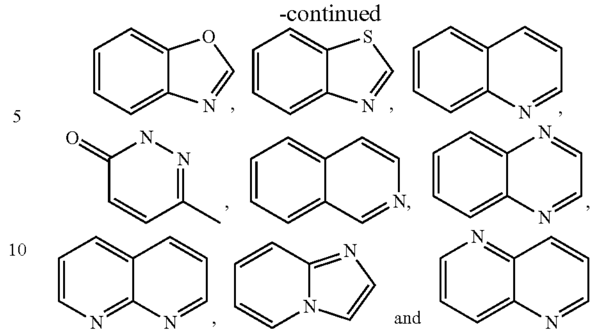

Those skilled in the art will recognize that the species of cycloalkyl, heterocycloalkyl, aryl, and heteroaryl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "heteroatom" used herein refers to, for example, O (oxygen), S (sulfur), or N (nitrogen).

By "optional" or "optionally" is meant that the subsequently described event or circumstance may or may not occur, and that the description includes instances where the event or circumstance occurs and instances or circumstances where it does not. For example, "optionally substituted alkyl" encompasses both "unsubstituted alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

The term "substituted" used herein means that any one or more hydrogens on the designated atom or group is replaced with a selection from the indicated group, provided that the designated atom's normal valence is not exceeded. When a substituent is oxo (i.e., =O) then 2 hydrogens on the atom are replaced.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$) alkyl (i.e., ether), aryloxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclyloxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), sulfhydryl (mercapto), halo($C_1$-$C_6$)alkyl (e.g., —$CF_3$), halo($C_1$-$C_6$)alkoxy (e.g., —$OCF_3$), $C_1$-$C_6$ alkylthio, arylthio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (═O). Wherever a group is described as "optionally substituted" that group can be substituted with the above substituents.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

As used herein, "tautomer" refers to the migration of protons between adjacent single and double bonds. The tautomerization process is reversible. Compounds described herein can undergo any possible tautomerization that is within the physical characteristics of the compound. The following is an example tautomerization that can occur in compounds described herein:

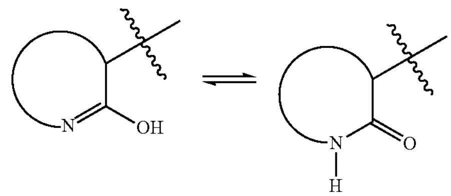

The symbols  and  are used as meaning the same spatial arrangement in chemical structures shown herein. Analogously, the symbols  and  are used as meaning the same spatial arrangement in chemical structures shown herein.

The term "chiral" refers to molecules, which have the property of non-superimposability of the mirror image partner.

"Stereoisomers" are compounds, which have identical chemical constitution, but differ with regard to the arrangement of the atoms or groups in space.

A "diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

"Enantiomers" refer to two stereoisomers of a compound, which are non-superimposable mirror images of one another. A 50:50 mixture of enantiomers is referred to as a racemic mixture or a racemate, which may occur where there has been no stereoselection or stereospecificity in a chemical reaction or process.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

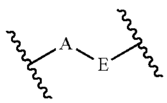

includes the substituent being oriented such that the A is attached at the leftmost attachment point of the molecule as well as the case in which A is attached at the rightmost attachment point of the molecule.

Chemical Entities

Chemical entities of the present embodiments include, but are not limited to, compounds of Formula (I) and all pharmaceutically acceptable forms thereof. Pharmaceutically acceptable forms of the compounds recited herein include pharmaceutically acceptable chelates, solvates, conformers, crystalline forms/polymorphs, salts, prodrugs, pharmaceutically active metabolites, and mixtures thereof. In certain embodiments, the compounds described herein are in the form of pharmaceutically acceptable salts. Hence, the terms "chemical entity" and "chemical entities" also encompass pharmaceutically acceptable chelates, solvates, conformers, crystalline forms/polymorphs, salts, prodrugs, pharmaceutically active metabolites, and mixtures.

The term "pharmaceutically acceptable," as used in connection with compositions of the embodiments, refers to molecular entities and other ingredients of such compositions that are physiologically tolerable and do not typically produce untoward reactions when administered to an animal (e.g., human). The term "pharmaceutically acceptable" may also mean approved by a regulatory agency of the Federal or a state government or listed in the U.S. Pharmacopeia or other generally recognized pharmacopeia for use in animals (e.g. mammals), and more particularly in humans.

Chelates

The term "chelate" refers to the chemical entity formed by the coordination of a compound to a metal ion at two (or more) points.

Solvates

Additionally, any formula given herein is intended to refer also to hydrates, solvates, and polymorphs of such compounds, and mixtures thereof, even if such forms are not listed explicitly. Some embodiments provide a solvate of a compound of Formula (I), and the use of such solvates in methods described herein. Certain compounds of Formula (I) or pharmaceutically acceptable salts of compounds of Formula (I) may be obtained as solvates. In some embodiments, the solvent is water and the solvates are hydrates.

More particularly, solvates include those formed from the interaction or complexes of compounds of the embodiments with one or more solvents, either in solution or as a solid or crystalline form. Such solvent molecules are those commonly used in the pharmaceutical art, which are known to be innocuous to the recipient, e.g., water, ethanol, ethylene glycol, and the like. Other solvents may be used as intermediate solvates in the preparation of more desirable solvates, such as MeOH, methyl t-butyl ether, EtOAc, mEtOAc, (S)-propylene glycol, (R)-propylene glycol, 1,4-butyne-diol, and the like. Hydrates include compounds formed by an incorporation of one or more water molecules.

Conformers and Crystalline Forms/Polymorphs

Some embodiments provide conformer and crystalline forms of a compound of Formula (I), and the use of these entities in methods of present disclosure. A conformer is a structure that is a conformational isomer.

Conformational isomerism is the phenomenon of molecules with the same structural formula but different conformations (conformers) of atoms about a rotating bond.

A polymorph is a composition having the same chemical formula, but a different solid state or crystal structure. In certain embodiments, compounds of Formula (I) are obtained in crystalline form. In addition, certain crystalline forms of compounds of Formula (I) or pharmaceutically acceptable salts of compounds of Formula (I) may be obtained as co-crystals. In still other embodiments, compounds of Formula (I) may be obtained in one of several polymorphic forms, as a mixture of crystalline forms, as a polymorphic form, or as an amorphous form.

As used herein, a "compound" refers to any one of: (a) the actually recited form of such compound; and (b) any of the forms of such compound in the medium in which the compound is being considered when named. For example, reference herein to a compound such as R—COOH encompasses reference to any one of, for example, R—COOH(s), R—COOH(sol), and R—COO-(sol). In this example, R—COOH(s) refers to the solid compound, as it could be for example in a tablet or some other solid pharmaceutical composition or preparation; R—COOH(sol) refers to the undissociated form of the compound in a solvent; and R—COO-(sol) refers to the dissociated form of the compound in a solvent, such as the dissociated form of the compound in an aqueous environment, whether such dissociated form derives from R—COOH, from a salt thereof, or from any other entity that yields R—COO-upon dissociation in the medium being considered.

In another example, an expression such as "exposing an entity to a compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in its chemically relevant form (or forms) that exists in the medium in which such reacting takes place, with (b) the chemically relevant form (or forms) of the compound R—COOH that exists in the medium in which such reacting takes place. In this regard, if such entity is, for example, in an aqueous environment, it is understood that the compound R—COOH is in the same such medium, and therefore the entity is being exposed to species such as R—COOH(aq) and/or R—COO-(aq), where the subscript "(aq)" stands for "aqueous" according to its conventional meaning in chemistry and biochemistry. A carboxylic acid functional group has been chosen in these nomenclature examples; this choice is not intended, however, as a limitation but is merely an illustration. It is understood that analogous examples can be provided in terms of other functional groups, including, but not limited to, hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation and deprotonation. No further examples in this regard are provided herein because these interactions and transformations in a given medium are known by any one of ordinary skill in the art.

In another example, a "zwitterionic" compound is encompassed herein by referring to a compound that may form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Interest (ChEBI) dictionary of molecular entities. As is generally well known, a zwitterion or zwitterionic compound is a neutral compound that has formal unit charges of opposite sign. Sometimes these compounds are referred to by the term "inner salts".

Salts

Embodiments include pharmaceutically acceptable salts of the compounds represented by Formula (I), and methods using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally, G. S. Paulekuhn et al., Trends in Active Pharmaceutical Ingredient Salt Selection based on Analysis of the Orange Book Database, *J. Med. Chem.* 2007, 50, 6665-6672; Berge et al., Pharmaceutical Salts, *J. Pharm. Sci.* 1977, 66, 1-19; Stahl and Wermuth (eds), Pharmaceutical Salts; Properties, Selection, and Use: 2nd Revised Edition, Wiley-VCS, Zurich, Switzerland (2011). Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form pharmaceutically acceptable salt bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, borate, nitrate, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, y-hydroxybutyrates, glycolates, tartrates, methanesulfonates, propanesulfonates, naphthalene-1-sulfonates, naphthalene-2-sulfonates, besylate, mesylate and mandelates.

When the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-O-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

Prodrugs

Some embodiments provide prodrugs of the compounds of Formula (I), and the use of such pharmaceutically acceptable prodrugs in methods of the present disclosure, particularly therapeutic methods.

A "prodrug" is a drug precursor that is initially inactive or partially active and upon administration in vivo undergoes chemical conversion by metabolic processes into an active pharmacological agent. A "pharmaceutically acceptable prodrug" is a prodrug that is preferably non-toxic, biologically tolerable, and otherwise biologically suitable for administration to the subject. Prodrugs are often useful because, in some situations, they can be easier to administer than the parent drug. They can, for instance, be bioavailable by oral administration whereas the parent is not. The prodrug can also have improved solubility in pharmaceutical compositions over the parent drug.

Prodrugs may be determined using routine techniques known or available in the art (e.g., Bundgard (ed.), 1985, Design of prodrugs, Elsevier; Krogsgaard-Larsen et al., (eds.), 1991, Design and Application of Prodrugs, Harwood Academic Publishers). Prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters include $C_{1-6}$alkyl, $C_{1-6}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130.

Tautomers

Some embodiments provide tautomers of compounds of Formula (I), as defined further herein, which may also be used in the methods of the disclosure.

Metabolites

Some embodiments provide pharmaceutically active metabolites of the compounds of Formula (I), which may also be used in the methods of the disclosure. A "pharmaceutically active metabolite" means a pharmacologically active product of metabolism in the body of a compound of Formula (I) or salt thereof.

Prodrugs and active metabolites of a compound may be determined using routine techniques known or available in the art. For example, isolated metabolites can be enzymatically and synthetically produced (e.g., Bertolini et al., *J. Med. Chem.* 1997, 40, 2011-2016; Shan et al., *J. Pharm. Sci.* 1997, 86, 765-767; Bagshawe, *Drug Dev. Res.* 1995, 34, 220-230; and Bodor, *Adv Drug Res.* 1984, 13, 224-231).

Isotopes

Isotopes may be present in the compounds described. Each chemical element present in a compound either specifically or generically described herein may include any isotope of the element. Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the embodiments include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively.

Compositions

The term "composition," as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present embodiments encompass any composition made by admixing a chemical entity of Formula (I) and a pharmaceutically acceptable excipient. More particularly, the chemical entity of Formula (I) is a compound of Formula (I) or a pharmaceutically acceptable salt of a compound of Formula (I).

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluents to facilitate administration of an agent and that is compatible therewith. Examples of excipients include calcium carbonate, calcium phosphate, various sugars and types of starch, modified cellulose, gelatin, vegetable oils, and polyethylene glycols. Suitable pharmaceutical carriers include those described in Remington: The Science and Practice of Pharmacy, $21^{st}$ Ed., Lippincott Williams & Wilkins (2005).

The term "carrier" refers to an adjuvant, vehicle, or excipients, with which the compound is administered. In preferred embodiments, the carrier is a solid carrier. Suitable pharmaceutical carriers include those described in Remington: The Science and Practice of Pharmacy, $21^{st}$ Ed., Lippincott Williams & Wilkins (2005).

The term "dosage form," as used herein, is the form in which the dose is to be administered to the subject or patient. The drug is generally administered as part of a formulation that includes nonmedical agents. The dosage form has unique physical and pharmaceutical characteristics. Dosage forms, for example, may be solid, liquid or gaseous. "Dosage forms" may include for example, a capsule, tablet, caplet, gel caplet (gelcap), syrup, a liquid composition, a powder, a concentrated powder, a concentrated powder admixed with a liquid, a chewable form, a swallowable form, a dissolvable form, an effervescent, a granulated form, and an oral liquid solution. In a specific embodiment, the dosage form is a solid dosage form, and more specifically, comprises a tablet or capsule.

As used herein, the term "inert" refers to any inactive ingredient of a described composition. The definition of "inactive ingredient" as used herein follows that of the U.S. Food and Drug Administration, as defined in 21 C.F.R. 201.3(b)(8), which is any component of a drug product other than the active ingredient.

As used herein, "suitable for oral administration" refers to a sterile, pharmaceutical product produced under good manufacturing practices (GMP) that is prepared and presented in a manner such that the composition not likely to cause any untoward or deleterious effects when orally administered to a subject. Unless specified otherwise, all of the compositions disclosed herein are suitable for oral administration.

Methods and Uses

As used herein, the term "disorder" is used interchangeably with "disease" or "condition". For example, a CNS disorder also means a CNS disease or a CNS condition.

As used herein, the term "cognitive impairment" is used interchangeably with "cognitive dysfunction" or "cognitive deficit," all of which are deemed to cover the same therapeutic indications.

The terms "treating," "treatment," and "treat" cover therapeutic methods directed to a disease-state in a subject and include: (i) preventing the disease-state from occurring, in particular, when the subject is predisposed to the disease-state but has not yet been diagnosed as having it; (ii) inhibiting the disease-state, e.g., arresting its development (progression) or delaying its onset; and (iii) relieving the disease-state, e.g., causing regression of the disease state until a desired endpoint is reached. Treating also includes ameliorating a symptom of a disease (e.g., reducing the pain, discomfort, or deficit), wherein such amelioration may be directly affecting the disease (e.g., affecting the disease's cause, transmission, or expression) or not directly affecting the disease.

As used in the present disclosure, the term "effective amount" is interchangeable with "therapeutically effective amount" and means an amount or dose of a compound or composition effective in treating the particular disease, condition, or disorder disclosed herein, and thus "treating" includes producing a desired preventative, inhibitory, relieving, or ameliorative effect. In methods of treatment according to the embodiments, "an effective amount" of at least one compound according to the embodiments is administered to a subject (e.g., a mammal). An "effective amount" also means an amount or dose of a compound or composition effective to modulate activity of PDE2 or an associated signaling pathway. The "effective amount" will vary, depending on the compound, the disease, the type of treatment desired, and its severity, and age, weight, etc.

The term "animal" is interchangeable with "subject" and may be a vertebrate, in particular, a mammal, and more particularly, a human, and includes a laboratory animal in the context of a clinical trial or screening or activity experiment. Thus, as can be readily understood by one of ordinary skill in the art, the compositions and methods of the present embodiments are particularly suited to administration to any vertebrate, particularly a mammal, and more particularly, a human.

As used herein, a "control animal" or a "normal animal" is an animal that is of the same species as, and otherwise comparable to (e.g., similar age, sex), the animal that is trained under conditions sufficient to induce transcription-dependent memory formation in that animal.

By "enhance," "enhancing," or "enhancement" is meant the ability to potentiate, increase, improve or make greater or better, relative to normal, a biochemical or physiological action or effect. For example, enhancing long term memory formation refers to the ability to potentiate or increase long term memory formation in an animal relative to the normal long term memory formation of the animal or controls. As a result, long term memory acquisition is faster or better retained. Enhancing performance of a cognitive task refers to the ability to potentiate or improve performance of a specified cognitive task by an animal relative to the normal performance of the cognitive task by the animal or controls.

As used herein, the term "training protocol," or "training," refers to either "cognitive training" or "motor training."

Reference will now be made to the embodiments of the present disclosure, examples of which are illustrated by and described in conjunction with the accompanying drawings and examples. While certain embodiments are described herein, it is understood that the described embodiments are not intended to limit the scope of the invention. On the contrary, the present disclosure is intended to cover alternatives, modifications, and equivalents that can be included within the invention as defined by the appended claims.

Chemical Entities

Some embodiments provide certain substituted pyrazolopyrimidinone chemical entities, which are useful, for example, as inhibitors of PDE2 enzymatic activity.

Some embodiments provide a chemical entity of Formula (I):

(I)

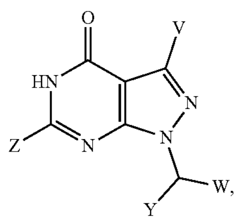

wherein V, W, Y, and Z have any of the values described herein.

In some embodiments, the present invention is directed to a pyrazolopyrimidinone compound of Formula (I):

(I)

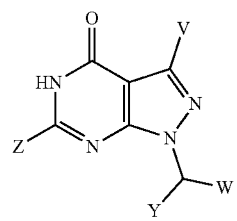

or a pharmaceutically acceptable salt, tautomer, pharmaceutically acceptable prodrug or pharmaceutically active metabolite thereof, wherein:

V is —$C_{3-8}$cycloalkyl, optionally substituted with up to 4 members independently selected from the group consisting of: -fluoro, —$C_{1-4}$alkyl, and —$C_{1-4}$alkoxy;

W is -aryl or -pyridyl, both optionally substituted with up to 3 members, each independently selected from the group consisting of: -halo, —$C_{1-6}$alkyl, —$C_{1-6}$haloalkyl, —$C_{1-6}$alkoxy, —$C_{1-6}$haloalkoxy, and —$C_3$-5cycloalkyl;

Y is —$C_{1-6}$alkyl; and

Z is —$C_{1-6}$alkyl, —$C_{1-6}$haloalkyl, —$C_{1-6}$alkoxy, —$(CH_2)_n$aryl, or —$(CH_2)_n$heteroaryl, said aryl and heteroaryl optionally substituted with up to 3 members, each independently selected from the group consisting of: -halo, —OH, —CN, —$CH_2OCH_3$, —$CH_2CH_2OCH_3$, —$N(CH_3)_2$, —$C_{1-6}$alkyl, —$C_{1-6}$haloalkyl, —$C_{1-6}$alkoxy, —$C_{1-6}$haloalkoxy, and —$C_{3-5}$cycloalkyl, and said alkyl and haloalkyl optionally substituted with up to 3 members, each independently selected from the group consisting of: -halo, —OH, —CN, —$CH_2OCH_3$, —$CH_2CH_2OCH_3$, —$N(CH_3)_2$, —$C_{1-6}$alkoxy, —$C_{1-6}$haloalkoxy, and —$C_{3-5}$cycloalkyl, where n is 1 or 2.

In some embodiments, the present invention is directed to a pyrazolopyrimidinone compound of Formula (I):

(I)

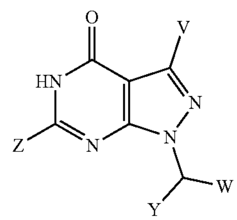

or a pharmaceutically acceptable salt, tautomer, pharmaceutically acceptable prodrug or pharmaceutically active metabolite thereof, wherein:

V is —$C_{3-4}$cycloalkyl;

W is -aryl or -pyridyl, both optionally substituted with up to 3 members, each independently selected from the group consisting of: -halo, —$C_{1-6}$alkyl, —$C_{1-6}$haloalkyl, —$C_{1-6}$alkoxy, —$C_{1-6}$haloalkoxy, and —$C_{3-5}$cycloalkyl;

Y is —$C_{1-4}$alkyl; and

Z is $—C_{1-6}$alkyl, $—C_{1-6}$haloalkyl, $—C_{1-6}$alkoxy, $—(CH_2)_n$aryl, or $—(CH_2)_n$heteroaryl, said aryl and heteroaryl optionally substituted with up to 3 members, each independently selected from the group consisting of: -halo, —OH, —CN, $—CH_2OCH_3$, $—CH_2CH_2OCH_3$, $—N(CH_3)_2$, $—C_{1-6}$alkyl, $—C_{1-6}$haloalkyl, $—C_{1-6}$alkoxy, $—C_{1-6}$haloalkoxy, and $—C_{3-5}$cycloalkyl, and said alkyl and haloalkyl optionally substituted with up to 3 members, each independently selected from the group consisting of: -halo, —OH, —CN, $—CH_2OCH_3$, $—CH_2CH_2OCH_3$, $—N(CH_3)_2$, $—C_{1-6}$alkoxy, $—C_{1-6}$haloalkoxy, and $—C_{3-5}$cycloalkyl, where n is 1 or 2.

In some embodiments of Formula (I), V is $—C_{3-8}$cycloalkyl, optionally substituted with up to 4 members independently chosen from the group consisting of: -fluoro, $—C_{1-4}$alkyl, $—C_{1-4}$alkoxy.

In some embodiments, V is -cyclopropyl or -cyclobutyl.

In some embodiments, V is -cyclopropyl.

In some embodiments, W is -aryl or -pyridyl, both optionally substituted with up to 3 members, each independently selected from the group consisting of: -halo, $—C_{1-6}$alkyl, $—C_{1-6}$haloalkyl, $—C_{1-6}$alkoxy, $—C_{1-6}$haloalkoxy, and $—C_{3-5}$cycloalkyl.

In some embodiments, W is -phenyl, optionally substituted with up to 3 members, each independently selected from the group consisting of: —F, —Cl, —Br, $—CH_3$, $—CH_2CH_3$, $—CHF_2$, $—CF_3$, $—OCH_3$, $—OCF_3$, and -cyclopropyl.

In some embodiments, W is -phenyl, substituted with —F or $—CF_3$.

In some embodiments, W is -pyridyl, optionally substituted with up to 3 members, each independently selected from the group consisting of: —F, —Cl, —Br, $—CH_3$, $—CH_2CH_3$, $—CHF_2$, $—CF_3$, $—OCH_3$, $—OCF_3$, and -cyclopropyl.

In some embodiments, W is -pyridyl, substituted with —F or $—CF_3$.

In some embodiments, Y is $—C_{1-6}$alkyl.

In some embodiments, Y is $—C_{1-4}$alkyl;

In some embodiments, Y is $—CH_3$ or $—CH_2CH_3$;

In some embodiments, Z is $—C_{1-6}$alkyl, $—C_{1-6}$haloalkyl, $—C_{1-6}$alkoxy, $—(CH_2)_n$aryl, or $—(CH_2)_n$heteroaryl, said aryl and heteroaryl optionally substituted with up to 3 members, each independently selected from the group consisting of: -halo, —OH, —CN, $—CH_2OCH_3$, $—CH_2CH_2OCH_3$, $—N(CH_3)_2$, $—C_{1-6}$alkyl, $—C_{1-6}$haloalkyl, $—C_{1-6}$alkoxy, $—C_{1-6}$haloalkoxy, and $—C_{3-5}$cycloalkyl, and said alkyl and haloalkyl optionally substituted with up to 3 members, each independently selected from the group consisting of: -halo, —OH, —CN, $—CH_2OCH_3$, $—CH_2CH_2OCH_3$, $—N(CH_3)_2$, $—C_{1-6}$alkoxy, $—C_{1-6}$haloalkoxy, and $—C_{3-5}$cycloalkyl, where n is 1 or 2.

In some embodiments, Z is $—CH_3$ and $—CH_2CH_3$.

In some embodiments, Z is $—CH_3$.

In some embodiments, Z is $—(CH_2)_n$pyridyl, $—(CH_2)_n$pyrazolyl, $—(CH_2)_n$isoxazole, $—(CH_2)_n$oxazole, $—(CH_2)_n$oxadiazole, $—(CH_2)_n$triazole, $—(CH_2)_n$thiazole, $—(CH_2)_n$pyrimidine, or $—(CH_2)_n$tetrahydropyranyl, said pyridyl, pyrazolyl, isoxazole, oxazole, oxadiazole, triazole, thiazole, pyrimidine and tetrahydropyran all optionally substituted with up to 3 members, each independently selected from the group consisting of: —F, —Cl, —Br, $—CH_3$, $—CH_2CH_3$, isopropyl, -tert-butyl, -cyclopropyl, $—CF_3$, $—CH_2CF_3$, —OH, $—OCH_3$, $—OCF_3$, $—CH_2OCH_3$, $—CH_2CH_2OCH_3$, —CN, $—N(CH_3)_2$, $—CH_2N(CH_3)_2$, and -phenyl; where n is 1 or 2.

In certain embodiments of Formula (I), V is -cyclopropyl or -cyclobutyl and Z is $—CH_3$.

In certain embodiments of Formula (I), V is -cyclopropyl and Z is $—CH_3$.

In certain embodiments of Formula (I), V is -cyclopropyl or -cyclobutyl and Y is $—CH_3$ or $—CH_2CH_3$.

In certain embodiments of Formula (I), V is -cyclopropyl and Y is $—CH_3$ or $—CH_2CH_3$.

In certain embodiments of Formula (I), V is -cyclopropyl or -cyclobutyl and W is -phenyl or -pyridyl, each optionally substituted with —F or $—CF_3$.

In certain embodiments of Formula (I), V is -cyclopropyl and W is -pyridyl, optionally substituted with —F or $—CF_3$.

In certain embodiments, a compound, or pharmaceutically acceptable salt thereof, of Formula (I) is selected from the group consisting of:

In some embodiments, the disclosure provides compounds of Formula (I) represented by the structural Formula (Ia):

(Ia)

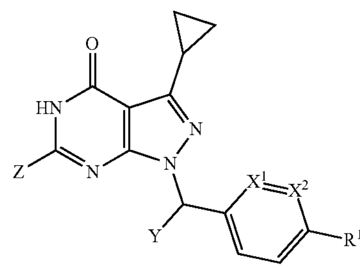

or pharmaceutically acceptable salts, tautomers, pharmaceutically acceptable prodrugs, or pharmaceutically active metabolites thereof, wherein:

$R^1$ is $—C_{1-6}$haloalkyl; and $X^1$ and $X^2$ are both CH, $X^1$ is CH and $X^2$ is N (nitrogen), or $X^1$ is N (nitrogen) and $X^2$ is CH; and Z and Y have any of the values described herein.

In some embodiments the disclosure provides compounds of Formula (I) represented by the structural Formula (Ib):

(Ib)

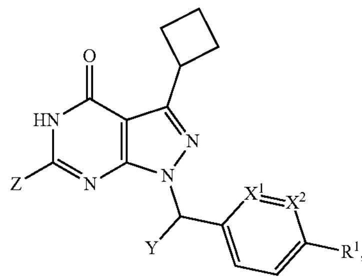

or pharmaceutically acceptable salts, tautomers, pharmaceutically acceptable prodrugs, or pharmaceutically active metabolites thereof, wherein:

$R^1$ is $—C_{1-6}$haloalkyl; and $X^1$ and $X^2$ are both CH, $X^1$ is CH and $X^2$ is N (nitrogen), or $X^1$ is N (nitrogen) and $X^2$ is CH; and Z and Y have any of the values described herein.

In certain embodiments, a compound of Formula (I) is selected from any of the examples in the following table:

| Example | Compound Name |
|---|---|
| 1 | 3-cyclopropyl-6-[(5-methoxypyridin-2-yl)methyl]-1-{1-[6-(trifluoromethyl)pyridin-3-yl]propyl}-1H,4H,5H-pyrazolo[3,4-d]pyrimidin-4-one; |
| 2 | 3-cyclopropyl-6-[(5-methoxypyridin-2-yl)methyl]-1-{1-[6-(trifluoromethyl)pyridin-3-yl]ethyl}-1H,4H,5H-pyrazolo[3,4-d]pyrimidin-4-one; |
| 3 | 3-cyclopropyl-6-methyl-1-{1-[6-(trifluoromethyl)pyridin-3-yl]propyl}-1H,4H,5H-pyrazolo[3,4-d]pyrimidin-4-one; |
| 4 | 3-cyclobutyl-6-methyl-1-{1-[6-(trifluoromethyl)pyridin-3-yl]propyl}-1H,4H,5H-pyrazolo[3,4-d]pyrimidin-4-one; |
| 5 | 3-cyclopropyl-6-[(5-methoxypyridin-2-yl)methyl]-1-[(1S)-1-[6-(trifluoromethyl)pyridin-3-yl]ethyl]-1H,4H,5H-pyrazolo[3,4-d]pyrimidin-4-one; |
| 6 | 3-cyclopropyl-6-[(5-methoxypyridin-2-yl)methyl]-1-[(1R)-1-[6-(trifluoromethyl)pyridin-3-yl]ethyl]-1H,4H,5H-pyrazolo[3,4-d]pyrimidin-4-one; |
| 7 | 3-cyclopropyl-6-[(5-fluoropyridin-2-yl)methyl]-1-{1-[6-(trifluoromethyl)pyridin-3-yl]ethyl}-1H,4H,5H-pyrazolo[3,4-d]pyrimidin-4-one; |
| 8 | 3-cyclopropyl-6-[(5-fluoropyridin-2-yl)methyl]-1-{1-[6-(trifluoromethyl)pyridin-3-yl]propyl}-1H,4H,5H-pyrazolo[3,4-d]pyrimidin-4-one; |
| 9 | 3-cyclopropyl-6-methyl-1-{1-[5-(trifluoromethyl)pyridin-2-yl]propyl}-1H,4H,5H-pyrazolo[3,4-d]pyrimidin-4-one; |
| 10 | 3-cyclopropyl-6-methyl-1-{1-[4-(trifluoromethyl)phenyl]ethyl}-1H,4H,5H-pyrazolo[3,4-d]pyrimidin-4-one; |
| 11 | 3-cyclopropyl-6-methyl-1-{1-[5-(trifluoromethyl)pyridin-2-yl]ethyl}-1H,4H,5H-pyrazolo[3,4-d]pyrimidin-4-one; |
| 12 | 3-cyclopropyl-6-methyl-1-{1-[6-(trifluoromethyl)pyridin-3-yl]ethyl}-1H,4H,5H-pyrazolo[3,4-d]pyrimidin-4-one; |
| 13 | 3-cyclopropyl-6-methyl-1-[(1S)-1-[6-(trifluoromethyl)pyridin-3-yl]ethyl]-1H,4H,5H-pyrazolo[3,4-d]pyrimidin-4-one; |
| 14 | 3-cyclopropyl-6-methyl-1-[(1R)-1-[6-(trifluoromethyl)pyridin-3-yl]ethyl]-1H,4H,5H-pyrazolo[3,4-d]pyrimidin-4-one; |
| 15 | 3-cyclopropyl-6-[(5-fluoropyridin-2-yl)methyl]-1-[(1S)-1-[6-(trifluoromethyl)pyridin-3-yl]ethyl]-1H,4H,5H-pyrazolo[3,4-d]pyrimidin-4-one; |
| 16 | 3-cyclopropyl-6-[(5-fluoropyridin-2-yl)methyl]-1-[(1R)-1-[6-(trifluoromethyl)pyridin-3-yl]ethyl]-1H,4H,5H-pyrazolo[3,4-d]pyrimidin-4-one; |
| 17 | 3-cyclopropyl-6-[(5-methoxypyridin-2-yl)methyl]-1-[(1S)-1-[6-(trifluoromethyl)pyridin-3-yl]propyl]-1H,4H,5H-pyrazolo[3,4-d]pyrimidin-4-one; |
| 18 | 3-cyclopropyl-6-[(5-methoxypyridin-2-yl)methyl]-1-[(1R)-1-[6-(trifluoromethyl)pyridin-3-yl]propyl]-1H,4H,5H-pyrazolo[3,4-d]pyrimidin-4-one; |
| 19 | 3-cyclopropyl-6-methyl-1-[(1S)-1-[6-(trifluoromethyl)pyridin-3-yl]propyl]-1H,4H,5H-pyrazolo[3,4-d]pyrimidin-4-one; |
| 20 | 3-cyclopropyl-6-methyl-1-[(1R)-1-[6-(trifluoromethyl)pyridin-3-yl]propyl]-1H,4H,5H-pyrazolo[3,4-d]pyrimidin-4-one; |
| 21 | 3-cyclopropyl-6-[(5-fluoropyridin-2-yl)methyl]-1-[(1S)-1-[6-(trifluoromethyl)pyridin-3-yl]propyl]-1H,4H,5H-pyrazolo[3,4-d]pyrimidin-4-one; |
| 22 | 3-cyclopropyl-6-[(5-fluoropyridin-2-yl)methyl]-1-[(1R)-1-[6-(trifluoromethyl)pyridin-3-yl]propyl]-1H,4H,5H-pyrazolo[3,4-d]pyrimidin-4-one; |
| 23 | 3-cyclopropyl-6-methyl-1-[(1S)-1-[5-(trifluoromethyl)pyridin-2-yl]propyl]-1H,4H,5H-pyrazolo[3,4-d]pyrimidin-4-one; |
| 24 | 3-cyclopropyl-6-methyl-1-[(1R)-1-[5-(trifluoromethyl)pyridin-2-yl]propyl]-1H,4H,5H-pyrazolo[3,4-d]pyrimidin-4-one; |
| 25 | 3-cyclopropyl-6-methyl-1-[(1S)-1-[5-(trifluoromethyl)pyridin-2-yl]ethyl]-1H,4H,5H-pyrazolo[3,4-d]pyrimidin-4-one; and |
| 26 | 3-cyclopropyl-6-methyl-1-[(1R)-1-[5-(trifluoromethyl)pyridin-2-yl]ethyl]-1H,4H,5H-pyrazolo[3,4-d]pyrimidin-4-one. |

Further embodiments are provided by pharmaceutically acceptable salts of compounds of Formula (I), tautomers of compounds of Formula (I), pharmaceutically acceptable prodrugs of compounds of Formula (I), and pharmaceutically active metabolites of compounds of Formula (I).

Isotopically-Labeled Compounds

Compounds of Formula (I) may include any isotope where one or more atoms are replaced by an atom having an atomic mass or mass number different from the atomic mass or mass number usually found in nature. For example, the isotopes may be isotopes of carbon, chlorine, fluorine, hydrogen, iodine, nitrogen, oxygen, phosphorous, sulfur, and technetium, including $^{11}C$, $^{13}C$, $^{14}C$, $^{36}Cl$, $^{18}F$, $^{2}H$, $^{3}H$, $^{123}I$, $^{125}I$, $^{13}N$, $^{15}N$, $^{15}O$, $^{17}O$, $^{18}O$, $^{31}P$, $^{32}P$, $^{35}S$, and $^{99m}Tc$.

Compounds of the present invention (and forms of such compounds, such as pharmaceutically acceptable salts and prodrugs) that contain the aforementioned isotopes or other isotopes of other atoms are within the scope of the invention. Isotopically-labeled compounds of the present embodiments are useful in drug and substrate tissue distribution and target occupancy assays. For example, isotopically labeled compounds are particularly useful in SPECT (single photon emission computed tomography) and in PET (positron emission tomography), as discussed further herein. In addition, isotopically labelled compounds are useful for improving the absorption, distribution, metabolism and/or excretion (ADME) properties of drugs. For instance, replacement of one or more hydrogen atoms with deuterium ($^{2}H$) can modify the metabolism of a drug and improve the metabolic profile by decreasing the metabolic clearance in vivo, extending the half-life, reducing $C_{max}$ or reducing levels of potentially toxic metabolites.

Compositions

In some embodiments chemical entities of Formula (I) are used, alone or in combination with one or more additional active ingredients, to formulate pharmaceutical compositions. More particularly, a pharmaceutical composition can comprise: (a) an effective amount of at least one chemical entity of Formula (I); and (b) a pharmaceutically acceptable carrier.

In some embodiments, a pharmaceutical composition comprises a compound, or pharmaceutically acceptable salt thereof, of any of the embodiments and examples disclosed herein; and a pharmaceutically acceptable carrier. In specific embodiments, a pharmaceutical composition comprises a compound of any one of preparative examples 1-43; and a pharmaceutically acceptable carrier.

In some embodiments, compounds of Formula (I), and pharmaceutically acceptable salts thereof, are used, alone or in combination with one or more additional active ingredients, to formulate pharmaceutical compositions.

Formulations and Administration

Numerous standard references are available that describe procedures for preparing various formulations suitable for administering the compounds and compositions according to the embodiments. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Osol, ed.), 1980, 1553-1593.

Any suitable route of administration may be employed for providing an animal, especially a human, with an effective dosage of a compound or composition of the present embodiments. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent, or excipient used will depend upon the means and purpose for which the compound of the present embodiments is being applied. Solvents are generally selected based on solvents recognized by persons skilled in the art as safe (GRAS) to be administered to an animal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present embodiments or pharmaceutical composition thereof) or aid in the manufacturing of the pharmaceutical product (i.e., medicament).

The formulations may be prepared using conventional dissolution and mixing procedures. For example, the bulk drug substance (i.e., a compound of the present embodiments or stabilized form of the compound (e.g., complex with a modified cyclodextrin or other known complexation agent)) is dissolved in a suitable solvent in the presence of one or more of the excipients described above. The compound of the present embodiments is typically formulated into pharmaceutical dosage forms to provide an easily controllable and appropriate dosage of the drug.

The pharmaceutical composition (or formulation) for application may be packaged in a variety of ways, depending upon the method used to administer the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Dosage Forms

The present compounds may be systemically administered, e.g., orally, in combination with a pharmaceutically acceptable vehicle such as an inert diluent or an assimilable edible carrier. Hence in some embodiments, chemical entities of the present embodiments are suitable for oral administration. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.01% of active compound. The percentage of the compositions and preparations may, of course, be varied and may conveniently be between about 0.01% to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are typically prepared by incorporating the active compound in the required amount in the appropriate solvent with a variety of the other ingredients enumerated above, as required, followed by filter sterilization. In the case of sterile powders for the preparation of sterile injectable solutions, common methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Dosages

Useful dosages of the compounds of Formula (I) can be determined by comparing their in vitro activity and in vivo activity in animal models. Methods for the extrapolation of effective dosages in mice, and other animals, to humans are known to the art. Useful dosages of the compounds of Formula (I) can be determined by comparing their in vitro activity, and in vivo activity in animal models. Methods for the extrapolation of effective dosages in mice, and other animals, to humans are known to the art (e.g., U.S. Pat. No. 4,938,949).

Optimal dosages to be administered in the therapeutic methods of the present embodiments may be determined by those skilled in the art and will depend on multiple factors, including the particular composition in use, the strength of the preparation, the mode and time of administration, and the advancement of the disease or condition. Additional factors may include characteristics on the subject being treated, such as age, weight, gender, and diet.

In general, however, a suitable dose will be in the range from about 0.01 to about 500 mg, more specifically from about 0.01 to about 100 mg (or any other value or range of values therein). In certain embodiments the pharmaceutical composition is an oral dosage form that contains from about 0.1 mg to about 1000 mg, from about 1 mg to about 500 mg, or from about 10 mg to about 200 mg of a compound of Formula (I).

In some embodiments, the active ingredient can be administered to achieve peak plasma concentrations of the active compound of from about 0.1 to about 5,000 ng/ml, preferably, about 0.1 to 100 ng/mL, and more preferably, about 0.1 to about 30 ng/mL. This may be achieved, for example, by the intravenous injection of a 0.05 to 5% solution of the active ingredient, optionally in saline, or orally administered as a bolus containing about 0.01 to 100 mg of the active ingredient. Desirable blood levels may be maintained by continuous infusion to provide about 0.001 to 5.0 mg/kg/hour or by intermittent infusions containing about 0.04 to 15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of temporally-distinct administrations used according to the compositions and methods of the present embodiments.

Effective amounts or doses of the active agents of the present disclosure may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. Such compositions and preparations should contain at least 0.01% of active compound. The percentage of the compositions and preparations may, of course, be varied and may conveniently be between 0.01 to about 60% of the weight of a given unit dosage form. The amount of active compound in such therapeutically useful composition is such that an effective dosage level will be obtained. An exemplary dose is in the range from about 0.001 to about 200 mg of active agent per day, more specifically about 0.05 to 100 mg/day, in single or divided dosage units (e.g., BID, TID, QID). For a 70-kg human, an illustrative range for a suitable dosage amount is from 0.01 to 200 mg/day, or about 0.01 to 50 mg/day.

Methods and Uses

Uses of Isotopically-Labeled Compounds

In some embodiments, the present disclosure provides methods of using isotopically labeled compounds of Formula (I) in: (i) metabolic studies (with, for example $^{14}C$), reaction kinetic studies (with, for example $^{2}H$ or $^{3}H$); (ii) detection or imaging techniques (such as positron emission tomography (PET) or single-photon emission computed tomography (SPECT)) including drug or substrate tissue distribution assays; or (iii) in radioactive treatment of patients.

Isotopically labeled compounds of Formula (I) can generally be prepared by carrying out the procedures disclosed in the schemes or in the examples and preparations described below by substituting a readily available isotopically labeled reagent for a non-isotopically labeled reagent. Compounds labeled with $^{18}F$ or $^{11}C$ may be particularly preferred for PET, and $^{123}I$ labeled compounds may be particularly preferred for SPECT studies.

Further substitution of compounds of Formula (I) with heavier isotopes such as deuterium (i.e., $^{2}H$) may afford certain therapeutic advantages resulting from greater metabolic stability, for example increased in vivo half-life or reduced dosage requirements.

Therapeutic Methods

Chemical entities, and compositions thereof, of the present disclosure are useful in various therapeutic methods (or in the manufacture of a medicament for use in such methods), as disclosed further herein. In a specific aspect, the chemical entity is a compound of Formula (I) or a pharmaceutically acceptable salt thereof.

In some embodiments, chemical entities of the present disclosure are useful in methods of treating a subject suffering from or diagnosed with a disorder mediated by PDE2 activity, comprising administering to a subject in need thereof an effective amount of a chemical entity of any one of the embodiments herein. In one aspect, the subject is diagnosed with a disorder mediated by PDE2 activity. In another aspect, the subject is suffering from a disorder mediated by PDE2 activity.

In some embodiments, chemical entities of the present disclosure are useful in enhancing neuronal plasticity, an essential property of the brain that can be impaired in numerous CNS disorders and augmented in healthy animals. Without being limited by mechanism, such chemical entities can enhance cyclic adenosine monophosphate (cAMP) response element binding protein (CREB) pathway function in cells, modulating transcription of multiple genes involved in synaptic plasticity (see, e.g., Tully et al., *Nat. Rev. Drug Discov.* 2003, 2, 267-277; Alberini, *Physiol. Rev.* 2009, 89, 121-145). As PDE2 is a dual specificity phosphodiesterase, chemical entities of Formula (I) may also impact neuronal plasticity by modulating and integrating cAMP and cGMP signaling pathways, both of which have been shown to affect memory. See, e.g., Gomez and Breitenbucher, *Bioorg, Med. Chem Lett.* 2013, 24, 6522-6577; Stangherlin et al., *Cir. Res.* 2011, 108, 929-939. Accordingly, in some embodiments, the present disclosure provides a method of enhancing neuronal plasticity, comprising administering to a subject in need thereof an effective amount of a chemical entity of Formula (I). In specific embodiments, chemical entities of the present disclosure are useful in methods of enhancing cognitive or motor function, comprising administering to a subject in need thereof an effective amount of a chemical entity of any one of the embodiments disclosed herein.

In some embodiments, chemical entities of the present disclosure are useful as "agents" (or "augmenting agents") to increase the efficiency of training protocols, which facilitate functional reorganization in targeted "domains" (or "functions") in the brain. As described further herein, training protocols, which include cognitive and motor training, induce neuronal activity in specific brain regions and produce improved performance of a specific brain (cognitive or motor) function. Training protocols can therefore be directed to rehabilitating or enhancing a cognitive or motor function.

Chemical entities of the present disclosure can act as augmenting agents by shortening the time that methods of rehabilitating (or enhancing) a cognitive or motor function result in improved performance or a functional gain. Such augmented training therefore comprises a specific training protocol for a particular brain function, such as that underlying declarative memory, performance of a fine motor skill, a specific locomotor function, language acquisition, executive function, etc.; and a general administration of an augmenting agent of the present disclosure.

Chemical entities of the present disclosure are also useful in methods (or the manufacture of a medicament for use in such methods) of modulating PDE2 activity, comprising exposing PDE2 to an affective amount of a chemical entity of any one of the embodiments disclosed herein. In some embodiments, the PDE2 is in an animal, and more particularly, is in a human subject.

Neurological Disorders

Chemical entities and compositions of the present disclosure are useful in methods (or in the manufacture of a medicament for use in such methods) of treating a neurological disorder, comprising administering to a subject in need thereof an effective amount of a chemical entity of any one of the embodiments disclosed herein. In a specific aspect, the methods are directed to a cognitive deficit ("cognitive impairment") or motor deficit ("motor impairment") associated with (or "due to") the neurological disorder.

A neurological disorder (or condition or disease) is any disorder of the body's nervous system. Neurological disorders can be categorized according to the primary location affected, the primary type of dysfunction involved, or the primary type of cause. The broadest division is between peripheral nervous system (PNS) disorders and central nervous system (CNS) disorders (such as mental and psychiatric disorders). Neurological disorders are well-known in the art, and they include, but are not limited to, the following mental and psychiatric disorders:

Neurodevelopmental (or "developmental" disorders), such as intellectual disability disorders (e.g., Rubinstein-Taybi syndrome, Down syndrome); communication disorders; autism-spectrum disorders; attention-deficit/hyperactivity disorders; specific learning, language, or reading (e.g., dyslexia) disorders; motor disorders; fetal alcohol spectrum disorders (FASD); and other neurodevelopmental disorders;

Schizophrenia spectrum and other psychotic disorders, such as schizophrenia, schizotypal (personality) disorder, delusional disorder, brief psychotic disorder, schizoaffective disorder, substance/medication-induced psychotic disorder, psychotic disorder due to another medical condition, catatonia, catatonia associated with another mental disorder (catatonia specifier), catatonic disorder due to another medical condition, unspecified catatonia, schizophreniform disorder, and other schizophrenia spectrum and psychotic disorders;

Bipolar and related disorders, such as Bipolar I and II disorders, cyclothymic disorders, and other bipolar and related disorders;

Depressive disorders, such as major depressive disorder, persistent depressive disorder (dysthymia), a major depressive episode of the mild, moderate, or severe type, a depressive episode with melancholic features, a depressive episode with catatonic features, seasonal depression (seasonal affective disorder), disruptive mood dysregulation disorder, premenstrual dysphoric disorder, substance/medication-induced depressive disorder, depressive disorder due to another medical condition, mood disorders due to a general medical conditions, and other depressive disorder;

Anxiety disorders, such as specific phobia, agoraphobia, social anxiety disorder (social phobia), panic attack, panic disorder, acute stress disorder, generalized anxiety disorder, posttraumatic stress disorder (PTSD), and other anxiety disorders;

Obsessive-compulsive and related disorders, such as obsessive-compulsive disorder (OCD), body dysmorphic disorder, hoarding disorder, trichotillomania (hair-pulling disorder), excoriation (skin-picking) disorder, substance/medication-induced obsessive-compulsive and related disorder, obsessive-compulsive and related disorder due to another medical condition, and other specified obsessive-compulsive and related disorder and unspecified obsessive-compulsive and related disorder (e.g., body-focused repetitive behavior disorder, obsessional jealousy), and other obsessive-compulsive and related disorders;

Dissociative disorders, such as dissociative identity disorder, dissociative amnesia, depersonalization/derealization disorder, dissociative subtypes (in conjunction with other disorders), and other dissociative disorders;

Disruptive, impulse-control, and conduct disorders, such as conduct disorder, antisocial personality disorder, pyromania, kleptomania, and other disruptive, impulse-control, and conduct disorders;

Trauma- and stressor-related disorders, such as reactive attachment disorder, disinhibited social engagement disorder, posttraumatic stress disorder, acute stress disorder, adjustment disorders, and other trauma- and stressor-related disorders;

Feeding and eating disorders, such as pica, rumination disorder, avoidant/restrictive food intake disorder, anorexia, bulimia, binge-eating disorder, and other feeding and eating disorders;

Sleep-wake disorders, insomnia disorder, hypersomnolence disorder, narcolepsy, breathing-related sleep disorders, sleep apnea, circadian rhythm sleep-wake disorders, non-rapid eye movement (NREM) sleep arousal disorders, nightmare disorder, rapid eye movement (REM) sleep behavior disorder, restless legs syndrome, and substance/medication-induced sleep disorder, parasomnias, and other sleep-wake disorders;

Sexual disorders, such as arousal disorders, desire disorders, substance- and medication-induced dysfunctions, and other sexual disorders;

Substance-related and addictive disorders, such as those involving alcohol, drugs, stimulants, opioids, tobacco, and non-substance-related disorders; and other substance-related and addictive disorders; and Personality disorders, such as antisocial personality disorder, borderline personality disorder, histrionic personality disorder, narcissistic personality disorder, avoidant personality disorder, dependent personality disorder, obsessive-compulsive personality disorder, paranoid personality disorder, schizoid personality disorder, schizotypal personality disorder, personality change due to another medical condition, and other personality disorders;

Somatic symptom and related disorders, such as somatic symptom disorder, illness anxiety disorder (hypochondriasis), factitious disorder, factitious disorder imposed on another, pain disorders, conversion disorder, and other somatic symptom and related disorders.

In particular embodiments, the disorder is schizophrenia or an anxiety disorder.

In some embodiments, the neurological disorder is an acquired disorder, in which the primary clinical feature is impaired cognition. That is, it is a disorder in which the primary cognitive deficit has not been present since birth or very early life and therefore represents a decline from a previously attained level of functioning. Such disorders, which may be referred to herein as "cognitive disorders" or "neurocognitive disorders" include one or more of the following:

Delirium, such as substance-intoxication (or withdrawal) delirium, medication-induced delirium, and other forms of delirium;

Dementias and other cognitive impairments due to HIV infection or due to neurodegenerative diseases, such as Alzheimer's disease, Parkinson's disease (in particular Parkinson's Disease Dementia (PDD)), Huntington's disease, Lewy body disease, Pick's disease, a prion disease (e.g., Creutzfeldt-Jakob disease), Amyotrophic lateral sclerosis (ALS), multiple sclerosis, frontotemporal lobar degeneration, and corticobasal degeneration; dementia due to a vascular disease ("vascular disease"); and other dementias and neurodegenerative diseases;

Age-associated cognitive deficits, including age-associated memory impairment (AAMI), also referred to as age-related memory impairment (AMI) (see, e.g., Crook et al., *Devel. Neuropsychol.* 1986, 2, 261-276); and deficits affecting patients in early stages of cognitive decline, as in Mild Cognitive Impairment (MCI) (see, e.g., Arnáiz and Almkvist, *Acta Neurol. Scand. Suppl.* 2003, 179, 34-41), and;

Trauma-dependent losses of cognitive function, such as vascular diseases due to stroke (e.g., ischemic or hemorrhagic stroke) or ischemia; microvascular disease arising from diabetes or arthrosclerosis; traumatic brain injury (TBI), such as brain trauma, including subdural hematoma and brain tumor; head trauma (closed and penetrating); head injury; tumors, such as nervous system cancers, including cerebral tumors affecting the thalamic or temporal lobe; hypoxia, and viral, fungal, or bacterial infection (e.g., encephalitis, or meningitis); excitotoxicity; and seizures; and Cognitive impairments due to chemotherapy, such as post-chemotherapy cognitive impairments (PCCI); chemotherapy-induced cognitive dysfunction or impairments; chemo brain; or chemo fog.

Such acquired disorders are not necessarily limited to cognitive impairments. For example, trauma related disorders, such as stroke, traumatic brain injury, head trauma, and head injury, may also include impairments in other neurological functions, such as impairments in motor functions.

As used herein, the terms "Neurodevelopment disorders," "Schizophrenia spectrum and other psychotic disorders," Bipolar and related disorders," "Depressive disorders," "Anxiety disorders," "Obsessive-compulsive and related disorders," "Dissociative disorders," "Disruptive, impulse-control, and conduct disorders," "Trauma- and stressor-related disorders," "Feeding and eating disorders," "Sleep-wake disorders," "Sexual disorders," "Substance-related and addictive disorders," "Personality disorders," "Delirium," "Neurodegenerative disorders," "Neurocognitive disorders," "Age-associated cognitive deficits," "Delirium,"

"Dementias," and "Trauma" include the diagnosis and classification of these conditions and disorders (and related conditions and disorders) as described in the Diagnostic and Statistical Manual of Mental Disorders (DSM-5; $5^{th}$ ed., 2013, American Psychiatric Association). The skilled artisan will recognize that there are alternative nomenclature and classification systems for these disorders, and that these systems evolve with medical and scientific progress. Thus the terms described in this paragraph are intended to include like disorders that are described in other diagnostic sources.

In other embodiments, the neurological disorder is a movement or motor disorder, a group that includes, but is not limited to: kinesias and akinetic-rigid syndromes, such as Parkinson's disease or corticobasal degeneration; Tourette's syndrome, epilepsy, muscular spasms, and disorders associated with muscular spasticity or weakness; dyskinesias, including tremors, such as rest tremor, postural tremor and intention tremor); chorea, such as that in Huntington's disease; myoclonus (including generalized myoclonus and focal myoclonus); tics (including simple tics, complex tics and symptomatic tics); dystonia; restless leg syndromes; Wilson's Disease; Hallervorden-Spatz disease; basal ganglia disorders; hyperkinetic, hypokinetic, and dyskinetic disorders; movement disorders induced by drugs; diseases associated with striatal hypofunction; and other movement and motor disorders In specific embodiments, the dyskinetic disorder is a drug-induced dyskinesia. More particularly, the dyskinetic disorder is levodopa induced dyskinesia (LID) or tardive dyskinesia (TD), which represent the most common forms of drug-induced dyskinesias. For example, uncontrolled stimulation of supersensitized dopamine D1 receptors in the direct striatonigral pathway are thought to mediate LIDs. In addition, long-term blockade of dopamine D2 receptors in the basal ganglia by dopamine D2 antagonists (e.g., neuroleptics) may produce compensatory supersensitivity of dopamine receptors and TD. Accordingly, in specific embodiments, the present disclosure provides methods of treating LID (or TD), comprising administering to a subject in need therefor an effective amount of a chemical entity of any of the embodiments disclosed herein. In particular embodiments, the chemical entity is a compound, or pharmaceutically acceptable salt thereof, of Formula (I).

In certain embodiments, chemical entities of the present disclosure provide augmenting agents to enhance the efficiency of training protocols, including cognitive training and motor training protocols. Such methods are known as "augmented training," and, more particularly, "augmented cognitive training" or "augmented motor training."

Training (or a "training protocol") generally requires many sessions to attain the desired benefits, for example, to rehabilitate a motor deficit or language deficit following stroke. This can be costly and time-consuming, deterring subject compliance and the realization of real world benefits that endure over time. The efficiency of such training protocols can be improved by administering certain agents (known as augmenting agents) in conjunction with the training protocol (see, e.g., U.S. Pat. Nos. 7,868,015; 7,947,731; U.S. 2008-0188525). When administered in combination with training protocols (or "training"), augmenting agents enhance functional reorganization in targeted domains (or "functions") in the brain.

Cognitive domains (or functions) that can be targeted by training protocols include, but are not limited to, the following: attention (e.g., sustained attention, divided attention, selective attention, processing speed); executive function (e.g., planning, decision, and working memory); learning and memory (e.g., immediate memory; recent memory, including free recall, cued recall, and recognition memory; and long-term memory, which can be divided into explicit memory (declarative memory), such as episodic, semantic, and autobiographical memory, and into implicit memory (procedural memory)); language (e.g., expressive language, including naming, word recall, fluency, grammar, and syntax; and receptive language); perceptual-motor functions (e.g., abilities encompassed under visual perception, visuo-constructional, perceptual-motor praxis, and gnosis); and social cognition (e.g., recognition of emotions, theory of mind). In specific embodiments, the cognitive function is learning and memory. In one specific aspect, the learning and memory function is working memory. In another specific aspect, the learning and memory function is long-term memory.

Motor domains (or functions) that can be targeted by training protocols include, but are not limited to, those involved in gross body control, coordination, posture, and balance; bilateral coordination; upper and lower limb coordination; muscle strength and agility; locomotion and movement; motor planning and integration; manual coordination and dexterity; gross and fine motor skills; and eye-hand coordination.

Augmented Training

In certain embodiments, chemical entities of the present disclosure provide augmenting agents to enhance the efficiency of training protocols, including cognitive training and motor training protocols. Such methods are known as "augmented training," and, more particularly, "augmented cognitive training" or "augmented motor training."

Training (or a "training protocol") generally requires many sessions to attain the desired benefits, for example, to rehabilitate a motor deficit or language deficit following stroke. This can be costly and time-consuming, deterring subject compliance and the realization of real world benefits that endure over time. The efficiency of such training protocols can be improved by administering certain agents (known as augmenting agents) in conjunction with the training protocol (see, e.g., U.S. Pat. Nos. 7,868,015; 7,947,731; U.S. 2008-0188525). When administered in combination with training protocols (or "training"), augmenting agents enhance functional reorganization in targeted domains (or "functions") in the brain.

Cognitive domains (or functions) that can be targeted by training protocols include, but are not limited to, the following: attention (e.g., sustained attention, divided attention, selective attention, processing speed); executive function (e.g., planning, decision, and working memory); learning and memory (e.g., immediate memory; recent memory, including free recall, cued recall, and recognition memory; and long-term memory, which can be divided into explicit memory (declarative memory) memory, such as episodic, semantic, and autobiographical memory, and into implicit memory (procedural memory)); language (e.g., expressive language, including naming, word recall, fluency, grammar, and syntax; and receptive language); perceptual-motor functions (e.g., abilities encompassed under visual perception, visuo-constructional, perceptual-motor praxis, and gnosis); and social cognition (e.g., recognition of emotions, theory of mind). In specific embodiments, the cognitive function is learning and memory, and more particularly, long term memory.

Motor domains (or functions) that can be targeted by training protocols include, but are not limited to, those involved in gross body control, coordination, posture, and balance; bilateral coordination; upper and lower limb coordination; muscle strength and agility; locomotion and movement; motor planning and integration; manual coordination and dexterity; gross and fine motor skills; and eye-hand coordination.

Training Protocols

Training protocols (or "modules") are well known in the art and typically comprise a set of distinct exercises that can be process-specific or skill-based: See, e.g., Kim et al., *J. Phys. Ther. Sci.* 2014, 26, 1-6, Allen et al., *Parkinson's Dis.* 2012, 2012, 1-15; Jaeggi et al., *Proc. Natl. Acad. Sci. USA* 2011, 108, 10081-10086; Chein et al., *Psychon. Bull. Rev.* 2010, 17, 193-199; Klingberg, *Trends Cogn. Sci.* 2010, 14, 317-324; Owen et al., *Nature* 2010, 465, 775-778; Tsao et al., *J. Pain* 2010, 11, 1120-1128; Lustig et al., *Neuropsychol. Rev.* 2009, 19, 504-522; Park and Reuter-Lorenz, *Ann. Rev. Psych.* 2009, 60, 173-196; Oujamaa et al., *Ann. Phys. Rehabil. Med.* 2009, 52, 269-293; Frazzitta et al., *Movement Disorders* 2009, 8, 1139-1143; Jaeggi et al., *Proc. Natl. Acad. Sci. USA* 2008, 105, 6829-6833; Volpe et al., *Neurorehabil. Neural Repair* 2008, 22, 305-310; Fischer et al., *Top. Stroke Rehab.* 2007, 14, 1-12; Jonsdottir et al., *Neurorehabil. Neural Repair* 2007, 21, 191-194; Stewart et al., *J. Neurol. Sci.* 2006, 244, 89-95; Krakauer, *Curr. Opin. Neurol.* 2006, 19, 84-90; Belleville et al., *Dement. Geriatr. Cogn. Disord.* 2006, 22, 486-499; Klingberg et al., *J. Am. Acad. Child. Adolesc. Psychiatry* 2005, 44, 177-186; Dean et al., *Arch. Phys. Med. Rehabil.* 2000, 81, 409-417; Whitall et al., *Stroke* 2000, 31, 2390-2395; Hummelsheim and Eickhof, *Scand. J. Rehabil. Med.* 1999, 31, 250-256; Merzenich et al., *Science* 1996, 271, 77-81; Merzenich et al., *Cold Spring Harb. Symp. Quant. Biol.* 1996, 61, 1-8; Rider and Abdulahad, *Percept. Mot. Skills* 1991, 73, 219-224.

Process-specific training focuses on improving a particular domain such as attention, memory, language, executive function, or motor function. Here the goal of training is to obtain a general improvement that transfers from the trained activities to untrained activities based on the same cognitive or motor function or domain.

Skill-based training is aimed at improving performance of a particular activity or ability, such as learning a new language, performing a musical instrument, improving memory, or learning a fine motor skill. The different exercises within such a protocol will focus on core components within one or more domains underlying the skill. Modules for increasing memory, for example, may include tasks directed to specific domains involved in memory processing, e.g., the recognition and use of fact, and the acquisition and comprehension of explicit knowledge rules.

In some embodiments, the battery of exercises is administered as part of a single training session. In one aspect, the training protocol comprises multiple training sessions, each separated by a discrete interval. In another aspect, the number of training sessions sufficient to improve performance is reduced compared to that produced by training alone.

In a further aspect, the augmenting agent is a PDE2 inhibitor, and more particularly, is a chemical entity of the present disclosure, and is administered in conjunction with training. The phrase "in conjunction with" means that the augmenting agent enhances CREB pathway function during training. In some embodiments, the deficit is a motor deficit. In other embodiments, the deficit is a cognitive deficit. In still other embodiments, the deficit may include both a cognitive and motor deficit. In other aspects, the compound is administered before and during each training session. In one aspect, the subject is a human. In some embodiments, the subject is a non-human, and more particularly, is a primate or a canine.

In one aspect, a compound or composition of the present disclosure can be used as an augmenting agent in conjunction with any psychotherapeutic approach intended to modulate cognitive function in the brain, thereby enhancing the efficacy of such therapy by reducing the number of sessions necessary to attain benefits.

Stroke

In some embodiments, chemical entities and compositions of the present disclosure are useful in treating stroke, and in more specific embodiments, treating motor or cognitive impairments during post-stroke rehabilitation. Stroke care is a temporal continuum that includes immediate (acute) treatments and subsequent rehabilitative therapy.

Acute treatments directly target the initial damage, such as that triggered by ischemic or hemorrhagic stroke; they usually involve using agents to dissolve clots and restore blood flow to reduce tissue damage and stabilize the patient. The efficacy of acute treatments is typically limited to a short time window extending only a few hours from stroke onset.

The focus of stroke treatment shifts to rehabilitation after the patient has been medically stabilized. Rehabilitation (also referred to as "stroke rehabilitation" or "post-stroke rehabilitation") is directed to cognitive and motor deficits that persist after the initial stroke injury, the goal being to restore and recover neurological function as much as possible to compensate for the permanent tissue loss (e.g., 1995 Clinical Guideline by the Department of Health and Human Services on Post-Stroke Rehabilitation).

Stroke rehabilitation is typically a comprehensive program coordinated by a team of medical professionals. A physical therapist on the team, for example, may focus on maintaining and restoring range of motion and strength in affected limbs, maximizing mobility in walking, improving manual dexterity, and rehabilitating other motor and sensorimotor functions. A mental health professional may be involved in the treatment of loss of cognitive skills. Rehabilitation services can occur in multiple environments, such as a rehabilitation hospital, long-term care facility, outpatient clinic, or at home.

Neurological functions impacted by stroke (and which can be targeted during rehabilitation) include impairments in cognitive and motor functions. Cognitive function impairments, for example, can manifest as deficits in understanding speech or writing (aphasia); knowing the right words but having trouble saying them clearly (dysarthria); as well as deficits in other cognitive functions, such as attention, reasoning, planning, execution, and learning and memory. Motor function impairments, for example, can manifest as weakness (hemiparesis) or paralysis (hemiplegia) on one side of the body that may affect the whole side or just the arm or leg; by problems with balance or coordination; deficits in gross motor skills such as gait and walking speed; deficits in fine motor skills or manual dexterity; and deficits in upper and lower extremity function.

Accordingly, the present disclosure provides the use of a PDE2 inhibitor of the present disclosure in the treatment of stroke, including post stroke rehabilitation. In certain embodiments, chemical entities are useful during stroke rehabilitation to treat stroke deficits (or "post-stroke deficits") resulting from impaired neurological functions. Some embodiments provide methods of treating a neurological deficit during post-stroke rehabilitation comprising: (a) administering to a subject in need thereof a PDE2 inhibitor disclosed herein during recovery of the subject from stroke;

(b) providing training to the subject under conditions sufficient to improve performance of a neurological function whose impairment is due to the deficit; and (c) repeating steps (a) and (b) one or more times, whereby the amount of training sufficient to improve the performance is reduced compared to that produced by training alone.

In one aspect, the PDE2 inhibitor is a chemical entity of the present disclosure, and more specifically, is a compound, or pharmaceutically acceptable salt thereof, of Formula (I). In some embodiments, the deficit is a motor deficit. In other embodiments, the deficit is a cognitive deficit, particularly, a deficit in memory formation, and more specifically, a deficit in long-term memory formation. In still other embodiments, the deficit may include a cognitive and motor deficit. In another aspect, training comprises a battery of tasks directed to the neurological function. In a specific aspect, the reduction in the amount of training is a reduction in the number of training sessions.

In a further embodiment, the administering step (a) is in conjunction with the training step (b). In one aspect, the subject is a human. In another aspect, the subject has undergone neuronal stem cell manipulation. In other aspects, the compound is administered before and during each training session.

Traumatic Brain Injury

In some embodiments, chemical entities and compositions are useful in treating traumatic brain injury (TBI), and in more specific embodiments, treating motor or cognitive impairments during rehabilitation after the initial trauma. Like stroke care, TBI case is a temporal continuum that includes immediate (acute) treatments and subsequent rehabilitative therapy.

Some embodiments provide the use of a PDE2 inhibitor disclosed herein in the treatment of TBI, including during TBI rehabilitation to treat TBI deficits (or "post-TBI deficits") resulting from impaired neurological functions. Some embodiments provide methods of treating a neurological deficit during post-TBI rehabilitation comprising: (a) administering to a subject in need thereof a PDE2 inhibitor during recovery of the subject from TBI; (b) providing training to the subject under conditions sufficient to improve performance of a neurological function whose impairment is due to the deficit; and (c) repeating steps (a) and (b) one or more times, whereby the amount of training sufficient to improve the performance is reduced compared to that produced by training alone.

In one aspect, the PDE2 inhibitor is a chemical entity of the present disclosure, and more specifically, is a compound, or pharmaceutically acceptable salt thereof, of Formula (I). In some embodiments, the deficit is a motor deficit. In other embodiments, the deficit is a cognitive deficit, particularly, a deficit in memory formation, and more specifically, a deficit in long-term memory formation. In still other embodiments, the deficit may include a cognitive and motor deficit. In another aspect, training comprises a battery of tasks directed to the neurological function. In a specific aspect, the reduction in the amount of training is a reduction in the number of training sessions.

In a further embodiment, the administering step (a) is in conjunction with the training step (b). In one aspect, the subject is a human. In another aspect, the subject has undergone neuronal stem cell manipulation. In other aspects, the compound is administered before and during each training session.

Peripheral Disorders

Chemical entities and compositions of the present disclosure are useful in methods of treating peripheral disorders, that is, disorders other than a primary neurological disorder. These uses are supported by PDE2A expression studies and other observations (see, e.g., Bernard et al., *PLoS ONE* 2014, 9, e109862; Hiramoto et al., *Cell. Signal.* 2014, 26, 1807-1817; Savai et al., *Expert Opin. Investig. Drugs* 2010, 19, 117-131; Bayer Healthcare AG, Intl. Pat. Appl. Publ. WO/2004/044234, May 27, 2004; Donzeau-Gouge et al., *J. Physiol.* 2001, 533, 329-340; Herring et al., Card. Res. 2001, 52, 446-453; Keravis et al., *J. Vasc. Res.* 2000, 37, 235-249; Wolda et al., *J. Histochem. Cytochem.* 1999, 47, 895-906; Dickinson et al., *Biochem. J.* 1997, 323, 371-377; Fischmeister et al., *J. Clin. Invest.* 1997, 99, 2710-2718; Houslay et al., *Cell. Signal.* 1996, 8, 97-110; and Haynes et al., *J. Pharm. Exp. Ther.* 1996, 276, 752-757).

Accordingly, in some embodiments, the present disclosure provides methods of treating a peripheral disorder, comprising administering to a subject in need thereof an effective amount of a chemical entity of Formula (I). Peripheral disorders include, but are not limited to, infectious diseases, such as bacterial, fungal, protozoan, and viral infections; hematological diseases, such as anemias, myeloproliferative disorders, hemorrhagic disorders, leukopenias, eosinophilic disorders, leukemias, lymphomas, and plasma cell dyscrasias; cardiovascular diseases such as congestive heart failure, myocardial infarction, ischemic diseases, atrial and ventricular arrhythmias, pulmonary hypertension, hypertensive vascular diseases, and atherosclerosis; gastroenterological disorders, such as diseases of the esophagus, stomach, duodenum, pancreas, bowel, and liver; dermatological disorders, such as psoriasis, dermatitis, impetigo, folliculitis, melanoma, and skin cancers; renal diseases, in particular kidney failure; inflammatory diseases; migraine disorders; cancer pain; and other peripheral disorders.

Animal Skill Training Protocols

In some embodiments, chemical entities of the present invention are used to enhance the efficiency of training protocols directed to cognitive and motor skills in an animal. Such augmented training reduces the time necessary to acquire or enhance a cognitive or motor skill in the non-human animal.

In particular embodiments, the animal is a non-human animal, and more particularly, is a service animal, a category that includes, but is not limited to, dogs, miniature horses, and capuchin monkeys. Service animals may be involved in public service or private service, and the training protocols will be appropriately matched to these objections. For example, training protocols directed to public service include public order maintenance, search and rescue, and contraband detection, and training protocols directed to private service include private security, handicap assistance, health care, psychiatric assistance, and pest control.

The training protocol may be directed to a single skill, such as the detection of a single drug in a service animal. In other embodiments, the training protocol may be directed to a complex set of skills, such as those underlying search and rescue training of a service animal; for a complex set of skills, training will therefore comprise more than one task.

Accordingly, in some embodiments, the present disclosure provides a method of enhancing the efficiency of an animal skill training protocol, comprising (a) administering to an animal in need thereof a chemical entity of one of the disclosed embodiments; (b) training the animal under conditions sufficient to improve performance of one or more skills; and (c) repeating steps (a) and (b) one or more times, whereby the amount of training sufficient to improve the performance is reduced compared to that produced by training alone. In some embodiments, the animal is a service animal, and, more particularly, a dog. In some embodiments, the training protocol is directed to a single skill. In some embodiments, the training protocol is directed to multiple skills. In some embodiments, the administering step occurs in conjunction with the training step.

Treatment Combinations

In some embodiments, a chemical entity of Formula (I) is administered with another active agent to treat an indication disclosed herein, such as part of an adjunct therapy. In specific embodiments, the combination is administered to treat schizophrenia, Parkinson's disease, Alzheimer's disease, Huntington's disease, anxiety and depressive disorders, or migraine disorders. Such administration may be simultaneous, sequential, or staggered.

Exemplary agents for treating schizophrenia include: clozapine, aripiprazole, brexpiprazole, cariprazine, lurasidone, paliperidone, quetiapine, risperidone, olanzapine, ziprasidone, and iloperidone.

Exemplary agents for treating Parkinson's disease include, but are not limited to, dopamine preparations, dopamine agonists, or COMT agents (drugs that inhibit the action of catechol-methyl transferase).

Exemplary agents for treating Alzheimer's disease include, but are not limited to, donepezil, rivastigmine, galantamine, marijuana-like cannabinoids, and memantine.

Exemplary agents for treating Huntington's disease (or other motor disorders) may include, but are not limited to, tetrabenazine, as well as antipsychotic drugs such as haloperidol, chlorpromazine, risperidone, and quetiapine, and anti-epileptic drugs such as levetiracetam and clonazepam, which may be beneficial in treating chorea or related motor disorders.

Exemplary agents for treating anxiety or depression include benzodiazepines and other anxiolytics; serotonin reuptake inhibitors (SSRIs), such as sertraline, fluoxetine, citalopram, escitalopram, paroxetine, fluvoxamine. and trazodone; serotonin and norepinephrine reuptake inhibitors (SNRIs), such as desvenlafaxine, duloxetine, levomilnacipran, and venlafaxine; tricyclic antidepressants (TCAs), such as amitriptyline, amoxapine, clomipramine, desipramine, doxepin, imipramine, nortriptyline, protriptyline, and trimipramine; monoamine oxidase inhibitors (MAOIs), such as isocarbox azid, phenelzine, selegiline, and tranylcypromine; and other classes of drugs, such as maprotiline, bupropion, vilazodone, nefazodone, trazodone, vortioxetine, and mirtazapine Exemplary agents for treating migraine disorders include, but are not limited to, caffeine; acetaminophen; nonsteroidal anti-inflammatory drugs (NSAIDs), such as aspirin, ibuprofen, naproxen, ketoprofen, tolmetin, etodolac, nabumetone, piroxicam, and droxicam; cyclo-oxygenease-2 (Cox-2) inhibitors such as celecoxib; topiramate; amitriptyline; sumatriptan; frovatriptan; rizatriptan; naratriptan; almotriptan; eletriptan; botulinum toxin; narcotic pain medications such as codeine, fentanyl, hydrocodone, hydromorphone, meperidine, methadone, morphine, and oxycodone; centrally acting analgesics, such as tramadol; and other classes of drugs, such as certain anticonvulsants, antidepressants, psychostimulants, marijuana cannabinoids, marijuana-like cannabinoids, and corticosteroids.

The preceding list of additional active agents is meant to be exemplary rather than fully inclusive. Additional active agents not included in the above list may be administered in combination with a compound of Formula (I). The additional active agent will be dosed according to its approved prescribing information, though in some embodiments the additional active agent may be dosed at less the typically prescribed dose.

EXAMPLES

The present disclosure will be further illustrated by the following non-limiting Examples. These Examples are understood to be exemplary only, and they are not to be construed as limiting the scope of the one or more embodiments, and as defined by the appended claims.

Preparative Examples

Exemplary compounds will now be described by reference to the illustrative synthetic schemes for their general preparation below and the specific examples to follow.

One skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between −78° C. and the reflux temperature of the solvent. Reactions may be heated employing conventional heating or microwave heating. Reactions may also be conducted in sealed pressure vessels above the normal reflux temperature of the solvent.

Abbreviations

The specification includes numerous abbreviations, whose definitions are listed in the following Table:

TABLE 1

| Abbreviation | Definition |
|---|---|
| ACN, $CH_3CN$ | Acetonitrile |
| AcOH or HOAc | Acetic Acid |
| $AC_2O$ | Acetic Anhydride |
| APCI | Atmospheric pressure chemical ionization |
| Boc | tert-Butyloxycarbonyl |
| nBuLi | n-butyl Lithium |
| cataCXium A ® | Di(1-adamantyl)-n-butylphosphine |
| CELITE ® | Diatomaceous earth |
| $CHCl_3$ | Chloroform |
| $(COCl)_2$ | Oxalyl chloride |
| CuI | Copper(I) iodide |
| DCE | Dichloroethane |
| DCM, $CH_2Cl_2$ | Dichloromethane |
| DMA | N,N-Dimethylacetamide |
| DMF | N,N-Dimethylformamide |
| DMSO | Dimethylsulfoxide |
| EtOAc, or EA | Ethyl Acetate |
| EtOH | Ethanol |
| ESI | Electrospray ionization |
| FCC | Flash column chromatography |
| HCl | Hydrochloric acid |
| HCOOH | Formic acid |
| $H_2O$ | Water |
| $H_2O_2$ | Hydrogen Peroxide |
| $H_2SO_4$ | Sulfuric acid |
| HPLC | High-performance liquid chromatography |
| $K_2CO_3$ | Potassium carbonate |
| KOtBu | Potassium tert-butoxide |
| LCMS, LC/MS | Liquid chromatography-mass spectrometry |

TABLE 1-continued

| Abbreviation | Definition |
|---|---|
| LiOH | Lithium hydroxide |
| MeOH | Methanol |
| MeTHF | 2-Methyltetrahydrofuran |
| $MgSO_4$ | Magnesium sulfate |
| NaCl, brine | Sodium chloride |
| NaH | Sodium hydride |
| $NaHCO_3$ | Sodium bicarbonate |
| NaOtBu | Sodium tert-butoxide |
| NaOH | Sodium hydroxide |
| $Na_2CO_3$ | Sodium carbonate |
| $Na_2SO_4$ | Sodium sulfate |
| NBS | N-Bromosuccinimide |
| NCS | N-Chlorosuccinimide, 1-chloropyrrolidine-2,5-dione |
| $NH_4Cl$ | Ammonium chloride |
| $NH_2NH_2$ | Hydrazine |
| NIS | N-Iodosuccinimide |
| NMM | N-methylmorpholine |
| NMP | 1-Methyl-2-pyrrolidinone |
| NMR | Nuclear magnetic resonance |
| $PBr_3$ | Phosphorous tribromide |
| Pd/C | Palladium on carbon, 10 wt. % |
| $Pd(dppf)Cl_2$ | [1,1'-Bis(diphenylphosphino)ferrocene]palladium(II) dichloride |
| $Pd(OAc)_2$ | Palladium(II) acetate |
| SFC | Super-critical fluid chromatography |
| $SiO_2$ | Silicon dioxide |
| $SOCl_2$ | Thionyl chloride |
| TsCl | 4-Toluenesulfonyl chloride |
| pTsOH, PTSA | p-Toluenesulfonic acid, 4-Methylbenzene-1-sulfonic acid |
| TEA, $Et_3N$ | Triethylamine |
| TFA | Trifluoroacetic acid |
| THF | Tetrahydrofuran |
| UPLC | Ultra-performance liquid chromatography |

Synthetic Schemes

SCHEME A

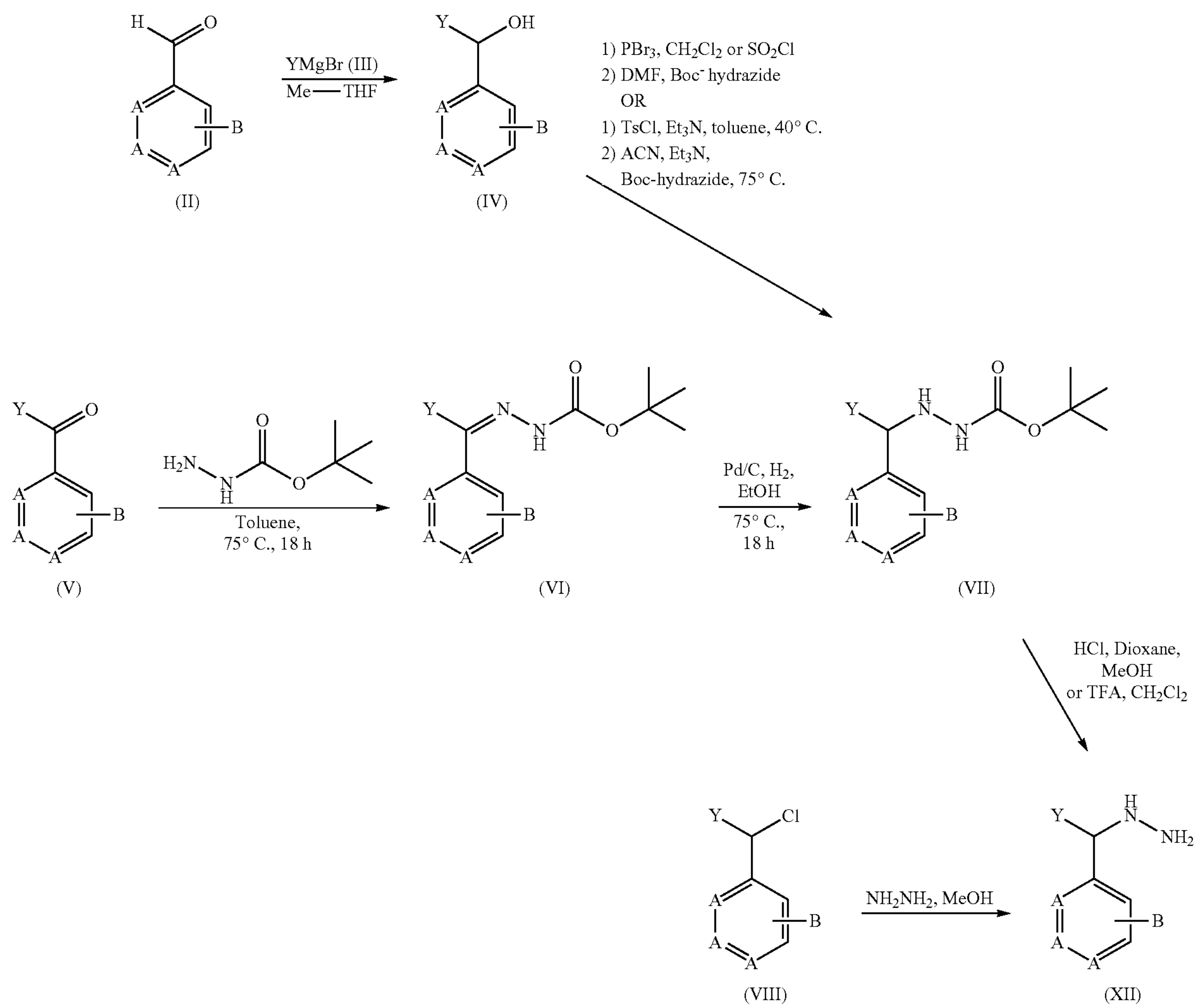

(II) (IV) (V) (VI) (VII) (VIII) (XII)

-continued

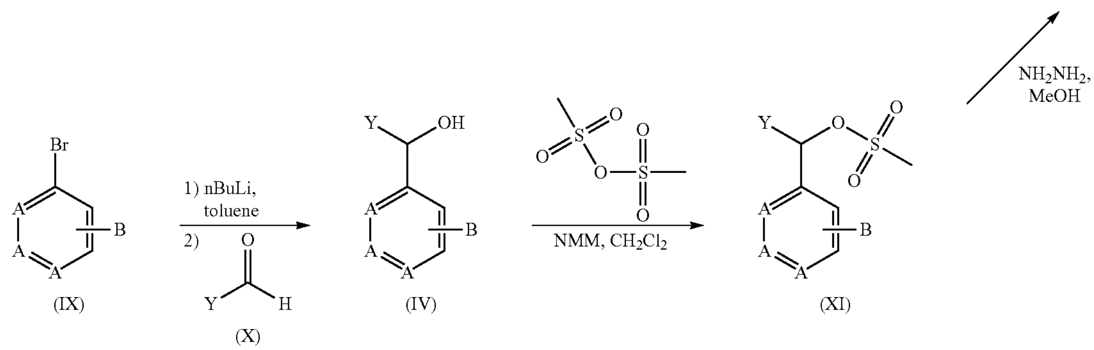

(IX) (X) (IV) (XI)

According to Scheme A, the synthesis of hydrazines of formula (XII) can be achieved using various synthetic routes. In one instance, hydrazines of formula (XII) can be synthesized in three steps from an aldehyde of formula (II) where A is carbon or nitrogen and B is -halo, —$C_{1-6}$alkyl, —$C_{1-6}$haloalkyl, —$C_{1-6}$alkoxy, —$C_{1-6}$haloalkoxy, and —$C_{3-5}$cycloalkyl. Grignard addition of an alkyl magnesium bromide of formula (III) to the aldehyde, under conditions known to one skilled in the art, in a solvent such as methyl-THF, THF or the like, provides an alcohol of formula (IV). Subsequent halogenation of the alcohol, for instance using a brominating reagent such as $PBr_3$ or the like, in a solvent such as $CH_2Cl_2$ or the like, or chlorination using thionyl chloride, followed by a nucleophilic substitution of the halide using Boc-hydrazide, in a solvent such as DMF or MeOH, provides a hydrazide compound of formula (VII). Alternatively, formation of the tosylate of a compound of formula (IV), by addition of 4-toluenesulfonyl chloride, in the presence of a base, such as $Et_3N$, in a solvent, such as toluene or the like, at a temperature of 40° C., followed by nucleophilic substitution of the tosylate using Boc-hydrazide, in a solvent such as ACN, in the presence of a base such as TEA at a temperature of 75° C., provides a hydrazide of formula (VII). Deprotection of the Boc protecting group, under acidic conditions, using an acid such as HCl or TFA or the like, in a solvent mixture such as methanol and dioxane or chloroform or the like, provides a hydrazine of formula (XII), where A is carbon or nitrogen, B is -halo, —$C_{1-6}$alkyl, —$C_{1-6}$haloalkyl, —$C_{1-6}$alkoxy, —$C_{1-6}$haloalkoxy, or —$C_{3-5}$cycloalkyl, and Y is —$C_{1-6}$alkyl.

Alternatively, commercially available or synthetically accessible ketones of formula (V) can be converted into a hydrazine of formula (XII) in three steps by formation of a hydrazone, followed by reduction to the hydrazide, then removal of the protecting group to provide the hydrazine. For example, treatment of a ketone of formula (V) with a hydrazide, such as tert-butoxycarbonyl hydrazide, in a solvent such as toluene or the like, at a temperature ranging from 60° C. to 100° C., affords a hydrazone of formula (VI). Subsequent reduction, under conditions known to one skilled in the art, using a catalyst such as Pd/C or the like, in the presence of hydrogen, in a solvent such as ethanol or methanol or the like, at a temperature ranging from room temperature to 80° C., provides a Boc protected hydrazine of formula (VII). Subsequent deprotection under acidic conditions, as previously described, provides a hydrazine of formula (XII), where A is carbon or nitrogen, B is -halo, —$C_{1-6}$alkyl, —$C_{1-6}$haloalkyl, —$C_{1-6}$alkoxy, —$C_{1-6}$haloalkoxy, or —$C_{3-5}$cycloalkyl, and Y is —$C_{1-6}$alkyl.

Additionally, a nucleophilic substitution reaction of an alkyl halide, such as an alkyl chloride of formula (VIII), with hydrazine in a solvent, such as methanol or the like, provides a hydrazine of formula (XII).

Using an additional method, a commercially available or synthetically accessible aryl halide or heteroaryl halide, such as an aryl bromide or heteroaryl bromide of formula (IX), can be converted into a hydrazine of formula (XII) in three steps. For example, dissolution of the bromide in a solvent such as toluene or THF or the like, cooled to a temperature such as −78° C., followed by treatment with a base such as n-butyl lithium or the like, then addition of an aldehyde provides an alcohol of formula (IV). Treatment of the alcohol with methanesulfonic anhydride in the presence of a base, such as NMM or the like, in a solvent, such as dichloromethane, provides a mesylate of formula (XI). Treatment of the mesylate with hydrazine in a solvent, such as methanol or the like, provides a hydrazine compound of formula (XII) where A is carbon or nitrogen, B is -halo, —$C_{1-6}$alkyl, —$C_{1-6}$haloalkyl, —$C_{1-6}$alkoxy, —$C_{1-6}$haloalkoxy, or —$C_{3-5}$cycloalkyl, and Y is —$C_{1-6}$alkyl.

SCHEME B

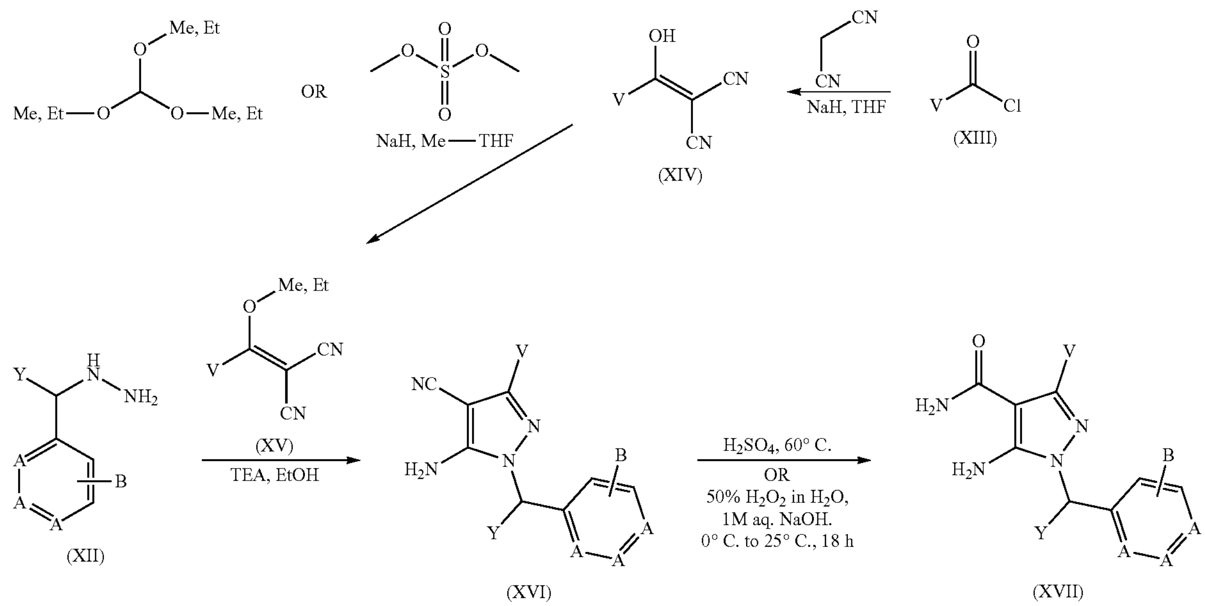

Substituted pyrazoles of formula (XVII) can be synthesized in two steps from hydrazine compounds of formula (XII) and a 2-(cycloalkyl(alkoxy)methylene) malononitrile of formula (XV), as shown in Scheme B.

2-(cycloalkyl(alkoxy)methylene) malononitrile can be synthesized in two steps from a cycloalkylcarbonyl chloride of formula (XIII). Treatment of cycloalkylcarbonyl chloride with malonitrile, in the presence of a base, such as sodium hydride or the like, in a solvent such as THF or the like, provides 2-(cycloalkyl(hydroxy)methylene) malononitrile. Subsequent treatment with a base, such as sodium hydride or the like, in a solvent such as methyl-THF or THF, followed like, provides a substituted 5-amino-3-cycloalkyl-4-nitrilepyrazole of formula (XVI). Further treatment with sulfuric acid, heated to a temperature of about 60° C., or with a 50% solution of hydrogen peroxide in water and an aqueous solution of sodium hydroxide (1 M) provides a substituted 5-amino-3-cycloalkyl-4-carboxamide of formula (XVII), where A is carbon or nitrogen, B is -halo, —$C_{1-6}$alkyl, —$C_{1-6}$haloalkyl, —$C_{1-6}$alkoxy, —$C_{1-6}$haloalkoxy, or —$C_{3-5}$cycloalkyl, V is —$C_{3-8}$cycloalkyl, and Y is —$C_{1-6}$alkyl.

SCHEME C

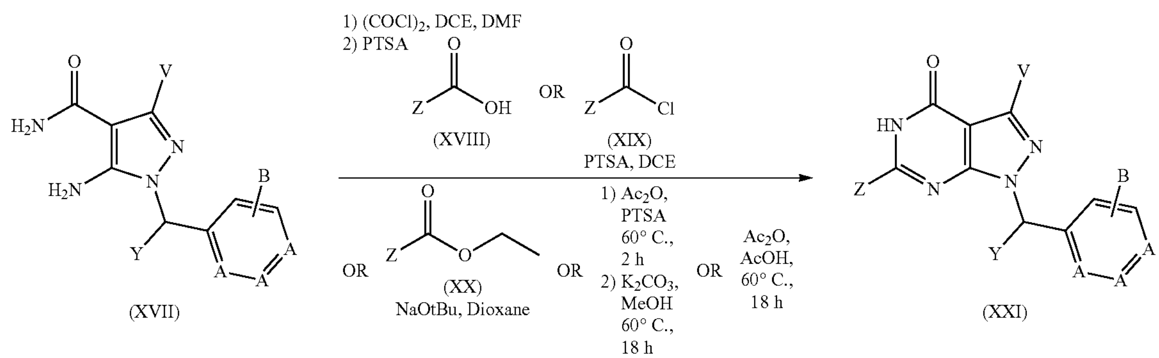

by addition of dimethyl sulfate affords a 2-(cycloalkyl (alkoxy)methylene) malononitrile compound of formula (XV). Alternatively, subsequent addition of the orthoester to a derivative of formula (XIV), at a temperature ranging from 80° C. to 120° C., affords a 2-(cycloalkyl(alkoxy)methylene) malononitrile compound of formula (XV). Addition of the 2-(cycloalkyl(alkoxy)methylene) malononitrile to a hydrazine of formula (XII), in the presence of a base such as triethylamine or the like, in a solvent such as ethanol or the According to Scheme C, pyrazolopyrimidinone compounds of formula (XXI) can be synthesized using a variety of methods from pyrazole compounds of formula (XVII). For example, treatment of a carboxylic acid of formula (XVIII) with oxalyl chloride, in a solvent such as dichloroethane or the like, in the presence of N,N-dimethylformamide and PTSA, followed by addition of said pyrazole compound of formula (XVII) provides a pyrazololpyrimidinone analog of formula (XXI), where A is carbon or nitrogen, B is -halo, —$C_{1-6}$alkyl, —$C_{1-6}$haloalkyl, —$C_{1-6}$alkoxy, —$C_{1-6}$haloalkoxy or —$C_{3-5}$cycloalkyl, V is —$C_{3-8}$cycloalkyl, Y is —$C_{1-6}$alkyl, and Z is —$C_{1-6}$alkyl, —$C_{1-6}$haloalkyl, —$C_{1-6}$alkoxy, —$(CH_2)_n$aryl, or —$(CH_2)_n$heteroaryl, said alkyl, aryl and heteroaryl optionally substituted with up to three members. In some embodiments, Z is —$C_{1-6}$alkoxy, —$(CH_2)_n$aryl, or —$(CH_2)_n$heteroaryl, said aryl and heteroaryl optionally substituted with up to 3 members, each independently selected from the group consisting of: -halo, —OH, —CN, —$CH_2OCH_3$, —$CH_2CH_2OCH_3$, —$N(CH_3)_2$, —$C_{1-6}$alkyl, —$C_{1-6}$haloalkyl, —$C_{1-6}$alkoxy, —$C_{1-6}$haloalkoxy, and —$C_{3-5}$cycloalkyl, where n is 1 or 2. In some embodiments, Z is —$C_{1-6}$alkyl or —$C_{1-6}$haloalkyl, optionally substituted with up to 3 members, each independently selected from the group consisting of: -halo, —OH, —CN, —$CH_2OCH_3$, —$CH_2CH_2OCH_3$, —$N(CH_3)_2$, —$C_{1-6}$alkoxy, —$C_{1-6}$haloalkoxy, and —$C_{3-5}$cycloalkyl, where n is 1 or 2.

Alternatively, treatment of an aminopyrazole of formula (XVII) with an acyl chloride of formula (XIX) provides a pyrazololpyrimidinone analog of formula (XXI). For example, treatment of an aminopyrazole with an acid chloride, in the presence or absence of p-toluenesulfonic acid, in a solvent such as dichloromethane, dioxane or the like, provides a pyrazolopyrimidinone of formula (XXI). In addition, an ester can be used instead of an acid chloride to provide a pyrazolopyrimidinone of formula (XXI). For example, treatment of an aminopyrazole with an ester of formula (XX), in the presence of a base such as sodium t-butoxide or potassium t-butoxide or the like, in a solvent such as dioxane or the like, affords a pyrazolopyrimidinone of formula (XXI), where A is carbon or nitrogen, B is -halo, —$C_{1-6}$alkyl, —$C_{1-6}$haloalkyl, —$C_{1-6}$alkoxy, —$C_{1-6}$haloalkoxy or —$C_{3-5}$cycloalkyl, V is —$C_{3-8}$cycloalkyl, Y is —$C_{1-6}$alkyl, and Z is —$C_{1-6}$alkyl, —$C_{1-6}$haloalkyl, —$C_{1-6}$alkoxy, —$(CH_2)_n$aryl, or —$(CH_2)_n$heteroaryl, said alkyl, aryl and heteroaryl optionally substituted with up to three members. In some embodiments, Z is —$C_{1-6}$alkoxy, —$(CH_2)_n$aryl, or —$(CH_2)_n$heteroaryl, said aryl and heteroaryl optionally substituted with up to 3 members, each independently selected from the group consisting of: -halo, —OH, —CN, —$CH_2OCH_3$, —$CH_2CH_2OCH_3$, —$N(CH_3)_2$, —$C_{1-6}$alkyl, —$C_{1-6}$haloalkyl, —$C_{1-6}$alkoxy, —$C_{1-6}$haloalkoxy, and —$C_{3-5}$cycloalkyl, where n is 1 or 2. In some embodiments, Z is —$C_{1-6}$alkyl or —$C_{1-6}$haloalkyl, optionally substituted with up to 3 members, each independently selected from the group consisting of: -halo, —OH, —CN, —$CH_2OCH_3$, —$CH_2CH_2OCH_3$, —$N(CH_3)_2$, —$C_{1-6}$alkoxy, —$C_{1-6}$haloalkoxy, and —$C_{3-5}$cycloalkyl, where n is 1 or 2.

Additionally, the pyrazolopyrimidinone can be formed using an anhydride. For example, treatment of the aminopyrazole with acetic anhydride, in the presence of PTSA, with or without a solvent, at a temperature ranging from 40° C. to 80° C. for several hours, provides the acyl intermediate. Subsequent addition of a solvent such as methanol or the like, followed by a base, such as potassium bicarbonate, heated to a temperature ranging from 40° C. to 100° C. using traditional or microwave heating, provides a pyrazolopyrimidinone of formula (XXI), where Z is methyl and A is carbon or nitrogen, B is -halo, —$C_{1-6}$alkyl, —$C_{1-6}$haloalkyl, —$C_{1-6}$alkoxy, —$C_{1-6}$haloalkoxy or —$C_{3-5}$cycloalkyl, V is —$C_{3-8}$cycloalkyl, and Y is —$C_{1-6}$alkyl. Or, treatment of the aminopyrazole with acetic anhydride, in an acid, such as acetic acid or the like, at a temperature ranging from 40° C. to 80° C., provides a pyrazolopyrimidinone of formula (XXI). Similarly, the aminopyrazole can be treated with acetic anhydride, in acetic acid, at a temperature ranging from 40° C. to 100° C., to provide the pyrazolopyrimidinone of formula (XXI).

SCHEME D

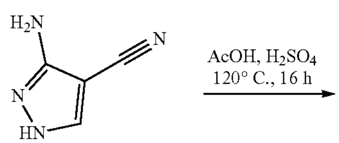

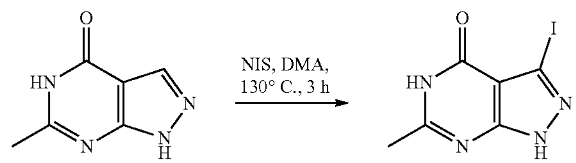

According to Scheme D, 3-iodo-6-methyl-1H-pyrazolo[3,4-d]pyrimidin-4(5H)-one can be synthesized in two steps from 3-amino-1H-pyrazole-4-carbonitrile. Treatment of 3-amino-1H-pyrazole-4-carbonitrile with acid, such as acetic acid and sulfuric acid, at a temperature ranging from 80° C. to 140° C., provides 6-methyl-1H-pyrazolo[3,4-d]pyrimidin-4(5H)-one. Subsequent halogenation, under conditions known to one skilled in the art, such as treatment with NIS, in a solvent such as DMA or DMF or the like, at a temperature ranging from 80° C. to 140° C., provides 3-iodo-6-methyl-1H-pyrazolo[3,4-d]pyrimidin-4(5H)-one.

SCHEME E

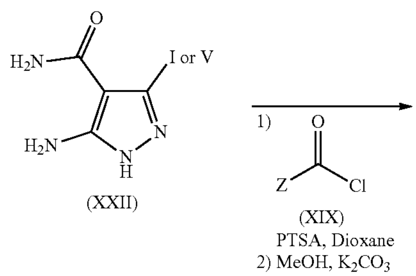

(XXII)

(XIX)

-continued

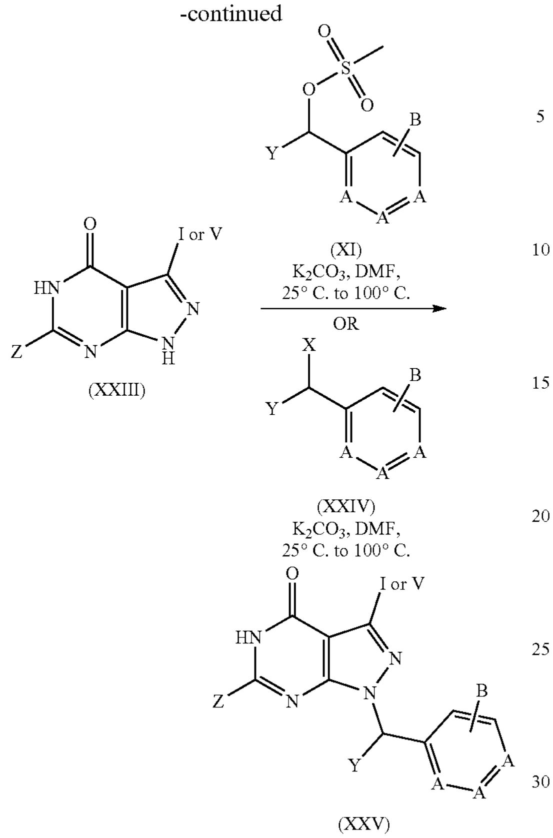

According to Scheme E, compounds of formula (XXV) can be synthesized by a nucleophilic substitution reaction of a pyrazolopyrimidinone of formula (XXIII) with a synthetically accessible mesylate of formula (XI), as shown in Scheme A, or a commercially available or synthetically accessible halide of formula (XXIV), where X is Br, Cl or I.

Treatment of an aminopyrazole of formula (XXII) with an acid chloride of formula (XIX) provides a pyrazololpyrimidinone analog of formula (XXIII), where V is —$C_{3-8}$cycloalkyl and Z is —$C_{1-6}$alkyl, —$C_{1-6}$haloalkyl, —$C_{1-6}$alkoxy, —$(CH_2)_n$aryl, or —$(CH_2)_n$heteroaryl, said alkyl, aryl and heteroaryl optionally substituted with up to three members. In some embodiments, Z is —$C_{1-6}$alkoxy, —$(CH_2)_n$aryl, or —$(CH_2)_n$heteroaryl, said aryl and heteroaryl optionally substituted with up to 3 members, each independently selected from the group consisting of: -halo, —OH, —CN, —$CH_2OCH_3$, —$CH_2CH_2OCH_3$, —$N(CH_3)_2$, —$C_{1-6}$alkyl, —$C_{1-6}$haloalkyl, —$C_{1-6}$alkoxy, —$C_{1-6}$haloalkoxy, and —$C_{3-5}$cycloalkyl, where n is 1 or 2. In some embodiments, Z is —$C_1$-6alkyl or —$C_{1-6}$haloalkyl, optionally substituted with up to 3 members, each independently selected from the group consisting of: -halo, —OH, —CN, —$CH_2OCH_3$, —$CH_2CH_2OCH_3$, —$N(CH_3)_2$, —$C_{1-6}$alkoxy, —$C_{1-6}$haloalkoxy, and —$C_{3-5}$cycloalkyl, where n is 1 or 2. For example, treatment of an aminopyrazole with an acid chloride, with or without p-toluenesulfonic acid, in a solvent such as dioxane or the like, followed by treatment with a base, such as potassium bicarbonate, in a solvent such as methanol or the like, provides a pyrazolopyrimidinone of formula (XXIII). A subsequent nucleophilic substitution reaction, under conditions known to one skilled in the art, such as treatment of the pyrazolopyrimidinone with a mesylate of formula (XI), in the presence of a base, such as potassium carbonate, in a solvent such as DMF or DMA or the like, at a temperature ranging from 25° C. to 100° C. provides a compound of formula (XXV). Alternatively, treatment of a pyrazolopyrimidinone with a halide of formula (XXIV), where X is Br, Cl or I, in the presence of a base, such as potassium carbonate, in a solvent such as DMF or DMA or the like, at a temperature ranging from 25° C. to 100° C. provides a compound of formula (XXV) where A is carbon or nitrogen, B is -halo, —$C_{1-6}$alkyl, —$C_{1-6}$haloalkyl, —$C_{1-6}$alkoxy, —$C_{1-6}$haloalkoxy, or —$C_{3-5}$cycloalkyl, V is —$C_{3-8}$cycloalkyl, Y is —$C_{1-6}$alkyl, and Z is —$C_{1-6}$alkyl, —$C_{1-6}$haloalkyl, —$C_{1-6}$alkoxy, —$(CH_2)_n$aryl, —$(CH_2)_n$heteroaryl, said alkyl, aryl and heteroaryl optionally substituted with up to three members. In some embodiments, Z is —$C_{1-6}$alkoxy, —$(CH_2)_n$aryl, or —$(CH_2)_n$heteroaryl, said aryl and heteroaryl optionally substituted with up to 3 members, each independently selected from the group consisting of: -halo, —OH, —CN, —$CH_2OCH_3$, —$CH_2CH_2OCH_3$, —$N(CH_3)_2$, —$C_{1-6}$alkyl, —$C_{1-6}$haloalkyl, —$C_{1-6}$alkoxy, —$C_{1-6}$haloalkoxy, and —$C_{3-5}$cycloalkyl, where n is 1 or 2. In some embodiments, Z is —$C_{1-6}$alkyl or —$C_{1-6}$haloalkyl, optionally substituted with up to 3 members, each independently selected from the group consisting of: -halo, —OH, —CN, —$CH_2OCH_3$, —$CH_2CH_2OCH_3$, —$N(CH_3)_2$, —$C_{1-6}$alkoxy, —$C_{1-6}$haloalkoxy, and —$C_{3-5}$cycloalkyl, where n is 1 or 2.

SCHEME F

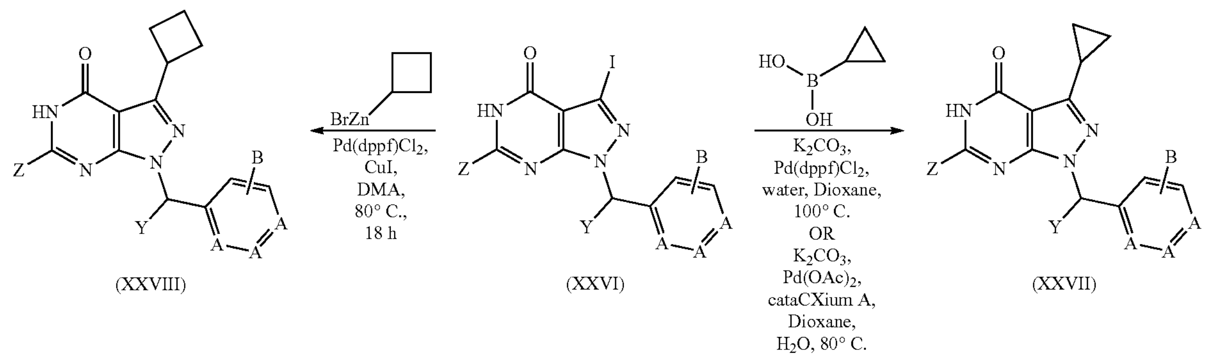

-continued

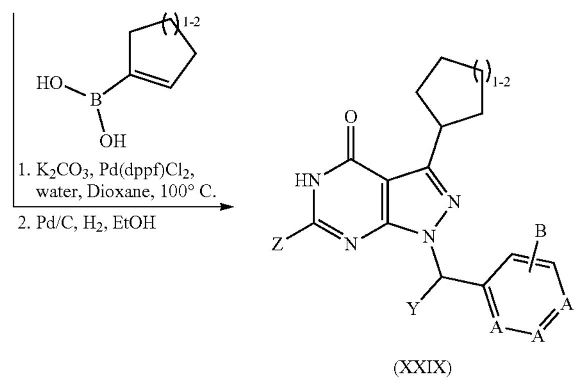

(XXIX)

According to Scheme F, iodo compounds of formula (XXVI), under conditions known to one skilled in the art for an organic coupling reaction, can be converted into cyclopropyl and cyclobutyl analogs. In one instance, Suzuki coupling of the iodo compound with cyclopropylboronic acid, in the presence of a base such as potassium bicarbonate, with a catalyst such as [1,1'-Bis(diphenylphosphino) ferrocene]palladium(II) dichloride or the like, in a solvent mixture such as water and dioxane, at a temperature ranging from 80° C. to 120° C. provides a cyclopropyl of formula (XXVII) where A is carbon or nitrogen, B is -halo, —$C_{1-6}$alkyl, —$C_{1-6}$haloalkyl, —$C_{1-6}$alkoxy, —$C_{1-6}$haloalkoxy, or —$C_{3-5}$cycloalkyl, Y is —$C_{1-6}$alkyl, and Z is —$C_{1-6}$alkyl, —$C_{1-6}$haloalkyl, —$C_{1-6}$alkoxy, —$(CH_2)_n$aryl, —$(CH_2)_n$heteroaryl, said alkyl, aryl and heteroaryl optionally substituted with up to three members. In some embodiments, Z is —$C_{1-6}$alkoxy, —$(CH_2)_n$aryl, or —$(CH_2)_n$heteroaryl, said aryl and heteroaryl optionally substituted with up to 3 members, each independently selected from the group consisting of: -halo, —OH, —CN, —$CH_2OCH_3$, —$CH_2CH_2OCH_3$, —$N(CH_3)_2$, —$C_{1-6}$alkyl, —$C_{1-6}$haloalkyl, —$C_{1-6}$alkoxy, —$C_{1-6}$haloalkoxy, and —$C_{3-5}$cycloalkyl, where n is 1 or 2. In some embodiments, Z is —$C_{1-6}$alkyl or —$C_{1-6}$haloalkyl, optionally substituted with up to 3 members, each independently selected from the group consisting of: -halo, —OH, —CN, —$CH_2OCH_3$, —$CH_2CH_2OCH_3$, —$N(CH_3)_2$, —$C_{1-6}$alkoxy, —$C_{1-6}$haloalkoxy, and —$C_{3-5}$cycloalkyl, where n is 1 or 2. Similarly, a Suzuki coupling, in the presence of a base, such as potassium carbonate or the like, with a catalyst such as palladium(II) acetate and a phosphine ligand such as cataCXium A or the like, in a solvent mixture such as dioxane and water, at a temperature ranging from 40° C. to 100° C. also provides a cyclopropyl analog of formula (XXVII).

In another embodiment, a Negishi coupling with an iodo compound of formula (XXVI) and cyclobutyl zinc bromide, in the presence of a catalyst such as

[1,1'-Bis(diphenylphosphino)ferrocene]palladium(II) dichloride and copper (I) iodide, in a solvent such as DMA or DMF or the like, at a temperature ranging from 60° C. to 140° C. provides a cyclobutyl compound of formula (XXVIII), where A is carbon or nitrogen, B is -halo, —$C_{1-6}$alkyl, —$C_{1-6}$haloalkyl, —$C_{1-6}$alkoxy, —$C_{1-6}$haloalkoxy, or —$C_{3-5}$cycloalkyl, Y is —$C_{1-6}$alkyl, and Z is —$C_{1-6}$alkyl, —$C_{1-6}$haloalkyl, —$C_{1-6}$alkoxy, —$(CH_2)_n$aryl, —$(CH_2)_n$heteroaryl, said alkyl, aryl and heteroaryl optionally substituted with up to three members. In some embodiments, Z is —$C_{1-6}$alkoxy, —$(CH_2)_n$aryl, or —$(CH_2)_n$heteroaryl, said aryl and heteroaryl optionally substituted with up to 3 members, each independently selected from the group consisting of: -halo, —OH, —CN, —$CH_2OCH_3$, —$CH_2CH_2OCH_3$, —$N(CH_3)_2$, —$C_{1-6}$alkyl, —$C_{1-6}$haloalkyl, —$C_{1-6}$alkoxy, —$C_{1-6}$haloalkoxy, and —$C_{3-5}$cycloalkyl, where n is 1 or 2. In some embodiments, Z is —$C_{1-6}$alkyl or —$C_{1-6}$haloalkyl, optionally substituted with up to 3 members, each independently selected from the group consisting of: -halo, —OH, —CN, —$CH_2OCH_3$, —$CH_2CH_2OCH_3$, —$N(CH_3)_2$, —$C_{1-6}$alkoxy, —$C_{1-6}$haloalkoxy, and —$C_{3-5}$cycloalkyl, where n is 1 or 2.

Cyclopentyl or cyclohexyl compounds of formula (XXIX), under conditions known to one skilled in the art for an organic coupling reaction, can be synthesized from an iodo compound of formula (XXVI), by a Suzuki reaction, as previously described, using the appropriate starting material or reagent substitutions, including cyclopenteneboronic acid or cyclohexeneboronic acid, followed by subsequent reduction of the double bond. For instance, reduction of the cyclopentene can be achieved using Pd/C or the like, in a solvent such as methanol or ethanol or the like, in the presence of hydrogen.

SCHEME G

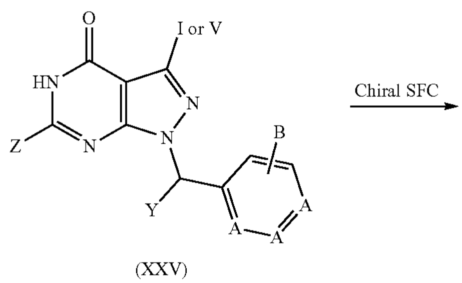

(XXV)

-continued

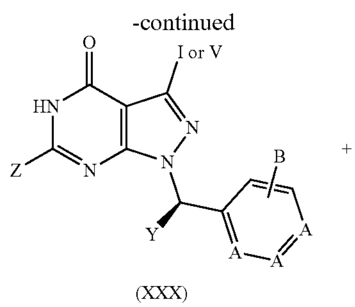

(XXX)

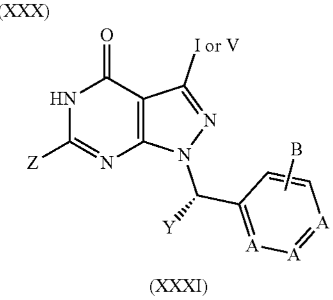

(XXXI)

According to Scheme G, enantiomerically pure compounds of formula (XXX) and (XXXI) can be obtained by chiral separation of the corresponding racemic mixture, where A is carbon or nitrogen, B is -halo, $-C_{1-6}$alkyl, $-C_{1-6}$haloalkyl, $-C_{1-6}$alkoxy, $-C_{1-6}$haloalkoxy, or $-C_{3-5}$cycloalkyl, V is $-C_{3-8}$cycloalkyl, Y is $-C_{1-6}$alkyl, and Z is $-C_{1-6}$alkyl, $-C_{1-6}$haloalkyl, $-C_{1-6}$alkoxy, $-(CH_2)_n$aryl, $-(CH_2)_n$heteroaryl, said alkyl, aryl and heteroaryl optionally substituted with up to three members. In some embodiments, Z is $-C_{1-6}$alkoxy, $-(CH_2)_n$aryl, or $-(CH_2)_n$heteroaryl, said aryl and heteroaryl optionally substituted with up to 3 members, each independently selected from the group consisting of: -halo, —OH, —CN, $-CH_2OCH_3$, $-CH_2CH_2OCH_3$, $-N(CH_3)_2$, $-C_{1-6}$alkyl, $-C_{1-6}$haloalkyl, $-C_{1-6}$alkoxy, $-C_{1-6}$haloalkoxy, and $-C_{3-5}$cycloalkyl, where n is 1 or 2. In some embodiments, Z is $-C_{1-6}$alkyl or $-C_{1-6}$haloalkyl, optionally substituted with up to 3 members, each independently selected from the group consisting of: -halo, —OH, —CN, $-CH_2OCH_3$, $-CH_2CH_2OCH_3$, $-N(CH_3)_2$, $-C_{1-6}$alkoxy, $-C_{1-6}$haloalkoxy, and $-C_{3-5}$cycloalkyl, where n is 1 or 2.

Compounds prepared according to the schemes described above may be obtained as single enantiomers, diastereomers, or regioisomers, by enantio-, diastereo-, or regiospecific synthesis, or by resolution. Where the compounds have at least one chiral center, they may accordingly exist as enantiomers. Where the compounds possess two or more chiral centers, they may additionally exist as diastereomers. It is to be understood that all such isomers and mixtures thereof are encompassed within the scope of the present embodiments. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following examples are provided to further illustrate the embodiments.

Chemistry:

In obtaining the compounds described in the examples below, and the corresponding analytical data, the following experimental and analytical protocols were followed, unless otherwise indicated.

Unless otherwise stated, reaction mixtures were magnetically stirred at room temperature (rt) under nitrogen atmosphere. Where solutions were "dried," they were generally dried over a drying agent such as $Na_2SO_4$ or $MgSO_4$. Where mixtures, solutions, and extracts were "concentrated," they were typically concentrated on a rotary evaporator under reduced pressure.

Reactions Under Microwave Irradiation Conditions were Carried Out in a CEM

Discover-SP with Activent microwave reaction apparatus, model number 909150, or Biotage Initiator, model number 355302.

Normal-phase flash column chromatography (FCC) was performed on Silica ($SiO_2$) using packed or prepackaged cartridges, eluting with the indicated solvents.

The mass spectra (m/z) were recorded using either electrospray ionization (ESI) or atmospheric pressure chemical ionization (APCI). LC/MS were obtained on a Waters 2695 Separations Unit, 2487 Dual Absorbance Detector, Micromass ZQ fitted with ESI Probe, or a Waters Acquity™ Ultra performance LC (UPLC) with PDA eλ and SQ detectors.

Analytical LC-MS was performed on a Waters Acquity™ UPLC-MS instrument equipped with a Acquity UPLC BEH $C_{18}$ column (1.7 μm, 2.1 mm×50 mm) and the solvent system A: 0.1% HCOOH in $H_2O$ and B: 0.1% HCOOH in ACN. Column temperature was 45° C. All compounds were run using the same elution gradient, i.e., 5% to 95% solvent B in 0.75 min with a flow rate of 1 mL/min.

Analytical SFC-MS was performed on a Waters $UPC^2$-MS instrument equipped with a Acquity $UPC^2$ BEH 2-ethylpyridine column (1.7 μm, 2.1 mm×50 mm) and the solvent system A: $CO_2$ and B: 0.1% $NH_4OH$ in MeOH. Column temperature was 55° C. All compound were run using the same elution gradient, i.e., 3% to 35% solvent B in 0.75 min with a flow rate of 2.5 mL/min.

Preparative HPLC was performed on a Shimadzu SIL-10AP system using a Waters SunFire™ OBD 30 mm×100 mm×2.5 μm (particle size) $C^{18}$ column with a 15-minute gradient of 10-100% acetonitrile in water and 0.05% trifluoroacetic acid added as a modifier to both phases. Elution profiles were monitored by UV at 254 and 220 nm.

Some compounds were purified using a Waters Fractionlynx™ system equipped with a XBridge Prep $C_{18}$ OBD column (5 μm, 19 mm×50 mm) and the solvent system: $H_2O$:ACN and 2% TFA in $H_2O$. Specific elution gradients were based on retention times obtained with an analytical UPLC-MS, however, in general all elution gradients of $H_2O$ and ACN were run over a 5.9 min run time with a flow rate of 40 mL/min. An autoblend method was used to ensure a concentration of 0.1% TFA throughout each run.

Preparative SFC-MS was performed using a Waters Prep100 SFC-MS system equipped with a Viridis 2-ethylpyridine OBD column (5 μm, 30 mm×100 mm) and the solvent system: $CO_2$:MeOH and 1% $NH_4OH$ in MeOH. Specific elution gradients were based on retention times obtained with an analytical $UPC^2$-MS, however, in general all elution gradients of $CO_2$ and MeOH were run over a 3.6 min run time with a flow rate of 100 mL/min and a column temperature of 55° C. An autoblend method was used to ensure a concentration of 0.2% $NH_4OH$ throughout each run.

Nuclear magnetic resonance (NMR) spectra were obtained in a Varian 400 MHz or Bruker 400 MHz NMR. Samples were analyzed in either deuterated acetone ($(CD_3)_2CO$), chloroform ($CDCl_3$), methanol-$d_4$ ($CD_3OD$), or dimethyl sulfoxide-$d_6$ (DMSO-d6). For $CDCl_3$ samples, the residual central resonance peak at 7.26 for $^1H$ was used for chemical shift assignment for $^1H$ NMR spectra. For $CD_3OD$ the residual central resonance peak at 3.31 for $^1H$ was used for chemical shift assignment and for DMSO-d6 the residual central resonance peak at 2.50 ppm for $^1H$ was used for chemical shift assignment. The format of the $^1H$ NMR data below is: chemical shift in ppm downfield the tetramethylsilane reference (multiplicity, coupling constant J in Hz, integration), using conventional abbreviations for designation of major peaks: e.g. s, singlet; d, doublet; t, triplet; q, quartet; p, pentet; m, multiplet; br, broad.

Chemical names were generated using ChemDraw Ultra 12.0 (CambridgeSoft Corp., Cambridge, MA) or ChemAxon.

Intermediate 1. (1-(4-(trifluoromethyl)phenyl)ethyl)hydrazine hydrochloride

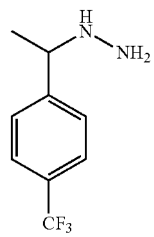

Step A. tert-butyl 2-(1-(4-(trifluoromethyl)phenyl)ethylidene)hydrazinecarboxylate. A solution of 1-(4-(trifluoromethyl)phenyl)ethanone (2.00 g, 10.6 mmol) and tert-butyl carbazate (1.41 g, 10.6 mmol) in toluene (12.5 mL, 0.85 M) was stirred at 75° C. for 18 h. The reaction mixture was cooled to room temperature and stirred for 30 min. The solid was collected, rinsed with toluene (5 mL), and dried to provide the title compound (1.65 g, 52%) as a white solid. $^1H$ NMR (400 MHz, DMSO-$d_6$) δ10.01 (s, 1H), 7.94 (d, J=8.1 Hz, 2H), 7.75 (d, J=8.4 Hz, 2H), 2.24 (s, 3H), 1.50 (s, 9H). [M+H−tBu]=246.96.

Step B. tert-butyl 2-(1-(4-(trifluoromethyl)phenyl)ethyl)hydrazinecarboxylate. A solution of tert-butyl 2-(1-(4-(trifluoromethyl)phenyl)ethylidene)hydrazinecarboxylate (609 mg, 2.01 mmol) and Pd/C (225 mg, 2.11 mmol) in ethanol (10.1 mL, 0.2 M) was stirred under 1 atm of hydrogen at 25° C. for 18 h. The reaction mixture was filtered through a pad of celite, eluting with dichloromethane and concentrated to provide the title compound (575 mg, 94%) as a white solid. $^1H$ NMR (400 MHz, DMSO-$d_6$) δ8.17 (br. s., 1H), 7.66 (d, J=8.2 Hz, 2H), 7.56 (d, J=8.2 Hz, 2H), 4.77 (br. s., 1H), 4.13-4.26 (m, 1H), 1.35 (s, 9H) 1.20 (d, J=7.0 Hz, 3H). [M+H−tBu]=249.00.

Step C. (1-(4-(trifluoromethyl)phenyl)ethyl)hydrazine hydrochloride. A solution of tert-butyl 2-(1-(4-(trifluoromethyl)phenyl)ethyl)hydrazinecarboxylate (400 mg, 1.31 mmol) in methanol (2.63 mL, 0.5 M) and 4 N HCl in dioxane (1.64 mL) was stirred at 25° C. for 3 days. The reaction mixture was concentrated to provide the title compound (521 mg, 100%) as an off-white solid. $^1H$ NMR (400 MHz, DMSO-$d_6$) δ7.76 (d, J=8.2 Hz, 2H), 7.66 (d, J=8.2 Hz, 2H), 5.78 (br. s, 4H), 4.30 (q, J=6.6 Hz, 1H), 1.38 (d, J=6.6 Hz, 3H). [M+H]=204.95.

Intermediate 2. 2-(1-hydrazinylethyl)-5-(trifluoromethyl)pyridine

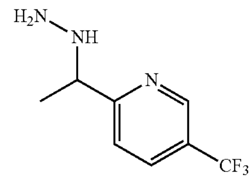

Step A. 1-(5-(trifluoromethyl)pyridin-2-yl)ethanol. To a solution of n-butyllithium (30.4 mL, 1.60 mol/L, 48.7 mmol) in toluene (100 mL) at −78° C. was slowly added a solution of 2-bromo-5-(trifluoromethyl)pyridine (10.0 g, 44.3 mmol) in toluene (50 mL), followed by acetaldehyde (2.73 mL, 48.67 mmol). The resulting mixture was stirred at −78° C. for 5 min and acetic acid (5.07 mL, 88.5 mmol) was added followed by a sat. solution of sodium bicarbonate (50 mL) and a 10% solution of methanol in dichloromethane (100 mL). The aqueous layer was saturated with NaCl and extracted with a solution of 10% methanol in dichloromethane (3×50 mL). The combined organic layer was concentrated under reduced pressure. Purification (FCC, $SiO_2$, 0-40% 10% methanol in EtOAc/Heptanes) afforded the title compound (5.69 mg, 67%) as a beige oil. $^1H$ NMR (400 MHz, DMSO-$d_6$) δ8.87 (d, J=1.0 Hz, 1H), 8.20 (dd, J=8.4, 2.3 Hz, 1H), 7.75 (d, J=8.3 Hz, 1H), 5.60 (d, J=4.6 Hz, 1H), 4.77-4.88 (m, 1H), 1.40 (d, J=6.6 Hz, 3H). [M+H]=192.02.

Step B. 1-(5-(trifluoromethyl)pyridin-2-yl)ethyl methanesulfonate. To a cooled solution of 1-[5-(trifluoromethyl)pyridin-2-yl]propan-1-ol (715 mg, 8.97 mmol) in dichloromethane (44.86 mL) at 0° C. was added methanesulfonic anhydride (1.88 g, 10.7 mmol) followed by 4-methylmorpholine (1.18 mL, 10.8 mmol). The reaction mixture was stirred at 0° C. for 1 h. The reaction mixture was diluted with dichloromethane (25 mL) and water (25 mL). The aqueous layer was extracted with dichloromethane (25 mL). The combined organic layer was dried ($Na_2SO_4$) and concentrated under reduced pressure to provide the title compound. The material was used as such for the next step. [M+H]=269.95.

Step C. 2-(1-hydrazinylethyl)-5-(trifluoromethyl)pyridine. To a cooled solution of 1-[5-(trifluoromethyl)pyridin-2-yl]ethyl methanesulfonate (2.42 g, 8.97 mmol) in methanol (25 mL) at 0° C. was added hydrazine (1.97 mL, 62.8 mmol). The mixture was stirred at 0-25° C. for 18 h and concentrated under reduced pressure. The mixture was diluted with 1 N HCl (20 mL) and washed with hexanes (20 mL). The aqueous layer was neutralized with NaOH (800 mg, 20 mmol) and extracted with dichloromethane (3×20 mL). The combined organic layer was dried ($Na_2SO_4$) and concentrated under reduced pressure to provide the title compound (1.58 g, 86%) as a brown oil. $^1$H NMR (400 MHz, DMSO-$d_6$) δ8.88 (s, 1H), 8.16 (d, J=8.3 Hz, 1H), 7.68 (d, J=8.3 Hz, 1H), 3.93 (q, J=6.8 Hz, 1H), 1.22 (d, J=6.8 Hz, 3H). [M+H]=206.11.

Intermediate 3 to Intermediate 5 were prepared in a manner analogous to Intermediate 2, using the appropriate starting material and reagent substitutions.

Intermediate 3. 5-(1-hydrazinylpropyl)-2-(trifluoromethyl)pyridine

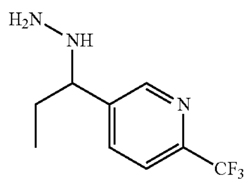

[M+H]=220.06.

Intermediate 4. 5-(1-hydrazinylethyl)-2-(trifluoromethyl)pyridine

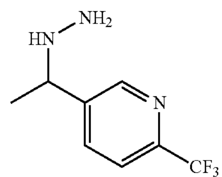

[M+H]=206.09.

Intermediate 5. 2-(1-hydrazinylpropyl)-5-(trifluoromethyl)pyridine

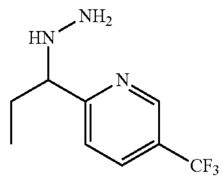

$^1$H NMR (400 MHz, DMSO-$d_6$) δppm 8.90 (s, 1H), 8.16 (d, J=8.3 Hz, 1H), 7.65 (d, J=8.3 Hz, 1H), 3.76 (t, J=6.6 Hz, 1H), 1.50-1.73 (m, 2H), 0.77 (t, J=7.5 Hz, 3H). [M+H] =220.05.

Intermediate 6. 2-(cyclopropyl(methoxy)methylene)malononitrile

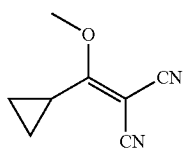

To a solution of sodium hydride (5.81 g, 145 mmol) in tetrahydrofuran (121 mL) at 0° C. was slowly added malononitrile (8.00 g, 121 mmol) in tetrahydrofuran (20 mL). The reaction mixture was stirred at 0-25° C. for 1 h. The reaction mixture was cooled to 0° C. and a solution of cyclopropanecarbonyl chloride (12.7 g, 121 mmol) in THF (10 mL) was slowly added. The reaction mixture was stirred at 0-25° C. for 18 h. The reaction mixture was diluted in 1 N aq. hydrochloric acid (150 mL) and ethyl acetate (100 mL). The aqueous layer was extracted with ethyl acetate (2×100 mL). The combined organic layer was dried ($Na_2SO_4$) and concentrated under reduced pressure to provide crude 2-(cyclopropyl(hydroxy)methylene)malononitrile (19.7 g, 100%) as a light brown oil. The crude material was used without further purification. To a solution of sodium hydride (1.45 g, 36.3 mmol) in THF (60 mL, 0.5 M) at 0° C. was slowly added crude 2-(cyclopropyl(hydroxy) methylene)malononitrile (8.12 g, 60.5 mmol) in THF (30 mL). The reaction mixture was stirred at 0-25° C. for 30 min. The reaction mixture was cooled to 0° C. and a solution of dimethyl sulfate (7.64 g, 60.5 mmol) in THF (30 mL) was slowly added. The reaction mixture was stirred at 25° C. for 18 h then at 50° C. for 48 h. The reaction mixture was diluted with ethyl acetate (150 mL) and saturated aqueous sodium hydrogen carbonate (150 mL). The layers were separated and the aqueous layer was extracted with ethyl acetate (2×50 mL). The combined organic layers were washed with brine (25 mL), dried ($Na_2SO_4$) and concentrated under reduced pressure. Purification (FCC, $SiO_2$, 0-40% EtOAc/Heptanes) afforded the title compound (4.07 g, 26%) as a colorless oil. $^1$H NMR (400 MHz, CHLOROFORM-d) δ4.29 (s, 3H), 2.12-2.23 (m, 1H), 1.12-1.21 (m, 4H). [M+H]=148.90.

Intermediate 7. 5-amino-3-cyclopropyl-1-(1-(6-(trifluoromethyl)pyridin-3-yl)propyl)-1H-pyrazole-4-carboxamide

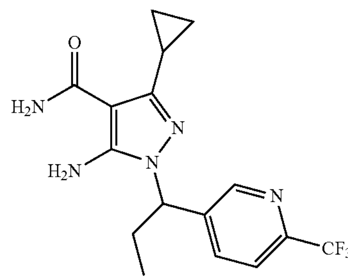 [SMILES: CCC(c1ccc(C(F)(F)F)nc1)n1nc(C2CC2)c(C(N)=O)c1N]

Step A. 5-amino-3-cyclopropyl-1-(1-(6-(trifluoromethyl) pyridin-3-yl) propyl)-1H-pyrazole-4-carbonitrile. A solution of 5-(1-hydrazinylpropyl)-2-(trifluoromethyl)pyridine (1.60 g, 7.31 mmol), triethylamine (5.10 mL, 36.5 mmol) and 2-(cyclopropyl(methoxy)methylene)malononitrile (1.08 g, 7.31 mmol) in ethanol (14.6 mL) was stirred at 60° C. for 18 h. The reaction mixture was diluted with dichloromethane (50 mL) and 1 N aq. ammonium chloride (25 mL). The aqueous layer was extracted with dichloromethane (2×25 mL). The combined organic layer was dried ($Na_2SO_4$) and concentrated under reduced pressure. Purification (FCC, $SiO_2$, 0-30% 10% methanol in EtOAc/Heptanes) afforded the title compound (1.20 g, 49%) as a beige oil. $^1$H NMR (400 MHz, DMSO-$d_6$) δ8.72 (s, 1H), 7.91-7.96 (m, 2H), 6.71 (s, 2H), 5.35 (dd, J=9.7, 5.4 Hz, 1H), 2.18-2.26 (m, 1H), 2.00-2.10 (m, 2H), 0.78-0.86 (m, 7H). [M+H]=336.11.

Step B. 5-amino-3-cyclopropyl-1-(1-(6-(trifluoromethyl) pyridin-3-yl) propyl)-1H-pyrazole-4-carboxamide. To a solution of 5-amino-3-cyclopropyl-1-(1-(6-(trifluoromethyl) pyridin-3-yl) propyl)-1H-pyrazole-4-carbonitrile (1.20 g, 3.56 mmol) in methanol (5.94 mL) at 0° C. was added 1 M aq. sodium hydroxide (3.92 mL, 3.92 mmol) followed by a 30% solution of hydrogen peroxide in water (2.02 mL, 17.8 mmol). The reaction mixture was stirred at 0-25° C. for 18 h. The reaction mixture was diluted in dichloromethane (25 mL) and sat. $Na_2S_2O_3$ (25 mL). The aqueous layer was extracted with dichloromethane (2×25 mL). The combined organic layer was dried ($Na_2SO_4$) and concentrated under reduced pressure to provide the title compound (1.15 g, 91%) as a beige oil. [M+H]=354.11.

Intermediate 8. 5-amino-3-cyclopropyl-1-(1-(6-(trifluoromethyl)pyridin-3-yl)ethyl)-1H-pyrazole-4-carboxamide

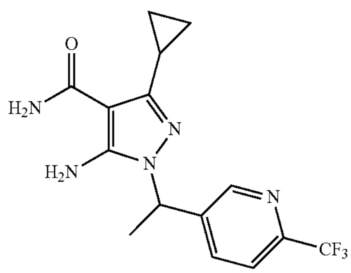 [SMILES: CC(c1ccc(C(F)(F)F)nc1)n1nc(C2CC2)c(C(N)=O)c1N]

The title compound was prepared in a manner analogous to Intermediate 7, using the appropriate starting material and reagent substitutions. The product was obtained as a yellow solid. $^1$H NMR (400 MHz, $CD_3OD$) δ8.56 (s, 1H) 7.83-7.90 (m, 1H) 7.77-7.83 (m, 1H) 5.59 (q, J=7.1 Hz, 1H) 1.90-2.00 (m, 1H) 1.85 (d, J=7.1 Hz, 3H) 0.84-1.00 (m, 4H). [M+H]=340.09.

Intermediate 9. 3-iodo-6-methyl-1H-pyrazolo[3,4-d]pyrimidin-4(5H)-one

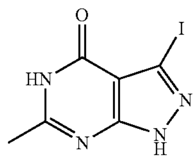

Step A. 6-methyl-1H-pyrazolo[3,4-d]pyrimidin-4 (5H)-one. To a stirred suspension of 3-amino-1H-pyrazole-4-carbonitrile (150 g, 1.39 mol) in acetic acid (300 mL) was added $H_2SO_4$ (300 mL) drop wise over a period of 30 min at 10° C. Reaction mixture was heated to 120° C. for 16 h. The reaction mixture was cooled to 25° C. and poured into ice (1 kg) and basified with a sat. aq. solution of $Na_2CO_3$. The precipitated solid was filtered and washed with water (300 mL), dried under reduced pressure and co-distilled with toluene to provide the title compound (200 g, 96%) as an off-white solid. $^1$H NMR (300 MHz, DMSO-$d_6$) δ13.2-12.2 (br. s., 1H), 8.01 (s, 1H), 3.7-3.1 (br. s., 1H), 2.32 (s, 3H). [M+H]=151.1.

Step B. 3-Iodo-6-methyl-1,5-dihydro-4H-pyrazolo[3,4-d]pyrimidin-4-one. To a stirred suspension of 6-methyl-1H-pyrazolo[3,4-d]pyrimidin-4 (5H)-one (80.0 g, 533 mmol) in dimethyl acetamide (800 mL) was added N-iodosuccinimide (180 g, 799 mmol) portion-wise over a period of 30 min. The reaction mixture was heated to 130° C. for 3 hours. The reaction mixture was cooled to 0° C. and poured into a saturated aqueous solution of $Na_2S_2O_3$ (1.8 L) with stirring. The mixture was allowed to settle for 3 h and the precipitated brown solid was filtered. The isolated brown solid was suspended in THF:$CH_3CN$:MeOH:$H_2O$ (3:3:2:3) and stirred for 16 h. The resulting solid was filtered and dried under vacuum to provide the title compound (60 g, 41%) as a brown solid. $^1$H NMR (400 MHz, DMSO-$d_6$) δ13.02 (s, 1H), 12.04 (s, 1H), 2.32 (s, 3H). [M+H]=276.9.

Intermediate 10. 3-iodo-6-methyl-1-(1-(5-(trifluoromethyl)pyridin-2-yl)ethyl)-1H-pyrazolo[3,4-d]pyrimidin-4(5H)-one

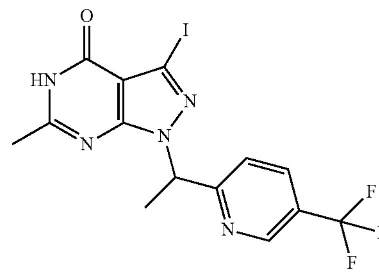

Step A. 1-(5-(trifluoromethyl)pyridin-2-yl) ethanol. To a cooled solution of n-butyllithium (30.4 mL, 1.60 mol/L, 48.7 mmol) in toluene (148 mL) at −78° C. was slowly added 2-bromo-5-(trifluoromethyl)pyridine (10.0 g, 44.3 mmol) in toluene (50 mL) over 30 min, followed by acetaldehyde (2.73 mL, 48.7 mmol) over 5 min. The reaction mixture was stirred at −78° C. for 30 min. Acetic acid (5.07 mL, 88.7 mmol) was added followed by a sat. aqueous solution of sodium bicarbonate (50 mL) and a 10% solution of methanol in dichloromethane (100 mL). The combined organic layer was dried ($Na_2SO_4$) and concentrated under reduced pressure. The residue was purified by FCC (0-40%, 10% methanol in ethyl acetate/heptane), then concentrated under reduced pressure to provide the title compound as a beige oil (5.69 g, 67%). $^1$H NMR (400 MHz, DMSO-$d_6$) δ8.87 (d, J=1.0 Hz, 1H), 8.20 (dd, J=8.4, 2.3 Hz, 1H), 7.75 (d, J=8.3 Hz, 1H), 5.60 (d, J=4.6 Hz, 1H), 4.77-4.88 (m, 1H), 1.40 (d, J=6.6 Hz, 3H). [M+H]=192.02.

Step B. 1-(5-(trifluoromethyl)pyridin-2-yl)ethyl methanesulfonate. To a solution of 1-(5-(trifluoromethyl)pyridin-2-yl)ethanol (1.0 g, 5.23 mmol) in dichloromethane (26.2 mL) at 0° C. was added methanesulfonic anhydride (1.09 g, 6.28 mmol) followed by 4-methylmorpholine (0.69 mL, 6.28 mmol). The reaction mixture was stirred at 0° C. for 18 h. Additional methanesulfonic anhydride (825 mg, 4.71 mmol) followed by 4-methylmorpholine (517 μL, 5.65 mmol) was added and the reaction mixture was stirred for an additional 24 h at a temperature ranging from 0° C. to 25° C. The reaction mixture was diluted with water (15 mL) and dichloromethane (10 mL). The aqueous layer was extracted with dichloromethane (2×15 mL), dried ($Na_2SO_4$) and concentrated under reduced pressure to provide the title compound as a brown oil. [M+H]=270.09.

Step C. 3-iodo-6-methyl-1-(1-(5-(trifluoromethyl)pyridin-2-yl)ethyl)-1H-pyrazolo[3,4-d]pyrimidin-4(5H)-one. A solution of 3-iodo-6-methyl-1,5-dihydro-4H-pyrazolo[3,4-d]pyrimidin-4-one (1.40 g, 5.22 mmol), potassium carbonate (793 mg, 5.74 mmol), and 1-(5-(trifluoromethyl)pyridin-2-yl)ethyl methanesulfonate (1.40 g, 5.22 mmol) in N,N-dimethylformamide (17.4 mL) was stirred at 50° C. for 18 h then 25° C. for 24 h. Additional 3-iodo-6-methyl-1H,4H,5H-pyrazolo[3,4-d]pyrimidin-4-one (288 mg, 1.04 mmol) and potassium carbonate (160 mg, 1.15 mmol) were added and the reaction was stirred at 50° C. for an additional 4 h. A mixture of 1 N aq. ammonium chloride (7 mL), water (20 mL), and methanol (5 mL) was added slowly at 50° C. The mixture was allowed to slowly cool to 25° C. with stirring over 8 h. The solid was collected and washed with water (5 mL) and heptanes (2×5 mL). The solid was dried in a vacuum oven (40° C. for 18 h) to provide the title compound (1.51 g, 64%) as a white solid. $^1$H NMR (400 MHz, DMSO-$d_6$) δ12.21 (s, 1H), 8.94 (s, 1H), 8.20 (dd, J=8.3, 1.9 Hz, 1H), 7.36 (d, J=8.3 Hz, 1H), 6.12 (q, J=7.1 Hz, 1H), 2.34 (s, 3H), 1.90 (d, J=7.1 Hz, 3H). [M+H]=450.06.

Intermediate 11 to Intermediate 14 were prepared in a manner analogous to Intermediate 10, with the appropriate starting material substitutions.

Intermediate 11. 3-iodo-6-methyl-1-(1-(4-(trifluoromethyl)phenyl)ethyl)-1H-pyrazolo[3,4-d]pyrimidin-4(5H)-one

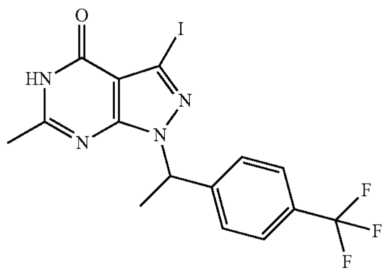 [SMILES: Cc1nc2c(c(I)nn2C(C)c2ccc(C(F)(F)F)cc2)c(=O)[nH]1]

$^1$H NMR (400 MHz, DMSO-$d_6$) δ7.72 (d, J=8.3 Hz, 2H), 7.48 (d, J=8.3 Hz, 2H), 6.08 (q, J=6.9 Hz, 1H), 2.34 (s, 3H) 1.85 (d, J=7.1 Hz, 3H). [M+H]=449.01.

Intermediate 12. 3-iodo-6-methyl-1-(1-(5-(trifluoromethyl)pyridin-2-yl)ethyl)-1H-pyrazolo[3,4-d]pyrimidin-4(5H)-one

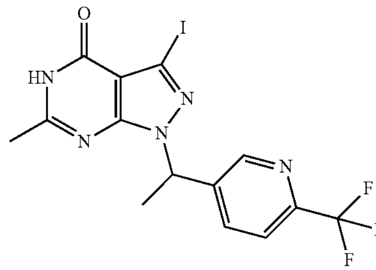

$^1$H NMR (400 MHz, $CD_3OD$) δ8.74 (s, 1H), 8.05 (d, J=8.3 Hz, 1H), 7.82 (d, J=8.3 Hz, 1H), 6.23 (q, J=6.8 Hz, 1H), 2.45 (s, 3H) 1.99 (d, J=7.1 Hz, 3H). [M+H]=449.97.

Intermediate 13. 3-iodo-6-methyl-1-(1-(5-(trifluoromethyl)pyridin-2-yl)propyl)-1H-pyrazolo[3,4-d]pyrimidin-4(5H)-one

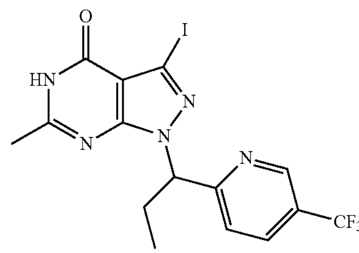 [SMILES: CCC(c1ccc(C(F)(F)F)cn1)n1nc(I)c2c(=O)[nH]c(C)nc21]

$^1$H NMR (400 MHz, DMSO-$d_6$) δ12.22 (br. s., 1H), 8.94 (s, 1H), 8.21 (dd, J=8.4, 2.3 Hz, 1H), 7.45 (d, J=8.3 Hz, 1H), 5.86 (t, J=7.7 Hz, 1H), 2.36-2.45 (m, 2H), 2.35 (s, 3H), 0.82 (t, J=7.2 Hz, 3H). [M+H]=464.09.

Intermediate 14. 3-iodo-6-methyl-1-(1-(6-(trifluoromethyl)pyridin-3-yl)propyl)-1H-pyrazolo[3,4-d]pyrimidin-4(5H)-one

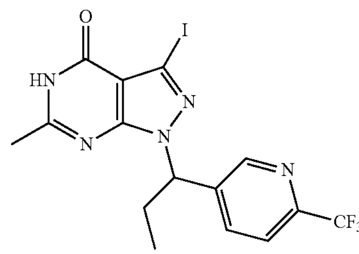 [SMILES: CCC(c1ccc(C(F)(F)F)nc1)n1nc(I)c2c(=O)[nH]c(C)nc21]

$^1$H NMR (400 MHz, DMSO-$d_6$) δ12.22 (s, 1H), 8.81 (s, 1H), 8.05 (d, J=6.7 Hz, 1H), 7.91 (d, J=8.2 Hz, 1H), 5.91 (dd, J=9.9, 5.5 Hz, 1H), 2.39-2.47 (m, 1H), 2.37 (s, 3H), 2.20-2.30 (m, 1H), 0.80 (t, J=7.2 Hz, 3H). [M+H]=464.47.

SPECIFIC EXAMPLES

Example 1. 3-cyclopropyl-6-[(5-methoxypyridin-2-yl)methyl]-1-{1-[6-(trifluoromethyl)pyridin-3-yl]propyl}-1H,4H,5H-pyrazolo[3,4-d]pyrimidin-4-one

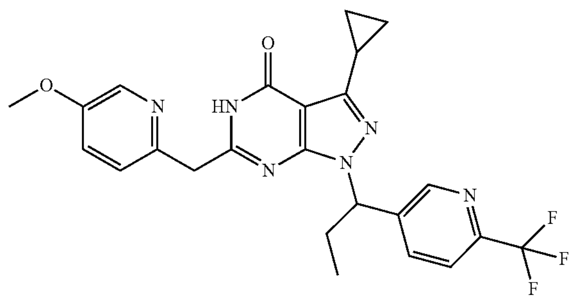 [SMILES: CCC(c1ccc(C(F)(F)F)nc1)n1nc(C2CC2)c2c(=O)[nH]c(Cc3ccc(OC)cn3)nc21]

To a cooled solution of 5-amino-3-cyclopropyl-1-{1-[6-(trifluoromethyl)pyridin-3-yl]propyl}-1H-pyrazole-4-carboxamide (300 mg, 0.85 mmol), ethyl 2-(5-methoxypyridin-2-yl)acetate (166 mg, 0.85 mmol) and 4 Å molecular sieve pellets (~0.1 g) in dioxane (5.66 mL) at 0° C. was slowly added sodium tert-butoxide (0.64 mL, 2.00 mol/L, 1.27 mmol). The reaction mixture was stirred at 55° C. under an atmosphere of nitrogen for 20 h. The reaction mixture was cooled to 0° C. then additional sodium tert-butoxide (0.32 mL) was added slowly. After 5 min at 0° C. the reaction mixture was stirred at 55° C. under nitrogen for 3 h. The mixture was diluted with TFA (250 μL) and MeOH, then filtered. The filtrate was purified (reverse-phase prep-HPLC, C-18) to give the title compound as a beige solid (60 mg, 15%). $^1$H NMR (400 MHz, $CD_3OD$) δ8.66 (d, J=1.3 Hz, 1H), 8.21 (d, J=2.7 Hz, 1H), 8.02 (dd, J=8.2, 1.6 Hz, 1H), 7.75 (d, J=8.2 Hz, 1H), 7.42 (dd, J=8.5, 3.0 Hz, 1H), 7.37 (d, J=8.5 Hz, 1H), 5.76 (dd, J=10.2, 5.7 Hz, 1H), 4.15 (s, 2H), 3.90 (s, 3H), 2.46-2.57 (m, 1H), 2.34-2.41 (m, 1H), 2.16-2.28 (m, 1H), 1.09-1.15 (m, 2H), 0.98-1.03 (m, 2H), 0.85 (t, J=7.3 Hz, 3H). [M+H]=485.26.

Example 2. 3-cyclopropyl-6-[(5-methoxypyridin-2-yl)methyl]-1-{1-[6-(trifluoromethyl)pyridin-3-yl]ethyl}-1H,4H,5H-pyrazolo[3,4-d]pyrimidin-4-one

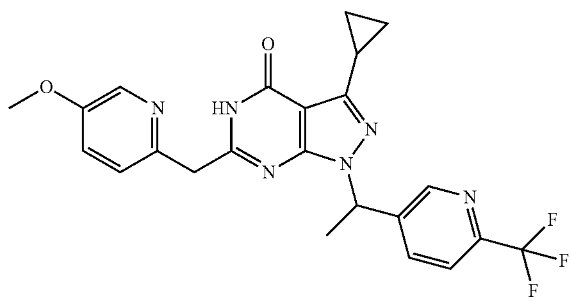 [SMILES: COc1ccc(Cc2nc3c(c(C4CC4)nn3C(C)c3ccc(C(F)(F)F)nc3)c(=O)[nH]2)nc1]

Example 2 was prepared in a manner analogous to Example 1, using the appropriate starting material and reagent substitutions. $^1$H NMR (400 MHz, $CD_3OD$) δ8.59 (br. s., 1H), 8.20 (d, J=2.4 Hz, 1H), 7.93 (d, J=8.6 Hz, 1H), 7.74 (d, J=8.1 Hz, 1H), 7.39-7.44 (m, 1H), 7.34-7.38 (m, 1H), 6.04 (dd, J=14.2, 7.1 Hz, 1H), 4.13 (s, 2H), 3.90 (s, 3H), 2.35 (d, J=5.4 Hz, 1H), 1.91 (d, J=7.1 Hz, 3H), 1.12 (d, J=1.7 Hz, 2H), 1.00 (dd, J=8.6, 2.7 Hz, 2H). [M+H]=471.16.

Example 3. 3-cyclopropyl-6-methyl-1-{1-[6-(trifluoromethyl)pyridin-3-yl]propyl}-1H,4H,5H-pyrazolo[3,4-d]pyrimidin-4-one

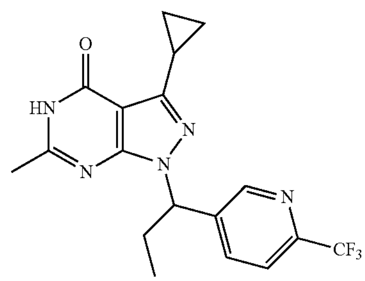 [SMILES: CCC(c1ccc(C(F)(F)F)nc1)n1nc(C2CC2)c2c(=O)[nH]c(C)nc21]

A solution of 3-iodo-6-methyl-1-(1-(6-(trifluoromethyl)pyridin-3-yl)propyl)-1H-pyrazolo[3,4-d]pyrimidin-4(5H)-one (1.00 g, 2.16 mmol), cyclopropylboronic acid (315 mg, 3.67 mmol), potassium carbonate (746 mg, 5.40 mmol), and Pd(dppf)$Cl_2$ (88 mg, 0.11 mmol) in dioxane (10.8 mL) and water (2.50 mL) was stirred at 90° C. for 4 h. Additional Pd(dppf)$Cl_2$ (40 mg, 0.05 mmol) was added and the reaction mixture was stirred at 90° C. for an additional 18 h. Additional Pd(dppf)$Cl_2$ (40 mg, 0.05 mmol) was added and the reaction mixture was stirred at 95° C. for 18 h. The reaction mixture was diluted with a solution of 10% methanol in dichloromethane (20 mL) and an aqueous solution of ammonium chloride (1 N, 5.4 mL). The aqueous layer was extracted with 10% methanol in dichloromethane (2×10 mL). The combined organic layer was dried ($Na_2SO_4$) and concentrated under reduced pressure. Purification (FCC, $SiO_2$, 5-30% 10% methanol in EtOAc/Heptanes) afforded the title compound (542 mg, 67%) as an off-white solid. $^1$H NMR (400 MHz, $CD_3OD$) δ8.76 (d, J=1.8 Hz, 1H), 8.11 (dd, J=8.1, 2.1 Hz, 1H), 7.80 (d, J=8.2 Hz, 1H), 5.87 (dd, J=10.3, 5.4 Hz, 1H), 2.48-2.62 (m, 1H), 2.44 (s, 3H), 2.34-2.41 (m, 1H), 2.20-2.31 (m, 1H), 1.10-1.15 (m, 2H), 0.97-1.04 (m, 2H), 0.88 (t, J=7.3 Hz, 3H). [M+H]=378.20.

Example 4. 3-cyclobutyl-6-methyl-1-{1-[6-(trifluoromethyl)pyridin-3-yl]propyl}-1H,4H,5H-pyrazolo[3,4-d]pyrimidin-4-one

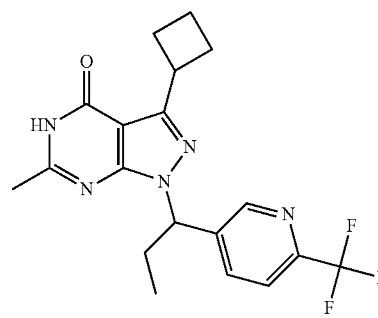

To a solution of 3-iodo-6-methyl-1-{1-[6-(trifluoromethyl)pyridin-3-yl]propyl}-1H,4H,5H-pyrazolo[3,4-d]pyrimidin-4-one (30 mg, 0.06 mmol), [1,1'-Bis(diphenylphosphino)ferrocene]dichloropalladium(II) (5.29 mg, 0.01 mmol) and copper (I) iodide (6.17 mg, 0.03 mmol) in dimethyl acetamide (323.84 μL) under nitrogen was added cyclobutyl zinc bromide (194 μL, 0.50 mol/L, 0.10 mmol). The mixture was stirred at 80° C. for 18 h. Additional [1,1'-Bis(diphenylphosphino)ferrocene]dichloropalladium (II) (5.29 mg, 0.01 mmol), copper(I) iodide (6.17 mg, 0.03 mmol) and cyclobutyl zinc bromide (400 μL, 0.50 mol/L, 0.21 mmol) were added and the mixture was stirred at 80° C. for 18 h. Purification (reverse-phase prep-HPLC, C18) afforded the title compound (3.5 mg, 14%) as a beige solid. $^1$H NMR (400 MHz, $CD_3OD$) δ8.80 (d, J=1.7 Hz, 1H), 8.16 (dd, J=8.1, 1.9 Hz, 1H), 7.81 (d, J=8.2 Hz, 1H), 5.91 (dd, J=10.2, 5.4 Hz, 1H), 3.92 (quin, J=8.7 Hz, 1H), 2.48-2.66 (m, 3H), 2.45 (s, 3H) 2.22-2.41 (m, 3H), 1.91-2.15 (m, 2H), 0.90 (t, J=7.3 Hz, 3H). [M+H]=392.24.

Example 5 and 6. 3-cyclopropyl-6-[(5-methoxypyridin-2-yl)methyl]-1-[(1S)-1-[6-(trifluoromethyl)pyridin-3-yl]ethyl]-1H,4H,5H-pyrazolo[3,4-d]pyrimidin-4-one and 3-cyclopropyl-6-[(5-methoxypyridin-2-yl)methyl]-1-[(1R)-1-[6-(trifluoromethyl)pyridin-3-yl]ethyl]-1H,4H,5H-pyrazolo[3,4-d]pyrimidin-4-one

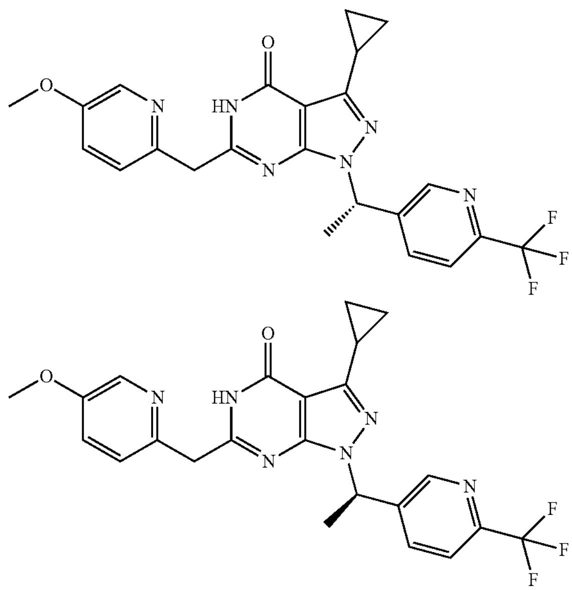

Racemic 3-cyclopropyl-6-((5-methoxypyridin-2-yl)methyl)-1-(1-(6-(trifluoromethyl)pyridin-3-yl)ethyl)-1H-pyrazolo[3,4-d]pyrimidin-4(5H)-one (Example 2, 31 mg) was resolved by preparative SFC using a Chiralpak IA column (30×150 mm, 5 μm) eluting with 15% MeOH/$CO_2$ (1500 psi) to provide the two pure enantiomers. The first eluted compound, Example 5 (5 mg, 16%, >95% ee), was isolated as a white solid. $^1$H NMR (400 MHz, $CD_3OD$) δ8.59 (d, J=1.5 Hz, 1H), 8.20 (d, J=2.8 Hz, 1H), 7.93 (dd, J=8.2, 1.7 Hz, 1H), 7.74 (d, J=8.2 Hz, 1H), 7.41 (dd, J=8.5, 2.8 Hz, 1H), 7.35 (d, J=8.5 Hz, 1H), 6.04 (q, J=7.2 Hz, 1H), 4.13 (s, 2H), 3.90 (s, 3H), 2.31-2.42 (m, 1H), 1.91 (d, J=7.2 Hz, 3H), 1.07-1.16 (m, 2H), 0.96-1.04 (m, 2H). [M+H]=471.21. The second eluted compound, Example 6 (6 mg, 19%, >95% ee), was isolated as a white solid. $^1$H NMR (400 MHz, $CD_3OD$) δ8.59 (d, J=1.5 Hz, 1H), 8.20 (d, J=2.8 Hz, 1H), 7.93 (dd, J=8.3, 1.8 Hz, 1H), 7.74 (d, J=8.2 Hz, 1H), 7.41 (dd, J=8.5, 2.8 Hz, 1H), 7.35 (d, J=8.5 Hz, 1H), 6.04 (q, J=7.2 Hz, 1H), 4.13 (s, 2H), 3.90 (s, 3H), 2.36 (tt, J=8.5, 5.2 Hz, 1H), 1.91 (d, J=7.1 Hz, 3H), 1.07-1.16 (m, 2H), 0.96-1.03 (m, 2H). [M+H]=471.23.

Example 7 to Example 8 were prepared in a manner analogous to Example 1, using the appropriate starting material and reagent substitutions.

Example 7. 3-cyclopropyl-6-[(5-fluoropyridin-2-yl)methyl]-1-{1-[6-(trifluoromethyl)pyridin-3-yl]ethyl}-1H,4H,5H-pyrazolo[3,4-d]pyrimidin-4-one

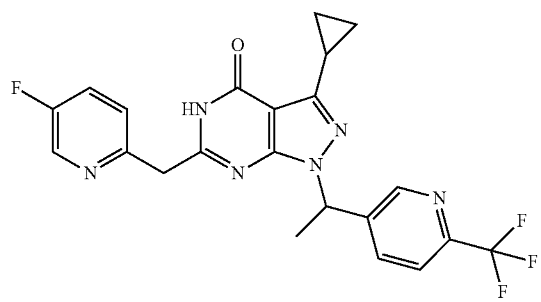 [SMILES: CC(c1ccc(C(F)(F)F)nc1)n1nc(C2CC2)c2c(=O)[nH]c(Cc3ccc(F)cn3)nc21]

$^1$H NMR (400 MHz, $CD_3OD$) δ8.59 (s, 1H), 8.42 (br. s., 1H), 7.93 (d, J=8.1 Hz, 1H), 7.75 (d, J=8.3 Hz, 1H), 7.59-7.66 (m, 2H), 7.48 (dd, J=8.7, 4.5 Hz, 1H), 6.00-6.07 (m, 1H), 4.20 (s, 2H), 2.33-2.40 (m, 1H), 1.91 (d, J=7.1 Hz, 3H), 1.12 (br. s., 2H), 1.01 (d, J=8.3 Hz, 2H). [M+H]=459.14.

Example 8. 3-cyclopropyl-6-[(5-fluoropyridin-2-yl)methyl]-1-{1-[6-(trifluoromethyl)pyridin-3-yl]propyl}-1H,4H,5H-pyrazolo[3,4-d]pyrimidin-4-one

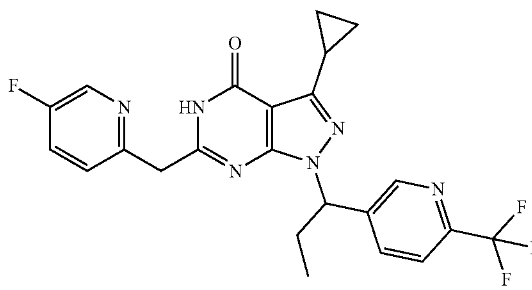

$^1$H NMR (400 MHz, $CD_3OD$) δ8.66 (d, J=1.8 Hz, 1H), 8.43 (d, J=2.9 Hz, 1H), 8.02 (dd, J=8.2, 2.1 Hz, 1H), 7.76 (d, J=8.2 Hz, 1H), 7.64 (td, J=8.6, 2.9 Hz, 1H), 7.49 (dd, J=8.6, 4.5 Hz, 1H), 5.75 (dd, J=10.1, 5.5 Hz, 1H), 4.22 (s, 2H), 2.45-2.56 (m, 1H), 2.38 (s, 1H), 2.15-2.28 (m, 1H), 1.09-1.15 (m, 2H), 0.97-1.04 (m, 2H), 0.84 (t, J=7.3 Hz, 3H). [M+H]=473.22.

Example 9-Example 12 were prepared in a manner analogous to Example 3, with the appropriate starting material and reagent substitutions.

Example 9. 3-cyclopropyl-6-methyl-1-{1-[5-(trifluoromethyl)pyridin-2-yl]propyl}-1H,4H,5H-pyrazolo[3,4-d]pyrimidin-4-one

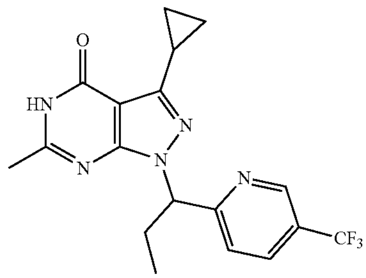 [SMILES: CCC(c1ccc(C(F)(F)F)cn1)n1nc(C2CC2)c2c(=O)[nH]c(C)nc21]

The title compound was prepared in a manner similar to Example 3 using palladium acetate, di((3S,5S,7S)-adamantan-1-yl)(butyl)phosphine and the appropriate starting material substitutions. $^1H$ NMR (400 MHz, DMSO-$d_6$) δ12.02 (s, 1H), 8.94 (s, 1H), 8.18 (dd, J=8.4, 2.1 Hz, 1H), 7.35 (d, J=8.4 Hz, 1H), 5.78 (t, J=7.7 Hz, 1H), 2.24-2.43 (m, 6H), 1.01-1.08 (m, 2H), 0.91-0.99 (m, 2H), 0.80 (t, J=7.3 Hz, 3H). [M+H]=378.19.

Example 10. 3-cyclopropyl-6-methyl-1-{1-[4-(trifluoromethyl)phenyl]ethyl}-1H,4H,5H-pyrazolo[3,4-d]pyrimidin-4-one

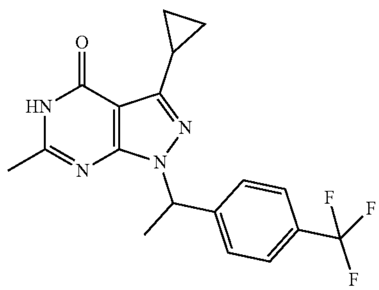 [SMILES: Cc1nc2c(c(C3CC3)nn2C(C)c2ccc(C(F)(F)F)cc2)c(=O)[nH]1]

$^1H$ NMR (400 MHz, $CD_3OD$) δ7.62 (d, J=8.1 Hz, 2H), 7.49 (d, J=8.1 Hz, 2H), 6.08 (q, J=7.1 Hz, 1H), 2.42 (s, 3H), 2.36 (tt, J=8.5, 5.1 Hz, 1H), 1.91 (d, J=7.1 Hz, 3H), 1.13 (dt, J=5.0, 2.6 Hz, 2H), 1.00 (dd, J=8.6, 2.7 Hz, 2H). [M+H]=363.13.

Example 11. 3-cyclopropyl-6-methyl-1-{1-[5-(trifluoromethyl)pyridin-2-yl]ethyl}-1H,4H,5H-pyrazolo[3,4-d]pyrimidin-4-one

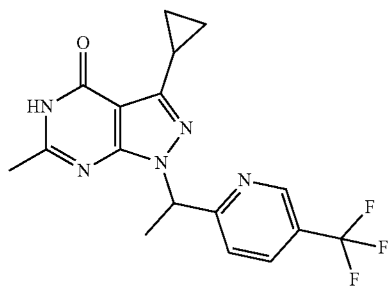 [SMILES: Cc1nc2c(c(C3CC3)nn2C(C)c2ccc(C(F)(F)F)cn2)c(=O)[nH]1]

$^1H$ NMR (400 MHz, $CD_3OD$), δ8.84 (s, 1H), 8.05 (dd, J=8.6, 2.2 Hz, 1H), 7.26 (d, J=8.3 Hz, 1H), 6.14 (q, J=7.1 Hz, 1H), 2.41 (s, 3H), 2.32-2.39 (m, 1H), 1.96 (d, J=7.3 Hz, 3H), 1.09-1.15 (m, 2H), 0.96-1.02 (m, 2H). [M+H]=364.13.

Example 12. 3-cyclopropyl-6-methyl-1-{1-[6-(trifluoromethyl)pyridin-3-yl]ethyl}-1H,4H,5H-pyrazolo[3,4-d]pyrimidin-4-one

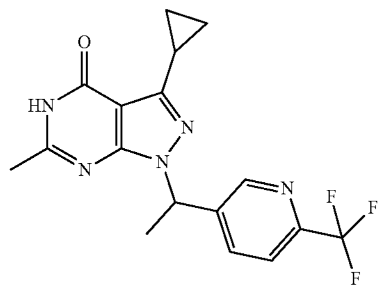 [SMILES: Cc1nc2c(c(C3CC3)nn2C(C)c2ccc(C(F)(F)F)nc2)c(=O)[nH]1]

$^1H$ NMR (400 MHz, $CD_3OD$) δ8.69 (s, 1H), 8.01 (d, J=8.3 Hz, 1H), 7.79 (d, J=8.1 Hz, 1H), 6.17 (q, J=7.3 Hz, 1H), 2.43 (s, 3H), 2.37 (tt, J=8.3, 5.2 Hz, 1H), 1.94 (d, J=7.1 Hz, 3H), 1.07-1.16 (m, 2H), 1.00 (dd, J=8.6, 2.4 Hz, 2H). [M+H]=364.08.

Example 13-Example 26 were prepared in a manner analogous to Example 5 and 6, using the appropriate chiral column and mobile phase to achieve complete separation of the two enantiomers.

Example 13 and 14. 3-cyclopropyl-6-methyl-1-[(1S)-1-[6-(trifluoromethyl)pyridin-3-yl]ethyl]-1H,4H,5H-pyrazolo[3,4-d]pyrimidin-4-one and 3-cyclopropyl-6-methyl-1-[(1R)-1-[6-(trifluoromethyl)pyridin-3-yl]ethyl]-1H,4H,5H-pyrazolo[3,4-d]pyrimidin-4-one

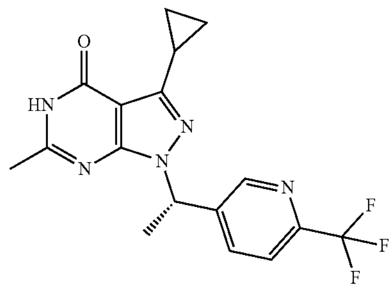

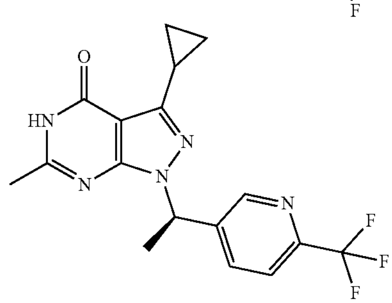

Racemic 3-cyclopropyl-6-methyl-1-(1-(6-(trifluoromethyl)pyridin-3-yl)ethyl)-1H-pyrazolo[3,4-d]pyrimidin-4

(5H)-one (Example 12, 73 mg) was resolved by preparative SFC using a Chiralpak OJ column (30×150 mm, 5 μm) eluting with 20% MeOH/$CO_2$ (1500 psi) to provide the two pure enantiomers. The first eluted compound, Example 13 (22 mg, 30%, >95% ee), was isolated as a white solid. $^1$H NMR (400 MHz, $CD_3OD$) δ8.69 (d, J=1.7 Hz, 1H), 8.01 (dd, J=8.2, 1.7 Hz, 1H), 7.79 (d, J=8.2 Hz, 1H), 6.16 (q, J=7.1 Hz, 1H), 2.43 (s, 3H), 2.31-2.40 (m, 1H), 1.94 (d, J=7.2 Hz, 3H), 1.08-1.16 (m, 2H), 0.95-1.04 (m, 2H). [M+H]=346.10. The second eluted compound, Example 14 (21 mg, 28%, >95% ee), was isolated as a white solid. $^1$H NMR (400 MHz, $CD_3OD$) δ8.69 (d, J=1.6 Hz, 1H), 8.01 (dd, J=8.1, 1.8 Hz, 1H), 7.79 (d, J=8.2 Hz, 1H), 6.17 (q, J=7.1 Hz, 1H), 2.43 (s, 3H), 2.37 (tt, J=8.5, 5.1 Hz, 1H), 1.94 (d, J=7.1 Hz, 3H), 1.06-1.17 (m, 2H), 0.95-1.04 (m, 2H). [M+H]=346.08.

Example 15 and 16. 3-cyclopropyl-6-[(5-fluoropyridin-2-yl)methyl]-1-[(1S)-1-[6-(trifluoromethyl)pyridin-3-yl]ethyl]-1H,4H,5H-pyrazolo[3,4-d]pyrimidin-4-one and 3-cyclopropyl-6-[(5-fluoropyridin-2-yl)methyl]-1-[(1R)-1-[6-(trifluoromethyl)pyridin-3-yl]ethyl]-1H,4H,5H-pyrazolo[3,4-d]pyrimidin-4-one

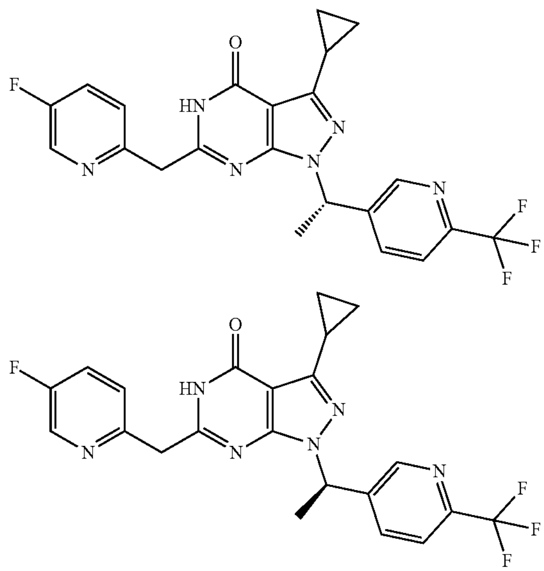

Racemic 3-cyclopropyl-6-((5-fluoropyridin-2-yl)methyl)-1-(1-(6-(trifluoromethyl)pyridin-3-yl)ethyl)-1H-pyrazolo[3,4-d]pyrimidin-4(5H)-one (Example 7, 25 mg) was resolved by preparative SFC using a Chiralpak OJ column (30×150 mm, 5 μm) eluting with 20% MeOH/$CO_2$ (1500 psi) to provide the two pure enantiomers. The first eluted compound, Example 15 (3 mg, 20%, >95% ee), was isolated as a white solid. $^1$H NMR (400 MHz, $CD_3OD$) δ8.59 (d, J=1.7 Hz, 1H), 8.42 (d, J=2.9 Hz, 1H), 7.93 (dd, J=8.2, 2.1 Hz, 1H), 7.75 (d, J=8.2 Hz, 1H), 7.63 (td, J=8.5, 2.9 Hz, 1H), 7.48 (dd, J=8.7, 4.4 Hz, 1H), 6.04 (q, J=7.1 Hz, 1H), 4.21 (s, 2H), 2.36 (tt, J=8.5, 5.1 Hz, 1H), 1.91 (d, J=7.2 Hz, 3H), 1.09-1.15 (m, 2H), 0.97-1.04 (m, 2H). [M+H]=459.18. The second eluted compound, Example 16 (5 mg, 20%, >95% ee), was isolated as a white solid. $^1$H NMR (400 MHz, $CD_3OD$) δ8.59 (s, 1H), 8.41 (d, J=2.8 Hz, 1H), 7.93 (dd, J=8.2, 1.6 Hz, 1H), 7.75 (d, J=8.2 Hz, 1H), 7.62 (td, J=8.5, 2.8 Hz, 1H), 7.48 (dd, J=8.7, 4.4 Hz, 1H), 6.04 (q, J=7.1 Hz, 1H), 4.21 (s, 2H), 2.36 (tt, J=8.5, 5.1 Hz, 1H), 1.91 (d, J=7.2 Hz, 3H), 1.07-1.17 (m, 2H), 0.96-1.04 (m, 2H). [M+H]=459.18.

Example 17 and 18. 3-cyclopropyl-6-[(5-methoxypyridin-2-yl)methyl]-1-[(1S)-1-[6-(trifluoromethyl)pyridin-3-yl]propyl]-1H,4H,5H- pyrazolo[3,4-d]pyrimidin-4-one and 3-cyclopropyl-6-[(5-methoxypyridin-2-yl)methyl]-1-[(1R)-1-[6-(trifluoromethyl)pyridin-3-yl]propyl]-1H,4H,5H-pyrazolo[3,4-d]pyrimidin-4-one

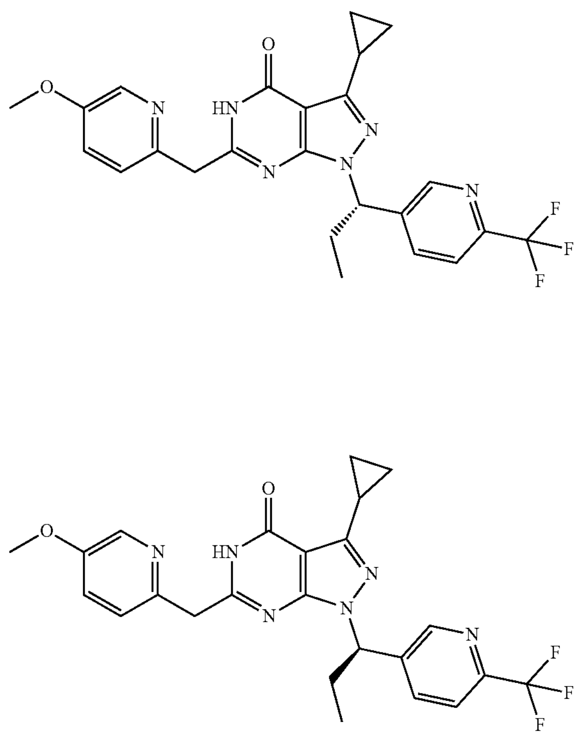 [SMILES: CC[C@@H](c1ccc(C(F)(F)F)nc1)n1nc(C2CC2)c2c(=O)[nH]c(Cc3ccc(OC)cn3)nc21 ; CC[C@H](c1ccc(C(F)(F)F)nc1)n1nc(C2CC2)c2c(=O)[nH]c(Cc3ccc(OC)cn3)nc21]

Racemic 3-cyclopropyl-6-((5-methoxypyridin-2-yl)methyl)-1-(1-(6-(trifluoromethyl)pyridin-3-yl) propyl)-1H-pyrazolo[3,4-d]pyrimidin-4(5H)-one (Example 1, 57 mg) was resolved by preparative SFC using a Chiralpak OJ column (30×150 mm, 5 μm) eluting with 20% MeOH/$CO_2$ (1500 psi) to provide the two pure enantiomers. The first eluted compound, Example 17 (16 mg, 28%, >95% ee), was isolated as a beige semi-solid. $^1$H NMR (400 MHz, $CD_3OD$) δ8.66 (d, J=1.7 Hz, 1H), 8.21 (d, J=2.8 Hz, 1H), 8.02 (dd, J=8.2, 2.0 Hz, 1H), 7.75 (d, J=8.2 Hz, 1H), 7.42 (dd, J=8.7, 2.8 Hz, 1H), 7.37 (d, J=8.7 Hz, 1H), 5.76 (dd, J=10.1, 5.5 Hz, 1H), 4.15 (s, 2H), 3.90 (s, 3H), 2.45-2.58 (m, 1H), 2.31-2.43 (m, 1H), 2.15-2.28 (m, 1H), 1.08-1.16 (m, 2H), 0.96-1.04 (m, 2H), 0.85 (t, J=7.2 Hz, 3H). [M+H]=485.19. The second eluted compound, Example 18 (14 mg, 25%, >95% ee), was isolated as a beige semi-solid. $^1$H NMR (400 MHz, $CD_3OD$) δ8.66 (d, J=1.6 Hz, 1H), 8.21 (d, J=2.7 Hz, 1H), 8.02 (dd, J=8.1, 1.8 Hz, 1H), 7.75 (d, J=8.2 Hz, 1H), 7.42 (dd, J=8.7, 2.8 Hz, 1H), 7.37 (d, J=8.7 Hz, 1H), 5.76 (dd, J=10.1, 5.5 Hz, 1H), 4.15 (s, 2H), 3.90 (s, 3H), 2.45-2.58 (m, 1H), 2.37 (tt, J=8.4, 5.1 Hz, 1H), 2.14-2.28 (m, 1H), 1.08-1.15 (m, 2H), 0.96-1.04 (m, 2H), 0.85 (t, J=7.3 Hz, 3H). [M+H]=485.21.

Example 19 and 20. 3-cyclopropyl-6-methyl-1-[(1S)-1-[6-(trifluoromethyl)pyridin-3-yl]propyl]-1H,4H,5H-pyrazolo[3,4-d]pyrimidin-4-one and 3-cyclopropyl-6-methyl-1-[(1R)-1-[6-(trifluoromethyl)pyridin-3-yl]propyl]-1H,4H,5H-pyrazolo[3,4-d]pyrimidin-4-one

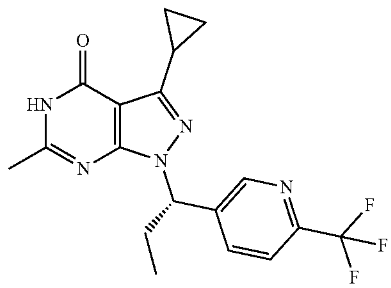

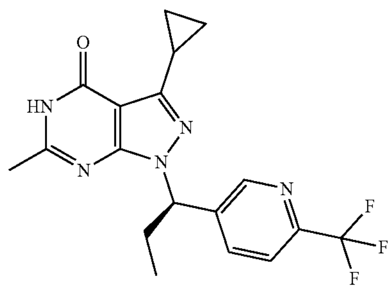

Racemic 3-cyclopropyl-6-methyl-1-(1-(6-(trifluoromethyl)pyridin-3-yl) propyl)-1H-pyrazolo[3,4-d]pyrimidin-4(5H)-one (Example 3, 548 mg) was resolved by preparative SFC using a Chiralpak OJ column (30×150 mm, 5 μm) eluting with 20% $MeOH/CO_2$ (1500 psi) to provide the two pure enantiomers. The first eluted compound, Example 19 (111 mg, 20%, >95% ee), was isolated as a white solid. $^1H$ NMR (400 MHz, $CD_3OD$) δ8.76 (d, J=1.8 Hz, 1H), 8.11 (dd, J=8.2, 2.1 Hz, 1H), 7.80 (d, J=8.2 Hz, 1H), 5.87 (dd, J=10.3, 5.4 Hz, 1H), 2.47-2.58 (m, 1H), 2.44 (s, 3H), 2.38 (tt, J=8.4, 5.1 Hz, 1H), 2.19-2.31 (m, 1H), 1.09-1.16 (m, 2H), 0.98-1.05 (m, 2H), 0.88 (t, J=7.3 Hz, 3H). [M+H]=378.07. The second eluted compound, Example 20 (108 mg, 20%, >95% ee), was isolated as a white solid. $^1H$ NMR (400 MHz, $CD_3OD$) δ8.76 (d, J=1.5 Hz, 1H), 8.11 (dd, J=8.1, 1.7 Hz, 1H), 7.80 (d, J=8.2 Hz, 1H), 5.87 (dd, J=10.3, 5.4 Hz, 1H), 2.48-2.59 (m, 1H), 2.44 (s, 3H), 2.38 (tt, J=8.4, 5.1 Hz, 1H), 2.19-2.31 (m, 1H), 1.09-1.15 (m, 2H), 0.98-1.04 (m, 2H), 0.88 (t, J=7.3 Hz, 3H). [M+H]=378.07.

Example 21 and 22. 3-cyclopropyl-6-[(5-fluoropyridin-2-yl)methyl]-1-[(1S)-1-[6-(trifluoromethyl)pyridin-3-yl]propyl]-1H,4H,5H- pyrazolo[3,4-d]pyrimidin-4-one and 3-cyclopropyl-6-[(5-fluoropyridin-2-yl)methyl]-1-[(1R)-1-[6-(trifluoromethyl)pyridin-3-yl]propyl]-1H,4H,5H-pyrazolo[3,4-d]pyrimidin-4-one

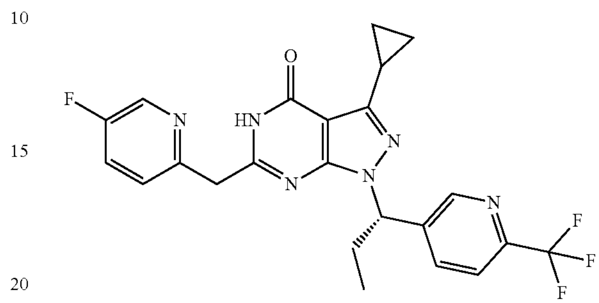

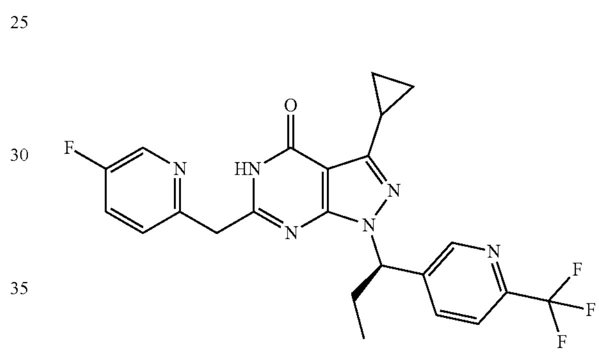

Racemic 3-cyclopropyl-6-((5-fluoropyridin-2-yl)methyl)-1-(1-(6-(trifluoromethyl)pyridin-3-yl) propyl)-1H-pyrazolo[3,4-d]pyrimidin-4(5H)-one (Example 8, 250 mg) was resolved by preparative SFC using a Chiralpak OJ column (30×150 mm, 5 μm) eluting with 20% $MeOH/CO_2$ (1500 psi) to provide the two pure enantiomers. The first eluted compound, Example 21 (50 mg, 39%, >95% ee), was isolated as an off-white solid. $^1H$ NMR (400 MHz, $CD_3OD$) δ8.66 (d, J=1.7 Hz, 1H), 8.43 (d, J=2.9 Hz, 1H), 8.02 (dd, J=8.2, 2.0 Hz, 1H), 7.76 (d, J=8.2 Hz, 1H), 7.64 (td, J=8.5, 3.0 Hz, 1H), 7.50 (dd, J=8.7, 4.4 Hz, 1H), 5.75 (dd, J=10.2, 5.6 Hz, 1H), 4.22 (s, 2H), 2.44-2.56 (m, 1H), 2.38 (tt, J=8.4, 5.1 Hz, 1H), 2.15-2.28 (m, 1H), 1.09-1.16 (m, 2H), 0.97-1.04 (m, 2H), 0.84 (t, J=7.3 Hz, 3H). [M+H]=473.19. The second eluted compound, Example 22 (48 mg, 37%, >95% ee), was isolated as an off-white solid. $^1H$ NMR (400 MHz, $CD_3OD$) δ8.66 (s, 1H), 8.43 (d, J=2.8 Hz, 1H), 8.02 (d, J=8.2 Hz, 1H), 7.76 (d, J=8.2 Hz, 1H), 7.64 (td, J=8.6, 2.9 Hz, 1H), 7.49 (dd, J=8.7, 4.4 Hz, 1H), 5.75 (dd, J=10.1, 5.5 Hz, 1H), 4.22 (s, 2H), 2.43-2.58 (m, 1H), 2.33-2.42 (m, 1H), 2.14-2.28 (m, 1H), 1.08-1.16 (m, 2H), 0.96-1.05 (m, 2H), 0.84 (t, J=7.3 Hz, 3H). [M+H]=473.17.

Example 23 and 24. 3-cyclopropyl-6-methyl-1-[(1S)-1-[5-(trifluoromethyl)pyridin-2-yl]propyl]-1H,4H,5H-pyrazolo[3,4-d]pyrimidin-4-one and 3-cyclopropyl-6-methyl-1-[(1R)-1-[5-(trifluoromethyl)pyridin-2-yl]propyl]-1H,4H,5H-pyrazolo[3,4-d]pyrimidin-4-one

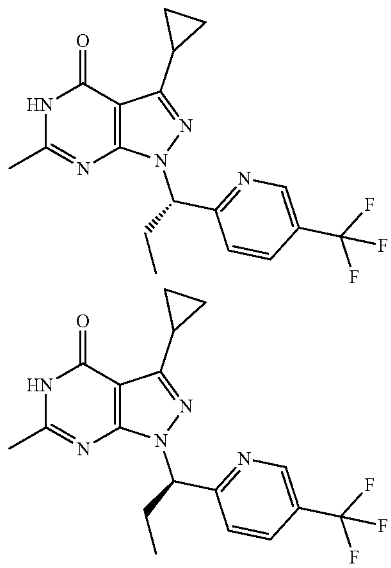

Racemic 3-cyclopropyl-6-methyl-1-(1-(5-(trifluoromethyl)pyridin-2-yl) propyl)-1H-pyrazolo[3,4-d]pyrimidin-4(5H)-one (Example 9, 442 mg) was resolved by preparative SFC using a Chiralpak OJ column (30×150 mm, 5 μm) eluting with 20% MeOH/$CO_2$ (1500 psi) to provide the two pure enantiomers. The first eluted compound, Example 23 (190 mg, 43%, >98% ee), was isolated as a white solid. $^1H$ NMR (400 MHz, DMSO-$d_6$), δ12.02 (s, 1H), 8.94 (d, J=0.9 Hz, 1H), 8.17 (dd, J=8.4, 2.1 Hz, 1H), 7.35 (d, J=8.3 Hz, 1H), 5.78 (t, J=7.8 Hz, 1H), 2.23-2.42 (m, 6H), 1.00-1.08 (m, 2H), 0.90-0.99 (m, 2H), 0.79 (t, J=7.3 Hz, 3H). [M+H]=378.16. The second eluted compound, Example 24 (176 mg, 40%, >98% ee), was isolated as a white solid. $^1H$ NMR (400 MHz, DMSO-$d_6$), δ12.01 (s, 1H), 8.94 (s, 1H), 8.18 (dd, J=8.4, 2.3 Hz, 1H), 7.34 (d, J=8.3 Hz, 1H), 5.69-5.87 (m, 1H), 2.34-2.41 (m, 2H), 2.33 (s, 3H), 2.21-2.31 (m, 1H), 1.01-1.10 (m, 2H), 0.91-0.99 (m, 2H), 0.79 (t, J=7.3 Hz, 3H). [M+H]=378.32.

Example 25 and 26. 3-cyclopropyl-6-methyl-1-[(1S)-1-[5-(trifluoromethyl)pyridin-2-yl]ethyl]-1H,4H,5H-pyrazolo[3,4-d]pyrimidin-4-one and 3-cyclopropyl-6-methyl-1-[(1R)-1-[5-(trifluoromethyl)pyridin-2-yl]ethyl]-1H,4H,5H-pyrazolo[3,4-d]pyrimidin-4-one

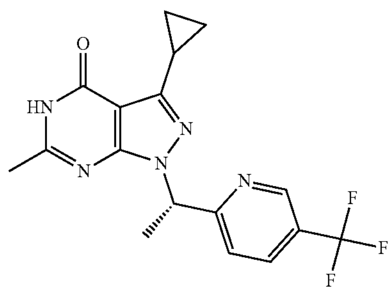

-continued

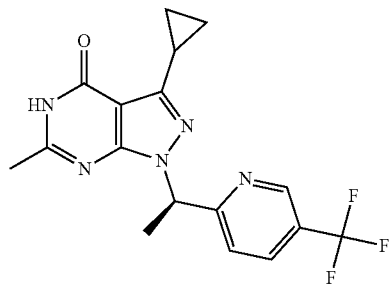

Racemic 3-cyclopropyl-6-methyl-1-(1-(5-(trifluoromethyl)pyridin-2-yl)ethyl)-1H-pyrazolo[3,4-d]pyrimidin-4(5H)-one (Example 11, 795 mg) was resolved by preparative SFC using a Chiralpak OJ column (30×150 mm, 5 μm) eluting with 10% MeOH (0.1% $NH_4OH$)/$CO_2$ (1500 psi) to provide the two pure enantiomers. The first eluted compound, Example 25 (341 mg, 43%, >98% ee), was isolated as an off-white solid. $^1H$ NMR (400 MHz, $CD_3OD$) δ8.84 (d, J=0.9 Hz, 1H), 8.05 (dd, J=8.4, 2.1 Hz, 1H), 7.26 (d, J=8.4 Hz, 1H), 6.14 (q, J=7.2 Hz, 1H), 2.41 (s, 3H), 2.31-2.39 (m, 1H), 1.96 (d, J=7.2 Hz, 3H), 1.09-1.16 (m, 2H), 0.95-1.03 (m, 2H). [M+H]=364.34. The second eluted compound, Example 26 (318 mg, 40%, >98% ee), was isolated as an off-white solid. $^1H$ NMR (400 MHz, $CD_3OD$) δ8.84 (s, 1H), 8.05 (dd, J=8.4, 2.3 Hz, 1H), 7.26 (d, J=8.4 Hz, 1H), 6.15 (q, J=7.1 Hz, 1H), 2.41 (s, 3H), 2.31-2.39 (m, 1H), 1.97 (d, J=7.2 Hz, 3H), 1.09-1.17 (m, 2H), 0.95-1.03 (m, 2H). [M+H]=364.28.

Example 27 to Example 31 can be prepared in a manner analogous to Example 1, using the appropriate starting material and reagent substitutions.

Example 27. 3-cyclopropyl-6-((5-methylpyridin-2-yl)methyl)-1-(1-(5-(trifluoromethyl)pyridin-2-yl)propyl)-1H-pyrazolo[3,4-d]pyrimidin-4(5H)-one

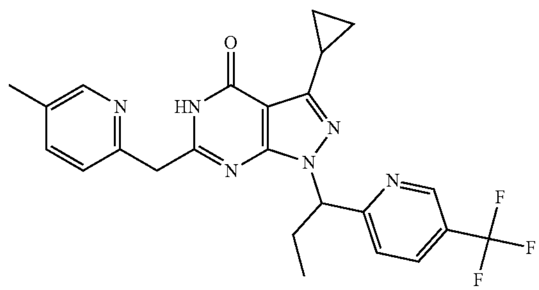 [SMILES: CCC(c1ccc(C(F)(F)F)cn1)n1nc(C2CC2)c2c(=O)[nH]c(Cc3ccc(C)cn3)nc21]

Example 28. 3-cyclopropyl-6-((2-methyloxazol-5-yl)methyl)-1-(1-(5-5 (trifluoromethyl)pyridin-2-yl) propyl)-1H-pyrazolo[3,4-d]pyrimidin-4(5H)-one

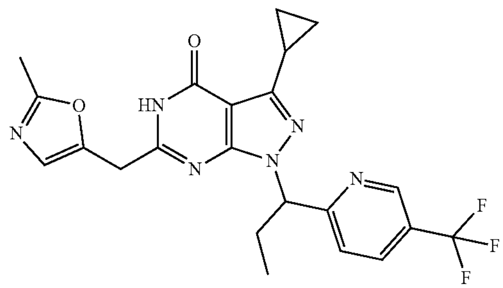 [SMILES: CCC(c1ccc(C(F)(F)F)cn1)n1nc(C2CC2)c2c(=O)[nH]c(Cc3cnc(C)o3)nc21]

Example 29. 3-cyclopropyl-6-(4-(2-methoxyethoxy) benzyl)-1-(1-(pyridin-2-yl)propyl)-1H-pyrazolo[3,4-d]pyrimidin-4(5H)-one

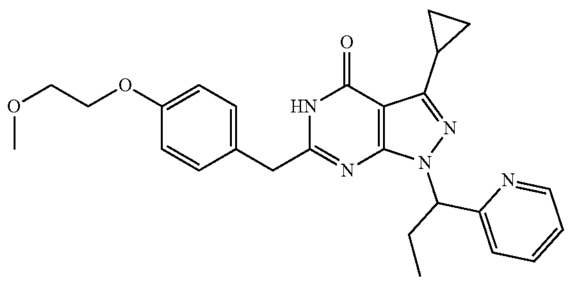 [SMILES: CCC(c1ccccn1)n1nc(C2CC2)c2c(=O)[nH]c(Cc3ccc(OCCOC)cc3)nc21]

Example 30. 3-cyclopropyl-1-(1-(5-(trifluoromethyl)pyridin-2-yl)propyl)-6-((2-(trifluoromethyl) thiazol-4-yl)methyl)-1H-pyrazolo[3,4-d]pyrimidin-4 (5H)-one

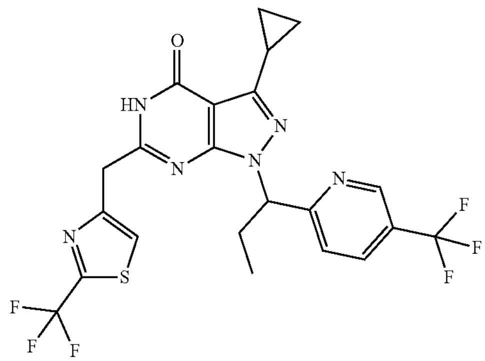 [SMILES: CCC(c1ccc(C(F)(F)F)cn1)n1nc(C2CC2)c2c(=O)[nH]c(Cc3csc(C(F)(F)F)n3)nc21]

Example 31. 3-cyclopropyl-6-(2-(1-methyl-1H-pyrazol-4-yl)ethyl)-1-(1-(5-(trifluoromethyl)pyridin-2-yl)propyl)-1H-pyrazolo[3,4-d]pyrimidin-4(5H)-one

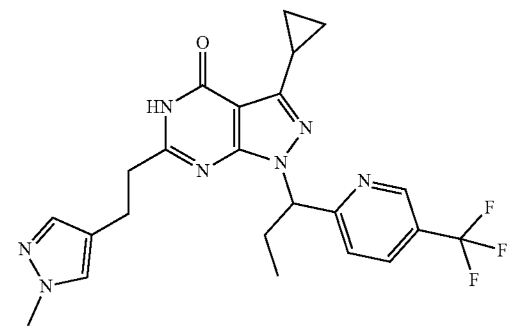 [SMILES: CCC(c1ccc(C(F)(F)F)cn1)n1nc(C2CC2)c2c(=O)[nH]c(CCc3cnn(C)c3)nc21]

Example 32. 3-cyclopropyl-6-(2,2,2-trifluoroethyl)-1-(1-(5-(trifluoromethyl)pyridin-2-yl)propyl)-1H-pyrazolo[3,4-d]pyrimidin-4(5H)-one

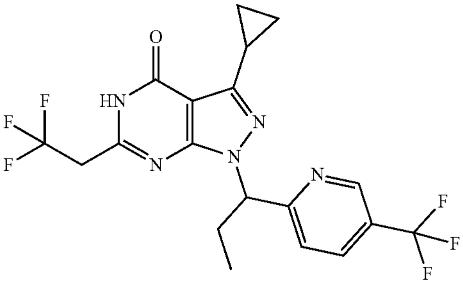 [SMILES: CCC(c1ccc(C(F)(F)F)cn1)n1nc(C2CC2)c2c(=O)[nH]c(CC(F)(F)F)nc21]

The title compound can be made according to Scheme C, using 3,3,3-trifluoropropanoyl chloride and 5-amino-3-cyclopropyl-1-(1-(5-(trifluoromethyl)pyridin-2-yl)propyl)-1H-pyrazole-4-carboxamide.

Example 33. 3-cyclopropyl-6-(trifluoromethyl)-1-(1-(5-(trifluoromethyl)pyridin-2-yl)propyl)-1H-pyrazolo[3,4-d]pyrimidin-4(5H)-one

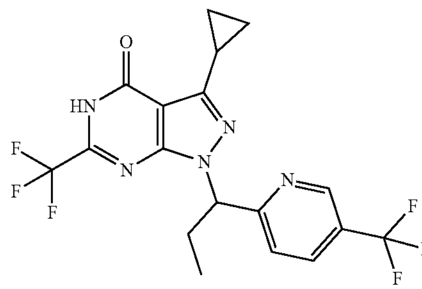

The title compound can be made according to Scheme C, using 2,2,2-trifluoroacetic anhydride and 5-amino-3-cyclopropyl-1-(1-(5-(trifluoromethyl)pyridin-2-yl) propyl)-1H-pyrazole-4-carboxamide.

Example 34 to Example 38 can be prepared in a manner analogous to Example 3, using the appropriate starting material and reagent substitutions.

Example 34. 3-cyclopropyl-6-methyl-1-(1-(4-(trifluoromethoxy)phenyl)ethyl)-1H-pyrazolo[3,4-d]pyrimidin-4(5H)-one

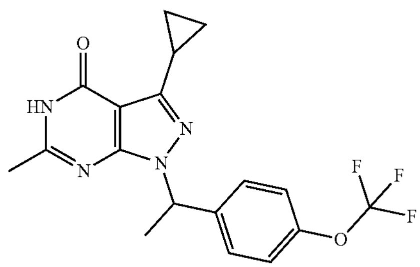 [SMILES: Cc1nc2c(c(C3CC3)nn2C(C)c2ccc(OC(F)(F)F)cc2)c(=O)[nH]1]

Example 35. 1-(1-(6-cyclopropylpyridin-3-yl)ethyl)-3,6-dimethyl-1H-pyrazolo[3,4-d]pyrimidin-4(5H)-one

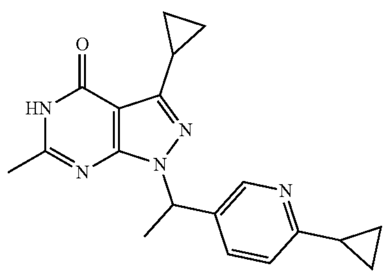 [SMILES: Cc1nc2c(c(C3CC3)nn2C(C)c2ccc(C3CC3)nc2)c(=O)[nH]1]

Example 36. 3-cyclopropyl-1-(1-(3,4-difluorophenyl)ethyl)-6-methyl-1H-pyrazolo[3,4-d]pyrimidin-4(5H)-one

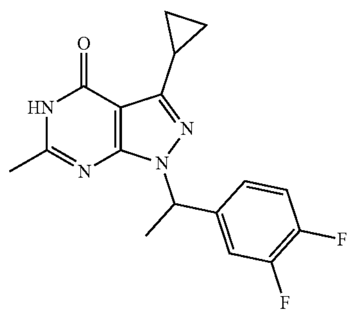 [SMILES: Cc1nc2c(c(C3CC3)nn2C(C)c2ccc(F)c(F)c2)c(=O)[nH]1]

Example 37. 3-cyclopropyl-1-(1-(2-fluoro-4-(trifluoromethyl)phenyl)ethyl)-6-methyl-1H-pyrazolo[3,4-d]pyrimidin-4(5H)-one

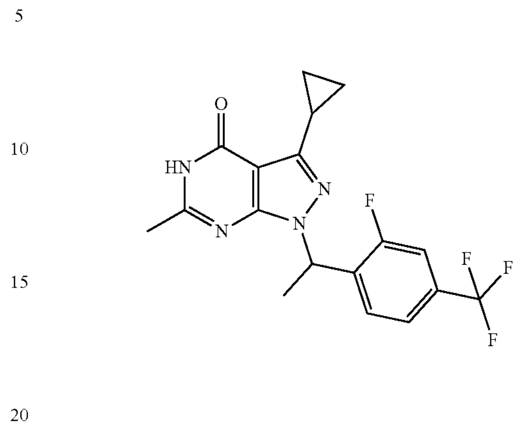

Example 38. 3-cyclopropyl-1-(1-(4-(difluoromethyl)phenyl)ethyl)-6-methyl-1H-pyrazolo[3,4-d]pyrimidin-4(5H)-one

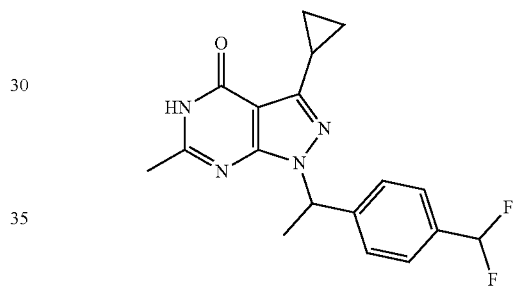

Example 39 to Example 41 can be prepared in a manner analogous to Example 3, using the appropriate starting material and reagent substitutions, including cyclopentene-1-boronic acid or cyclopentene-1-boronic acid pinacol ester, followed by subsequent reduction of the cyclopentene.

Example 39. 3-cyclopentyl-6-methyl-1-(1-(5-(trifluoromethyl)pyridin-2-yl)propyl)-1H-pyrazolo[3,4-d]pyrimidin-4(5H)-one

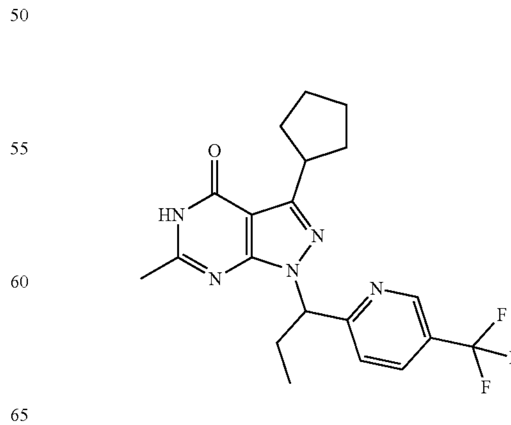

Example 40. 3-cyclopentyl-6-methyl-1-(1-(5-(trifluoromethyl)pyridin-2-yl)ethyl)-1H-pyrazolo[3,4-d]pyrimidin-4(5H)-one

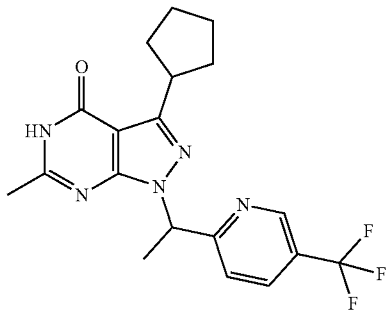 [SMILES: Cc1nc2c(c(C3CCCC3)nn2C(C)c2ccc(C(F)(F)F)cn2)c(=O)[nH]1]

Example 41. 3-cyclopentyl-6-methyl-1-(1-(6-(trifluoromethyl)pyridin-3-yl)ethyl)-1H-pyrazolo[3,4-d]pyrimidin-4(5H)-one

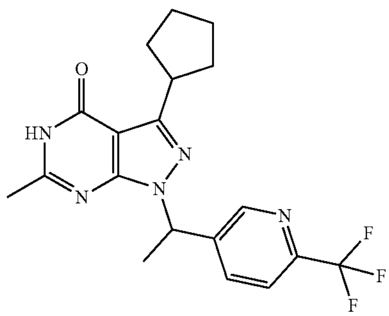 [SMILES: Cc1nc2c(c(C3CCCC3)nn2C(C)c2ccc(C(F)(F)F)nc2)c(=O)[nH]1]

Example 42 to Example 43 can be prepared in a manner analogous to Example 3, using the appropriate starting material and reagent substitutions, including cyclohexene-1-boronic acid or cyclohexene-1-boronic acid pinacol ester, followed by subsequent reduction of the cyclohexene.

Example 42. 3-cyclohexyl-6-methyl-1-(1-(5-(trifluoromethyl)pyridin-2-yl)propyl)-1H-pyrazolo[3,4-d]pyrimidin-4(5H)-one

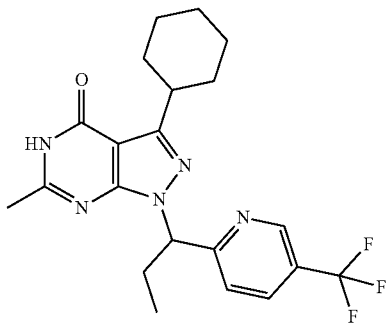 [SMILES: CCC(c1ccc(C(F)(F)F)cn1)n1nc(C2CCCCC2)c2c(=O)[nH]c(C)nc21]

Example 43. 3-cyclohexyl-6-methyl-1-(1-(6-(trifluoromethyl)pyridin-3-yl)ethyl)-1H-pyrazolo[3,4-d]pyrimidin-4(5H)-one

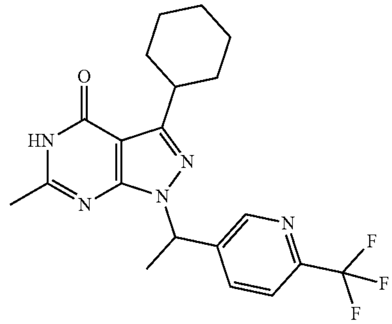 [SMILES: Cc1nc2c(c(C3CCCCC3)nn2C(C)c2ccc(C(F)(F)F)nc2)c(=O)[nH]1]

Pharmacological Examples

The present disclosure will be further illustrated by the following pharmacological examples. These examples are understood to be exemplary only and are not intended to limit the scope of the embodiments disclosed herein.

Enzymatic Assay

An IMAP TR-FRET-based phosphodiesterase assay was developed using the PDE2A isoform. IMAP technology is based on high-affinity binding of phosphate by immobilized metal (MIII) coordination complexes on nanoparticles. The IMAP "binding reagent" recognizes phosphate groups on AMP or GMP generated from cAMP or cGMP in a PDE reaction. Cyclic nucleotides that carry a phosphodiester bond and not a free phosphate are not recognized by the binding reagent. The time resolved fluorescence resonance energy transfer (TR-FRET) is afforded by a Terbium (Tb)-Donor pre-bound to the nanoparticles. FRET occurs when the fluorescent-labeled AMP or GMP product of a PDE reaction binds and comes into close proximity to the Tb-Donor complex. Due to the long lifetime of Tb fluorescence, detection can be run in time-resolved mode to reduce or eliminate interference from auto-fluorescent compounds.

The IMAP TR-FRET PDE2A assay was performed in 1536-well white plates. A total of 250 pg per well of FLAG-tagged PDE2A1 (amino acids 2-941) was dispensed in 2.5 μL IMAP assay buffer consisting of 10 mM Tris pH 7.2, 10 mM $MgCl_2$, 1 mM DTT, and 0.1% fatty acid free BSA. 30 nL of compound was then added from 1 mM stocks in DMSO using a Kalypsys Pintool. Plates were incubated for 5 min at room temperature before dispensing 1.5 μL of 533 nM FAM-CAMP substrate for a final concentration of 200 nM. Following a brief centrifugation, plates were incubated for 30 min at room temperature. The assay was terminated by adding 5 μL IMAP binding reagent Tb complex to each well which was prepared according to manufacturer's recommendations (Molecular Devices). Plates were incubated an additional 120 minutes at room temperature and read on a Viewlux plate reader. All compounds were solvated at a concentration of 10 mM in DMSO and tested in 11-point half-log dose-response. Curve fitting and $IC_{50}$ values were determined using a standard four parameter fit.

| PDE2 ($pIC_{50}$) | Example Numbers |
|---|---|
| >7 | 1, 2, 5, 8, 9, 10, 11, 12, 13, 17, 19, 21, 23, 25 |
| 6-7 | 3, 6, 7, 15 |
| 5-6 | 14, 20, 22, 24, 26 |
| <5 | 4, 16, 18 |

Biological Examples

The present disclosure will be further illustrated by the following biological examples. These examples are understood to be exemplary only and are not intended to limit the scope of the embodiments disclosed herein.

Behavioral Assays

Numerous behavioral assays are available to assess the ability of a candidate compound to enhance memory formation, including contextual conditioning (e.g., fear conditioning), temporal conditioning (e.g., trace conditioning), and object recognition. Other non-limiting examples of appropriate assays to assess memory include those that incorporate or relate to multiple training sessions, spaced training sessions, contextual fear training with single or multiple trials, trace fear conditioning with single or multiple trials, contextual memory generally, temporal memory, spatial memory, episodic memory, passive avoidance memory, active avoidance memory, food preference memory, conditioned taste avoidance, and social recognition memory.

The behavioral assays can also be used in accordance with the present embodiments, as will be understood by those of ordinary skill in the art. These assays can be directed towards the evaluation of, without limitation, hippocampus-, cortex, and/or amygdala-dependent memory formation or cognitive performance.

Biological Example 1

Effect of PDE2 Inhibitors on Contextual Memory

Rationale

Contextual fear conditioning is a form of associative learning in which animals learn to recognize a training environment (conditioned stimulus, CS) that has been previously paired with an aversive stimulus such as foot shock (unconditioned stimulus, US). When exposed to the same context at a later time, conditioned animals show a variety of conditional fear responses, including freezing behavior. The percent of time during the test that the animal exhibits such freezing provides a quantitative measure of the contextual associative memory (e.g., Fanselow, *Behav. Neurosci.* 1984, 98, 269-277; Fanselow, *Behav. Neurosci.* 1984, 98, 79-95; and Phillips and LeDoux, *Behav. Neurosci.* 1992, 106, 274-285).

Contextual conditioning has been extensively used to investigate the neural substrates mediating fear-motivated learning (e.g., Phillips and LeDoux, *Behav. Neurosci.* 1992, 106, 274-285; Kim et al., *Behav. Neurosci.* 1993, 107, 1093-1098; and Bourtchouladze et al., *Learn. Mem.* 1998, 5, 365-374). Studies in mice and rats have provided evidence for functional interaction between hippocampal and nonhippocampal systems during contextual conditioning training (e.g., Maren et al., *Behav. Brain Res.* 1997, 88, 261-274; Maren et al., *Neurobiol. Learn. Mem.* 1997, 67, 142-149; and Frankland et al., *Behav. Neurosci.* 1998, 112, 863-874). Specifically, post-training lesions of the hippocampus (but not pre-training lesions) greatly reduced contextual fear, implying that: 1) the hippocampus is essential for contextual memory but not for contextual learning per se and 2) in the absence of the hippocampus during training, non-hippocampal systems can support contextual conditioning.

Contextual conditioning has been extensively used to study the impact of various mutations on hippocampus-dependent learning, as well as strain and genetic background differences in mice (e.g., Bourtchouladze et al., *Cell* 1994, 79, 59-68; Bourtchouladze et al., *Learn Mem.* 1998, 5, 365-374; Kogan et al., *Current Biology* 1997, 7, 1-11; Silva et al., *Current Biology* 1996, 6, 1509-1518; Abel et al., *Cell* 1997, 88, 615-626; Giese et al., *Science* 1998, 279, 870-873; Logue et al., *Neuroscience* 1997, 80, 1075-1086; Chen et al., *Behav. Neurosci.* 1996, 110, 1177-1180; and Nguyen et al., *Learn Mem.* 2000, 7, 170-179).

Because robust learning can be triggered with a few minutes training session, contextual conditioning has been especially useful to study the biology of temporally distinct processes of short- and long-term memory (e.g., Kim et al., *Behav. Neurosci.* 1993, 107, 1093-1098; Bourtchouladze et al., *Cell* 1994, 79, 59-68; Abel et al., *Cell* 1997, 88, 615-626; Logue et al., *Behav. Neurosci.* 1997, 111, 104-113; Bourtchouladze et al., *Learn. Mem.* 1998, 5, 365-374; and Nguyen et al., *Learn. Mem.* 2000, 7, 170-179). As such, contextual conditioning provides an excellent model to evaluate the effects of novel drug compounds on hippocampal-dependent memory formation.

Procedures

Previous investigations have established that training with 1× or 2×CS-US pairings induces sub-maximal (weak) memory in wild-type mice (e.g., U.S.2009/0053140; Tully et al., *Nat. Rev. Drug Discov.* 2003, 2, 267-77; and Bourtchouladze et al., *Learn. Mem.* 1998, 5, 365-374). Such sub-maximal memory is facilitated by augmenting CREB, while inhibition of CREB impairs maximal memory induced with 5×CS-US pairings (Barad et al., *Proc Natl Acad Sci.* 1998, 95, 15020-15025; Peters et al., *Genes Brain Behav.* 2009, 8, 320-329). Accordingly, contextual conditioning in this study was performed as described by Barad et al., *Proc Natl Acad Sci.* 1998, 95, 15020-15025 and Peters et al., *Genes Brain Behav.* 2009, 8, 320-329.

Long-Evans male rats (each weighing about 330-450 grams) were used for contextual conditioning. Rats were group-housed in a standard laboratory and maintained on a 12:12 light-dark cycle. The experiments were always conducted during the light phase of the cycle. Except for testing times, the animals had ad libidum access to food and water. To assess contextual memory, a modified contextual fear conditioning task originally developed for evaluation of memory in CREB knock-out mice was used (Bourtchouladze et al., 1994). Training sessions comprised a baseline period in the conditioning chamber (Med Associates, Inc.) followed by presentation of unconditioned stimuli (1-5 footshocks each at 0.2-1.0 mA for 2-sec) spaced at 60-sec intervals. Thirty seconds following the last shock, the animal was returned to its home cage. One to 7 days later, the animals were returned to the chamber and freezing behavior was scored. Freezing (complete immobility except respiration) was scored by Video Freeze software (Med Associates, Inc.) over an 8 minute test period. Treatment with cognition enhancers is expected to significantly increase freezing when compared to controls.

All experiments were designed and performed in a counterbalanced fashion. In each experiment, the experimenter was unaware (blind) to the treatment of the subjects during training and testing. Training and test sessions were recorded as digital video files. Data were analyzed by one-way ANOVA with appropriate planned comparison tests using GraphPad Prism or JMP software packages.

Results

Exemplary compounds of Formula (I) were tested for enhancement of contextual memory in the fear conditioning assay. For one or more compounds, significant enhancing effects were seen at several concentrations.

Biological Example 2

Effect of PDE2 Inhibitors on Novel Object Recognition

Rationale

Novel Object Recognition (NOR) is an assay of recognition learning and memory retrieval; it takes advantage of the spontaneous preference of rodents to investigate a novel object compared with a familiar one. It is an ethologically relevant task, which in contrast to fear conditioning, does not result from negative reinforcement (foot shock) (e.g., Ennaceur and Delacour, *Behav. Brain Res.* 1988, 31, 47-59).

The NOR test has been employed extensively to assess the potential cognitive-enhancing properties of novel compounds derived from high-throughput screening. In object recognition, the task relies on the natural curiosity of rodents to explore novel objects in their environments more than familiar ones. Obviously, for an object to be "familiar," the animal must have attended to it before and remembered that experience. Hence, animals with better memory will attend and explore a new object more than an object familiar to them. During testing, the animal is presented with the training object and a second, novel one. Memory of the training object renders it familiar to the animal, and it then spends more time exploring the new novel object rather than the familiar one (Bourtchouladze et. al., *Proc. Natl. Acad. Sci. USA* 2003, 100, 10518-10522).

Neuroimaging, pharmacological, and lesion studies have demonstrated that the hippocampus and adjacent perirhinal cortex are critical for object recognition memory in rodents, monkeys, and humans (e.g., Mitchell, *Behav. Brain Res.* 1998, 97, 107-113; Teng et al., *J. Neurosci.* 2000, 20, 3853-3863; Mumby, *Brain Res.* 2001, 127, 159-181; Eichenbaum et al., *Annu. Rev. Neurosci.* 2007, 30, 127-152; Squire et al., *Nat. Rev. Neurosci.* 2007, 8, 872-883; and Vann and Alabasser, *Curr. Opin. Neurobiol.* 2011, 21, 440-445). Hence, object recognition provides an excellent behavioral model to evaluate drug-compound effects on cognitive tasks associated with function of the hippocampus and cortex.

Procedures

Object recognition was tested in Long-Evans male rats (each weighing about 330-450 grams) using the following protocol. Animals were briefly handled by the experimenter 2-5 days prior to training. Each compound was administered between 15 minutes and 24-hours prior to, or following, training. Habituation sessions (duration 1-20 min, over 1-3 days) were conducted to familiarize the animal to the arena. During training trials (duration of 1-20 min) the animals were allowed to explore two identical objects. A test trial (duration of 1-20 min) was then performed 1-96 h later.

For novel object recognition, one object was replaced with one that is novel. All combinations and locations of objects were used in a balanced manner to reduce potential biases attributable to preference for particular locations or objects. Training and test trials were recorded and scored by video-tracking software (e.g. Noldus Ethovision). An animal was scored as exploring an object when its head was oriented toward the object within a distance of 1-2 cm (rat) or when its nose was touching the object. Turning around, climbing, or sitting on an object was not considered as exploration. If the animal generates a long-term memory for the familiar object, it will spend significantly more time exploring the novel object compared to the familiar object during the retention test (Cognitive enhancers are therefore expected to facilitate this discrimination between the familiar and novel object).

A discrimination index was calculated as previously described (Bourtchouladze et al., *Proc. Natl. Acad. Sci. USA* 2003, 100, 10518-10522). In each experiment, the experimenter was unaware (blind) to the treatment of the subjects during training and testing. Data were analyzed by one-way ANOVA with appropriate planned comparison tests using GraphPad Prism or JMP software packages.

Results

Exemplary compounds of Formula (I) are tested for enhancement of memory in the NOR assay. For one or more compounds, significant enhancing effects are seen.

The specification, including the examples, is intended to be exemplary only, and it will be apparent to those skilled in the art that various modifications and variations can be made in the present embodiments without departing from the scope or spirit of the invention as defined by the appended claims.

Furthermore, while certain details in the present disclosure are provided to convey a thorough understanding of the invention as defined by the appended claims, it will be apparent to those skilled in the art that certain embodiments may be practiced without these details. Moreover, in certain instances, well-known methods, procedures, or other specific details have not been described to avoid unnecessarily obscuring aspects of the invention defined by the appended claims.

What is claimed is:

1. A pharmaceutical composition comprising: a pharmaceutically acceptable carrier;

and a compound, or a pharmaceutically acceptable salt thereof, selected from group consisting of:

3-cyclopropyl-6-methyl-1-[(1S)-1-[5-(trifluoromethyl)pyridin-2-yl]propyl]-1H,4H,5H-pyrazolo[3,4-d]pyrimidin-4-one;

3-cyclopropyl-6-methyl-1-[(1R)-1-[6-(trifluoromethyl)pyridin-3-yl]propyl]-1H,4H,5H-pyrazolo[3,4-d]pyrimidin-4-one;

3-cyclopropyl-6-methyl-1-[(1S)-1-[5-(trifluoromethyl)pyridin-2-yl]ethyl]-1H,4H,5H-pyrazolo[3,4-d]pyrimidin-4-one; and 3-cyclopropyl-6-methyl-1-{1-[4-(trifluoromethyl)phenyl]ethyl}-1H,4H,5H-pyrazolo[3,4-d]pyrimidin-4-one.

2. The pharmaceutical composition of claim 1, wherein the compound is 3-cyclopropyl-6-methyl-1-[(1S)-1-[5-(trifluoromethyl)pyridin-2-yl]propyl]-1H,4H,5H-pyrazolo[3,4-d]pyrimidin-4-one, or a pharmaceutically acceptable salt thereof.

3. The pharmaceutical composition of claim 1, wherein the compound is 3-cyclopropyl-6-methyl-1-[(1R)-1-[6-(trifluoromethyl)pyridin-3-yl]propyl]-1H,4H,5H-pyrazolo[3,4-d]pyrimidin-4-one, or a pharmaceutically acceptable salt thereof.

4. The pharmaceutical composition of claim 1, wherein the compound is 3-cyclopropyl-6-methyl-1-[(1S)-1-[5-(trifluoromethyl)pyridin-2-yl]ethyl]-1H,4H,5H-pyrazolo[3,4-d]pyrimidin-4-one, or a pharmaceutically acceptable salt thereof.

5. The pharmaceutical composition of claim 1, wherein the compound is 3-cyclopropyl-6-methyl-1-{1-[4-(trifluoromethyl)phenyl]ethyl}-1H,4H,5H-pyrazolo[3,4-d]pyrimidin-4-one, or a pharmaceutically acceptable salt thereof.

6. A method of treating a subject suffering from or diagnosed with a disorder mediated by PDE2 activity, comprising administering to the subject an effective amount of the pharmaceutical composition of claim 1.

7. A method of modulating PDE2 activity in a human subject, comprising exposing the subject to an effective amount of the pharmaceutical composition of claim 1.

8. A method of treating a neurological disorder, comprising administering to a subject suffering from or diagnosed with the disorder an effective amount of the pharmaceutical composition of claim 1, wherein the neurological disorder is selected from the group consisting of a CNS disorder;

a mental or psychiatric disorder; a neurodevelopmental disorder; a schizophrenia spectrum or psychotic disorder; a depressive disorder; a cognitive disorder; and a neurodegenerative disorder.

9. A method of treating a mental or psychiatric disorder, comprising administering to a subject suffering from or diagnosed with the disorder an effective amount of the pharmaceutical composition of claim 2.

10. A method of treating a neurodevelopmental disorder, comprising administering to a subject suffering from or diagnosed with the disorder an effective amount of the pharmaceutical composition of claim 2.

11. A method of treating a schizophrenia spectrum or psychotic disorder, comprising administering to a subject suffering from or diagnosed with the disorder an effective amount of the pharmaceutical composition of claim 2.

12. A method of treating a depressive disorder, comprising administering to a subject suffering from or diagnosed with the disorder an effective amount of the pharmaceutical composition of claim 2.

13. A method of treating a cognitive disorder, comprising administering to a subject suffering from or diagnosed with the disorder an effective amount of the pharmaceutical composition of claim 2.

14. A method of treating a neurodegenerative disorder, comprising administering to a subject suffering from or diagnosed with the disorder an effective amount of the pharmaceutical composition of claim 2.

15. A method of treating a mental or psychiatric disorder, comprising administering to a subject suffering from or diagnosed with the disorder an effective amount of the pharmaceutical composition of claim 3.

16. A method of treating a cognitive disorder, comprising administering to a subject suffering from or diagnosed with the disorder an effective amount of the pharmaceutical composition of claim 3.

17. A method of treating a mental or psychiatric disorder, comprising administering to a subject suffering from or diagnosed with the disorder an effective amount of the pharmaceutical composition of claim 4.

18. A method of treating a cognitive disorder, comprising administering to a subject suffering from or diagnosed with the disorder an effective amount of the pharmaceutical composition of claim 4.

19. A method of treating a mental or psychiatric disorder, comprising administering to a subject suffering from or diagnosed with the disorder an effective amount of the pharmaceutical composition of claim 5.

20. A method of treating a cognitive disorder, comprising administering to a subject suffering from or diagnosed with the disorder an effective amount of the pharmaceutical composition of claim 5.

* * * * *